US012358885B2

(12) United States Patent
Matinkhoo et al.

(10) Patent No.: US 12,358,885 B2
(45) Date of Patent: Jul. 15, 2025

(54) SUBSTITUTED N-PROPYLAMINE FUSED HETEROCYCLIC MESCALINE DERIVATIVES

(71) Applicant: Enveric Biosciences Canada Inc., Calgary (CA)

(72) Inventors: Kaveh Matinkhoo, Calgary (CA); David James Press, Calgary (CA); Glynnis Elizabeth Jensen, Calgary (CA); Ye Cai, Edmonton (CA); Jillian M. Hagel, Calgary (CA); Peter J. Facchini, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

(21) Appl. No.: 18/512,910

(22) Filed: Nov. 17, 2023

(65) Prior Publication Data
US 2024/0199568 A1 Jun. 20, 2024

Related U.S. Application Data

(60) Provisional application No. 63/426,553, filed on Nov. 18, 2022.

(51) Int. Cl.
*C07D 317/58* (2006.01)
*C07D 405/06* (2006.01)

(52) U.S. Cl.
CPC ......... *C07D 317/58* (2013.01); *C07D 405/06* (2013.01)

(58) Field of Classification Search
CPC .................................................. C07D 317/58
USPC ....................................................... 514/422
See application file for complete search history.

(56) References Cited

FOREIGN PATENT DOCUMENTS

| WO | 2017066103 A1 | 4/2017 |
| WO | 2022047583 A1 | 3/2022 |

OTHER PUBLICATIONS

Solvhoj et al., Chem-A Eu J (2015) vol. 21(45), 16272-279.*
Laabs, Tetrahed. (2002), 58(7), 1317-34.*
Jiang et al., Angew. Chem. Int. Edit. (2011) vol. 50(5), 1072-75.*
Souers et al., Bioorg. Biochem. Letts. (2004) vol. 14(19), 4883-86.*
Benigni et al., Farmaco, Edizione Scientifica (1975) 30(8), 642-9.*
Higginbotham, C., "Introductory Organic Chemistry", published Jan. 1, 2021.
Bock and Bermudez, 2021, FEBS Journal 288: 2513-2528.
McCorvy and Roth, 2015, Pharmacology and Therapeutics 150: 129-142.
Inserra et al., 2020, Pharmacol. Rev 73: 202.
Haleem, Darakhsan, Behav. Pharm. 2015, 26:45-58.
McClure-Begley et al., Nat. Rev. Drug Discov. 2022, 21:463-473.
Cao et al. Science 2022, 375:403-411.
Przegaliński et al., 2023, Nutrients 15:1449.
Quintero-Villegas and Valdés-Ferrer, 2022, Molecular Medicine 28: 70.
Saggu et al., 2023, Molecular Psychiatry 28: 588-600.
Boiko et al., 2022, Neurochemical Research 47: 2909-2924.
Kim, 2023, International Journal of Molecular Sciences 24: 6742.
Taciak et al.Pharmacol. Rep. 2018, 70:37-46.
Finnin, B. and Morgan, T.M., 1999 J. Pharm. Sci, 88 (10), 955-958.
Ross et al. ACS Pharmacol. Transl. Sci. 4: 553-562, 2021.
Romeo et al. J. Psychiatr. Res. 137: 273-282, 2021.
Simmler et al., 2013, British J. Pharmacol. 168: 458.
Halberstadt et al., 2019, J. Psychopharm. 33: 406-414.
Halberstadt, 2015, Behav. Brain Res. 277: 99.
Rojas and Felder, 2016, Frontiers in Cellular Neuroscience 10:272.
Polter and Li, 2010, Cell Signaling 22:1406-1412.
Bogenschutz, M.P. and Johnson M. W. (2016), Prog. in Neuro-Psychopharmacol. & Biol. Psychiatry 64; 250-258.
Romeu, A.G et al. (2017), Exp. Clin. Psychopharmacol. Aug. 2016; 24(4): 229-268.
Devroye et al Pharmacol. Ther. 2018, 181:143-155.
Segelcke, et al. Cephalalgia 2017, 37:365-371.
Savino et al., 2023, Brain Science 13: 734.
Salatino-Oliveira_Am. J. Med. Genet. B Neuropsychiatr. Genet. 2018, 177:211-231.
Outhred et al. Neurosci. Biobehav. Rev, 2013, 37:1786-800.
Augsburger et al.Pharmaceutical Dosage Forms: Tablets, vol. 1-vol. 3, by CRC Press (2008).
Y. Zou et al., Eur. J. Med. Chem., 138, 199-211 (2017).
K. N. Campbell et al., J. Org. Chem., 16, 1736 -1740 (1951).
D. Ghosh, et al., Tetrahedr. Lett., 58, 2014-2018 (2017).
M. G. Cabiddu et al., Tetrahedron 59, 4383-4387 (2003).
Rickli et al., 2015, Neuropharmacology 99: 546.
Rickli et al., 2016, Eur. Neuropharm. 26: 1327.
Owens et al., 1997, Journal of Pharmacology and Experimental Therapeutics 283:1305-1322.
Celada et al., 2013, CNS Drugs 27:703-716.
Marcher-Rørsted et al., 2020, ACS Chem. Neurosci. 11: 1238.
Larsson et al., 1990, Neuropharmacology 29:85-91.
Langin et al., [Eur. J. Pharmacol. 167:95-104, 1989.
Mackenzie et al., [Eur. J. Pharmacol. 266:79-85, 1994.
Witt-Endersby and Dubocovich [Mol. Pharmacol. 50:166-174, 1996.
Mulheron et al., [J. Biol. Chem. 269: 12954-12962, 1994.
Bryant et al., [Life Sci. 15:1259-1268, 1996.
Kursar et al., [Mol. Pharmacol. 46: 227-234, 1994.
Shen et al., [J. Biol. Chem. 268: 18200-18204, 1993.
Tatsumi et al., [Eur J Pharmacol 368: 277-283, 1999.

(Continued)

*Primary Examiner* — Taofiq A Solola
(74) *Attorney, Agent, or Firm* — Smart & Biggar LP; Michael Fenwick

(57) ABSTRACT

Disclosed are novel fused mescaline derivative compounds, notably substituted N-propylamine fused heterocyclic mescaline derivatives, including substituted N-propylamine fused dioxolane mescaline derivatives, and pharmaceutical and recreational drug formulations containing the same. Methods of making and using these compounds are also disclosed.

12 Claims, 37 Drawing Sheets

(56) References Cited

OTHER PUBLICATIONS

Pacholczyk et al., [Nature 350: 350-354, 1991.
Pristupa et al., [Mol. Pharmacol. 45: 125-135, 1994.
Augsburger et al. PharmDosForms Tablets_Vol2_2008.
Liberman et al; PharmDosFormsTablets_Vol1_2008.

* cited by examiner

FIG. 3A (ii)

FIG. 3B (ii)
FIG. 3B (iii)

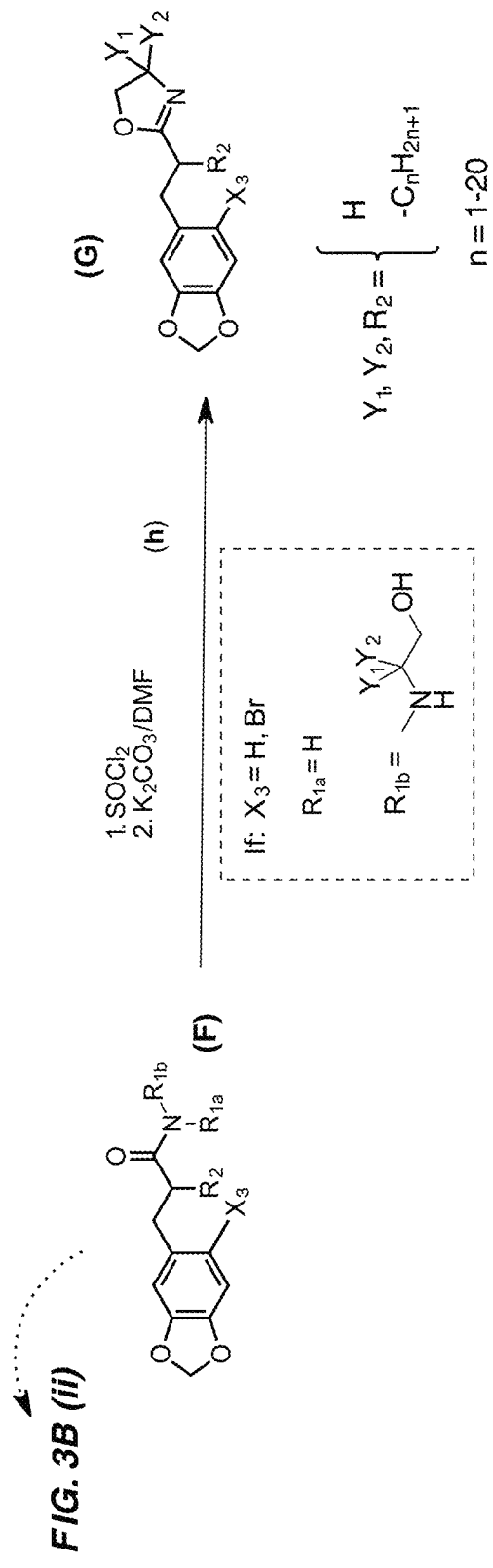
FIG. 3B (iii)

MM735                      MM736

SUBSTITUTED N-PROPYLAMINE FUSED HETEROCYCLIC MESCALINE DERIVATIVES

RELATED APPLICATION

This application claims the benefit of U.S. Provisional Application No. 63/426,553 filed Nov. 18, 2022; the entire content of U.S. Patent Application No. 63/426,553 is hereby incorporated by reference.

FIELD OF THE DISCLOSURE

The compositions and methods disclosed herein relate to a chemical compound known as mescaline. Furthermore, the compositions and methods disclosed herein relate in particular to fused heterocyclic mescaline derivatives, and more in particular to fused heterocyclic mescaline derivatives possessing a substituted N-propylamine chain.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Mescaline (chemical name 3,4,5 trimethoxyphenethylamine), for example, is a secondary metabolite that is naturally produced by certain cactus species belonging to a variety of genera within the plant family of Cactaceae. Cactus species which can produce mescaline include, for example, cactus species belonging to the genus *Lophophora*, including *Lophophora williamsii* (peyote) and *Lophophora diffusa* and cactus species belonging to the genus *Echinopsis/Trichocereus*, including *Echinopsis pachanoi/Trichocereus pachanoi* (also known as San Pedro), *Echinopsis peruviana/Trichocereus peruvianus* (also known as Peruvian torch), (*Echinopsis lageniformis/Trichocereus bridgesii* (also known as Bolivian torch), and *Echinopsis scopulicola/Trichocereus scopulicola*.

The interest of the art in mescaline is well established. Thus, for example, mescaline is a psychoactive compound and is therefore used as a recreational drug. Mescaline is also used in Native American religious ceremonies, and for spiritual purposes by Andean indigenous cultures. Furthermore, mescaline has been evaluated for its potential in the treatment of addictions, notably alcohol addiction (Bogenschutz, M. P. and Johnson M. W. (2016), Prog. in Neuro-Psychopharmacol. & Biol. Psychiatry 64; 250-258; Romeu, A. G. et al. (2017), Exp. Clin. Psychopharmacol. 2016 August; 24(4): 229-268).

Although the toxicity of mescaline is low, adverse side effects, including, for example, panic attacks, paranoia, and psychotic states, sometimes together or individually referred to as "a bad trip", are not infrequently experienced by mescaline users. Furthermore, mescaline can induce nausea and vomiting.

There exists therefore a need in the art for improved mescaline compounds.

SUMMARY OF THE DISCLOSURE

The following paragraphs are intended to introduce the reader to the more detailed description, not to define or limit the claimed subject matter of the present disclosure.

In one aspect, the present disclosure relates to mescaline and derivative compounds.

In another aspect, the present disclosure relates to fused heterocyclic mescaline derivatives, and methods of making and using these compounds.

In another aspect, the present disclosure relates to fused heterocyclic mescaline derivatives having a substituted N-propylamine chain and methods of making and using these compounds.

Accordingly, in one aspect, the present disclosure provides, in at least one embodiment, in accordance with the teachings herein, a compound having chemical formula (I) or (II):

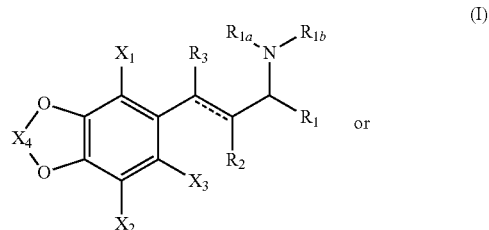

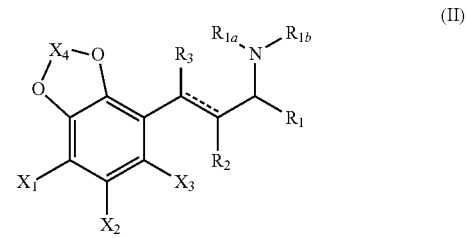

wherein, in chemical formula (I) or (II):

⟋ is a single or double bond;

$X_1$, $X_2$, and $X_3$ are independently selected from a hydrogen atom, O-alkyl, acyl, N-alkyl, OH, a halogen, or $NH_2$;

$X_4$ is an alkylene group or substituted alkylene group;

$R_1$ is a hydrogen, an alkyl group, or an oxo group, or $R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;

$R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and $R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring.

In at least one embodiment, in an aspect, the chemical compound having formula (I) can be a compound having formula ($I_a$) or ($I_b$), and the compound having formula (II) can be a compound having formula ($II_a$) or ($II_b$):

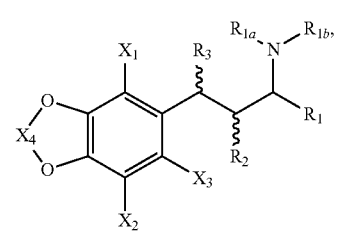
(Ia)

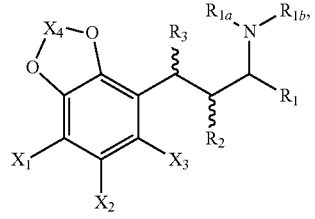
(IIa)

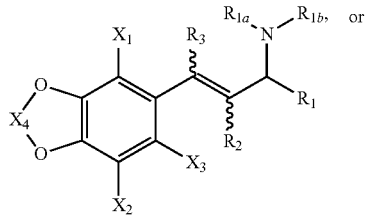
(Ib)

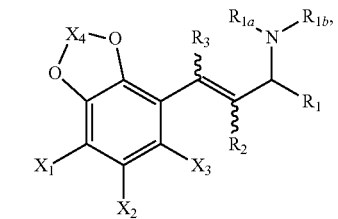
(IIb)

wherein, in chemical formula ($I_a$), ($I_b$), ($II_a$), or ($II_b$):
$X_1$, $X_2$, and $X_3$ are independently selected from a hydrogen atom, O-alkyl, acyl, N-alkyl, OH, a halogen, or $NH_2$;
$X_4$ is an alkylene group or substituted alkylene group;
$R_1$ is a hydrogen, an alkyl group, or an oxo group, or
$R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring and when the heterocyclic ring is unsaturated, $R_{1a}$ is optionally absent;
$R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and
$R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring.

In at least one embodiment, in an aspect, $X_4$ can be a ($C_1$-$C_3$)-alkylene group or a substituted ($C_1$-$C_3$)-alkylene group.

In at least one embodiment, in an aspect, $X_4$ can be a methylene group (—$CH_2$—) or a substituted methylene group.

In at least one embodiment, in an aspect, the methylene group can be substituted with at least one halogen.

In at least one embodiment, in an aspect, the substituted methylene group can be substituted with two halogen substituents.

In at least one embodiment, in an aspect, the substituted methylene group can be substituted with two identical halogen substituents, and can optionally be (—$CF_2$—).

In at least one embodiment, in an aspect, the compound having formula ($I_a$), ($I_b$), ($II_a$), and ($II_b$) can have a chemical formula ($I_c$), ($I_d$), ($II_c$), or ($II_d$):

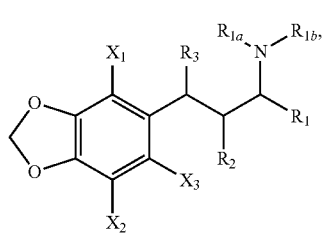
(Ic)

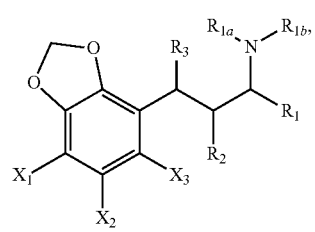
(IIc)

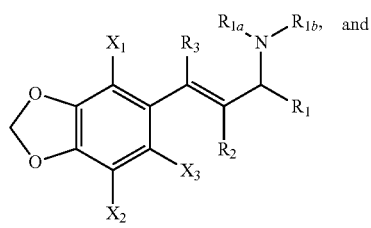
(Id)

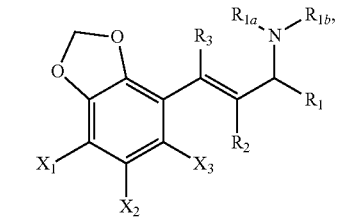
(IId)

respectively.

In at least one embodiment, in an aspect, the amino group (—$NR_{1a}R_{1b}$) can be protonated to form (—$N^+HR_{1a}R_{1b}$), and chemical formula (I), (II), ($I_a$), ($I_b$), ($II_a$), ($II_b$), ($I_c$), ($I_d$), ($II_c$), or ($II_d$) further include a negatively charged anion balancing the positively charged nitrogen atom.

In at least one embodiment, in an aspect, $X_1$, $X_2$, $X_3$, can each be a hydrogen atom (H).

In at least one embodiment, in an aspect, at least one of $X_1$, $X_2$, $X_3$, can each be an O-alkyl group or a halogen.

In at least one embodiment, in an aspect, $X_3$, can each be an O-alkyl group, optionally a methoxy group, or a halogen, optionally a bromine.

In at least one embodiment, in an aspect, $R_2$ and $R_3$ can be independently or simultaneously a $(C_1$-$C_6)$-alkyl group.

In at least one embodiment, in an aspect, $R_2$ and $R_3$ can be independently or simultaneously a $(C_1$-$C_3)$-alkyl group.

In at least one embodiment, in an aspect, $R_2$ and $R_3$ can be a methyl group.

In at least one embodiment, in an aspect, $R_2$ can be a $(C_1$-$C_6)$-alkyl group, and $R_3$ can be a hydrogen atom.

In at least one embodiment, in an aspect, $R_2$ can be a $(C_1$-$C_3)$-alkyl group, and $R_3$ can be a hydrogen atom.

In at least one embodiment, in an aspect, $R_2$ can be a methyl group or ethyl group, and $R_3$ can be a hydrogen atom.

In at least one embodiment, in an aspect, $R_3$ can be a $(C_1$-$C_6)$-alkyl group, and $R_2$ can be a hydrogen atom.

In at least one embodiment, in an aspect, $R_3$ can be a $(C_1$-$C_3)$-alkyl group, and $R_2$ can be a hydrogen atom.

In at least one embodiment, in an aspect, $R_3$ can be a methyl group, and $R_2$ can be a hydrogen atom.

In at least one embodiment, in an aspect, $R_2$ and $R_3$ can each be a methoxy group.

In at least one embodiment, in an aspect, $R_2$ can be independently or simultaneously a $(C_1$-$C_6)$—O-alkyl group, and $R_3$ can be a hydrogen atom.

In at least one embodiment, in an aspect, $R_2$ can be independently or simultaneously a $(C_1$-$C_3)$—O-alkyl group, and $R_3$ can be a hydrogen atom.

In at least one embodiment, in an aspect, $R_2$ can be a methoxy group, and $R_3$ can be a hydrogen atom.

In at least one embodiment, in an aspect, $R_3$ can be a $(C_1$-$C_6)$—O-alkyl group, and $R_2$ can be a hydrogen atom.

In at least one embodiment, in an aspect, $R_3$ can be a $(C_1$-$C_3)$—O-alkyl group, and $R_2$ can be a hydrogen atom.

In at least one embodiment, in an aspect, $R_3$ can be a methoxy group, and $R_2$ can be a hydrogen atom.

In at least one embodiment, in an aspect, $R_2$ and $R_3$ can each be a hydrogen atom.

In at least one embodiment, in an aspect, in formula ($I_a$), ($II_a$), ($I_c$), or ($II_c$) $R_2$ and $R_3$ can be joined together along with an oxygen atom to form an oxirane ring.

In at least one embodiment, in an aspect, $R_{1a}$ can be a hydrogen atom and $R_{1b}$ can be a $(C_1$-$C_6)$-alkyl group.

In at least one embodiment, in an aspect, $R_{1a}$ and $R_{1b}$ can be independently or simultaneously a $(C_1$-$C_6)$-alkyl group.

In at least one embodiment, in an aspect, $R_{1a}$ and $R_{1b}$ can be independently or simultaneously a $(C_1$-$C_3)$-alkyl group.

In at least one embodiment, in an aspect, $R_{1a}$ can be a hydrogen atom and $R_{1b}$ can be a $(C_1$-$C_6)$-hydroxylalkyl group.

In at least one embodiment, in an aspect, $R_{1a}$ can be a hydrogen atom and $R_{1b}$ can be a methanol group (—$CH_2OH$), ethanol group (—$C_2H_4OH$), propanol group (—$C_3H_6OH$), or a butanol group (—$C_4H_8OH$).

In at least one embodiment, in an aspect, $R_{1a}$ can be a hydrogen atom and $R_{1b}$ can be a hydroxylalkyl group having the formula (HA):

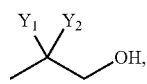

(HA)

wherein $Y_1$ and $Y_2$ are each simultaneously or independently a hydrogen atom or a $(C_1$-$C_6)$-alkyl group.

In at least one embodiment, in an aspect, $R_{1a}$ can be a hydrogen atom and $R_{1b}$ can be an alkyl-aryl group.

In at least one embodiment, in an aspect, the alkyl-aryl group can be a $(C_1$-$C_6)$-alkyl-aryl group.

In at least one embodiment, in an aspect, the alkyl-aryl group can be a $(C_1$-$C_6)$-alkyl-phenyl group.

In at least one embodiment, in an aspect, the alkyl-aryl group can be a ($CH_2$)-phenyl group.

In at least one embodiment, in an aspect, $R_{1a}$ and $R_{1b}$ can be joined together, along with the nitrogen atom to which they are attached, to form a 3-10-membered optionally substituted heterocyclic ring, wherein the heterocyclic ring further includes an oxygen atom.

In at least one embodiment, in an aspect, $R_{1a}$ and $R_{1b}$ can be joined together, along with the nitrogen atom to which they are attached, to form a 3-10-membered optionally substituted heterocyclic ring, wherein the heterocyclic ring further includes an oxygen atom, and wherein the heterocyclic ring is further substituted with at least one $(C_1$-$C_6)$-alkyl group.

In at least one embodiment, in an aspect, the heterocyclic ring can further be substituted, independently or simultaneously, with two $(C_1$-$C_6)$-alkyl groups from the same heterocyclic carbon atom.

In at least one embodiment, in an aspect, the heterocyclic ring can further be substituted with two methyl groups on one single heterocyclic carbon atom.

In at least one embodiment, in an aspect, the heterocyclic ring can further be substituted with two methyl groups on two separate heterocyclic carbon atoms.

In at least one embodiment, in an aspect, the heterocyclic ring can be a 5- or 6-membered heterocyclic ring.

In at least one embodiment, in an aspect, $R_1$ can be joined together with $R_{1b}$, together with the nitrogen atom to which $R_{1b}$ is attached, and the carbon atom to which $R_1$ is attached, to form an optionally substituted saturated or unsaturated 3-10 membered heterocyclic ring, wherein the heterocyclic ring, in addition to the nitrogen atom, includes an oxygen atom.

In at least one embodiment, in an aspect, $R_1$ can be joined together with $R_{1b}$, together with the nitrogen atom to which $R_{1b}$ is attached, and the carbon atom to which $R_1$ is attached, to form an optionally substituted saturated or unsaturated 3-10 membered heterocyclic ring, wherein the heterocyclic ring, in addition to the nitrogen atom, includes an oxygen atom, and is substituted with at least one $(C_1$-$C_6)$ alkyl group.

In at least one embodiment, in an aspect, $R_1$ can be joined together with $R_{1b}$, together with the nitrogen atom to which $R_{1b}$ is attached, and the carbon atom to which $R_1$ is attached, to form an optionally substituted saturated or unsaturated 3-10 membered heterocyclic ring, wherein the heterocyclic ring, in addition to the nitrogen atom, includes an oxygen atom, and is substituted, independently or simultaneously, with at least two $(C_1$-$C_6)$ alkyl groups, the alkyl groups being substituents on the same heterocyclic carbon atom.

In at least one embodiment, in an aspect, the alkyl group can be a methyl group.

In at least one embodiment, in an aspect, the heterocyclic ring can be partially saturated.

In at least one embodiment, in an aspect, the heterocyclic ring can be a 5- or 6-membered heterocyclic ring.

In at least one embodiment, in an aspect, when the heterocyclic ring is unsaturated, $R_{1a}$ can be absent.

In at least one embodiment, in an aspect, when the heterocyclic ring is unsaturated, and the nitrogen is participating in the formation of an unsaturated bond, $R_{1a}$ can be absent.

In at least one embodiment, in an aspect, the chemical compound having formula (I) or (II) can be selected from the group of compounds having chemical formula (A); (B); (C); (D); (E); (F); and (G):

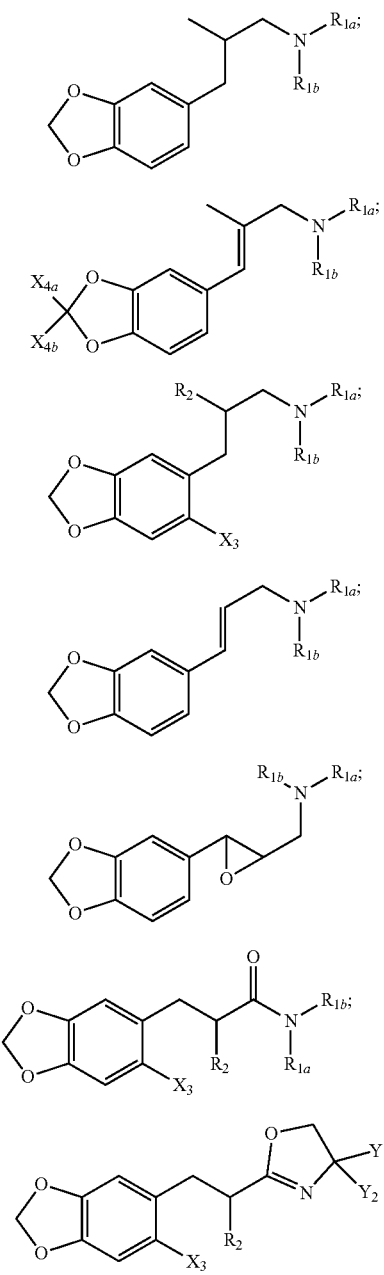

wherein in formula (B), $X_{4a}$ and $X_{4b}$ are, independently or simultaneously, a halogen or a hydrogen atom, wherein $R_{1a}$ and $R_{1b}$ in formula (A), (B), (C), (D), (E), and (F) are independently selected from an alkyl group, an optionally substituted alkyl-aryl group, or a hydrogen atom, or wherein $R_{1a}$ and $R_{1b}$ in formula (A), (B), (C), (D), (E), and (F), are joined together, along with the nitrogen atom to which they are attached, to form a 3-10-membered optionally substituted heterocyclic ring;

wherein $R_2$ in formula (C), (F), and (G), and $Y_1$ and $Y_2$ in (G) are an alkyl group or hydrogen atom; and wherein $X_3$ in formulas (C), (F), and (G) is a halogen, an O-alkyl group or hydrogen atom.

In at least one embodiment, in an aspect, the chemical compound having formula (I) can be selected from the group of compounds having the chemical formula: A(I)-A(III); B(I)-B(V); C(I)-C(XIII); D(I)-D(III); E(I)-(V); F(I)-(VI); and G(I)-G(V):

(A): A(I); A(II); and A(III):

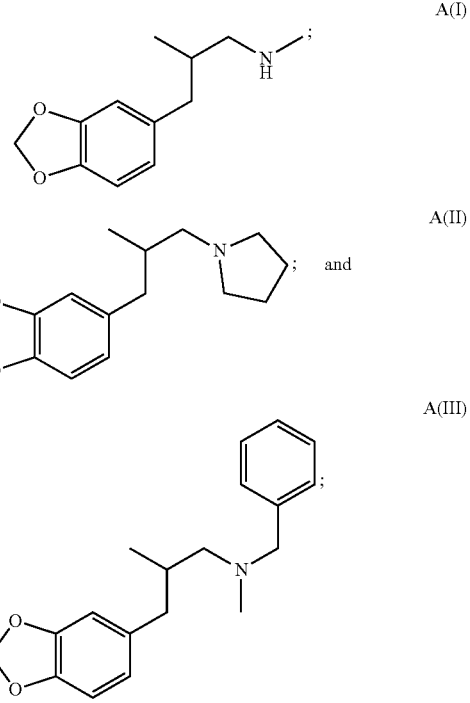

(B): B(I); B(II); B(III); B(IV); and B(V):

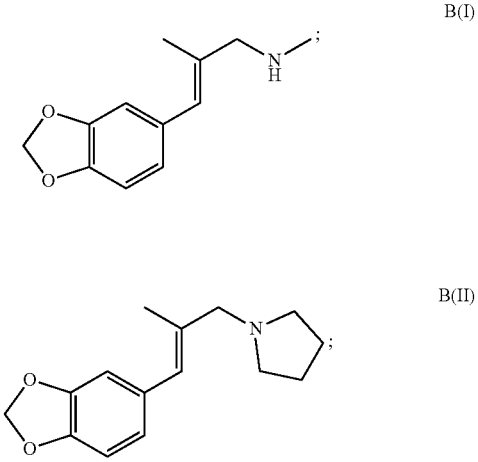

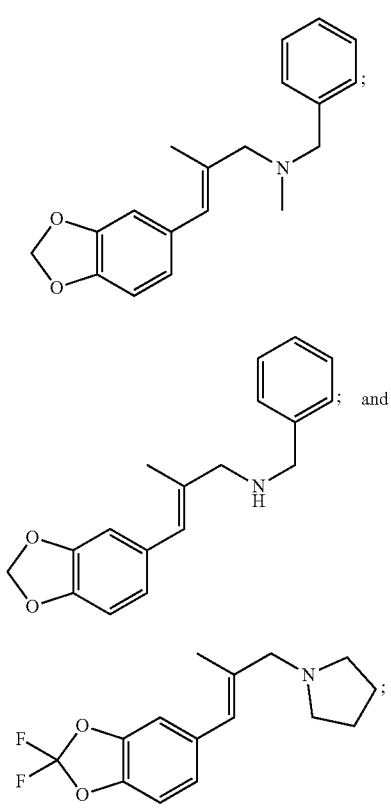
B(III);
B(IV); and
B(V);
(C): C(I); C(II); C(III); C(IV); C(V); C(VI); C(VII); C(VIII); C(IX); C(X); C(XI); C(XII); and C(XIII):
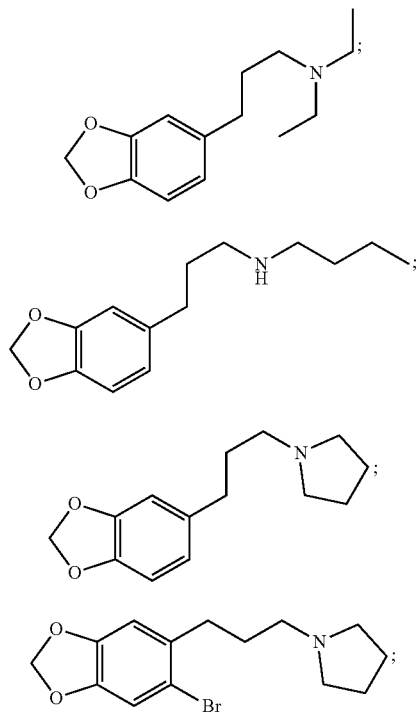
C(I)
C(II);
C(III);
C(IV);
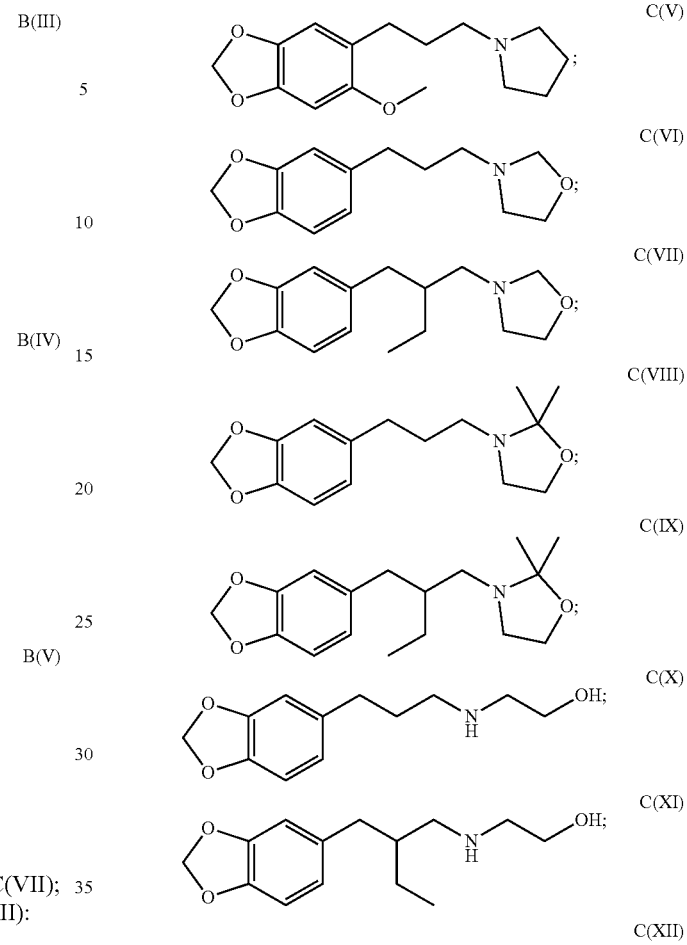
C(V);
C(VI);
C(VII);
C(VIII);
C(IX);
C(X);
C(XI);
C(XII); and
C(XIII);
(D): D(I); D(II); and D(III):
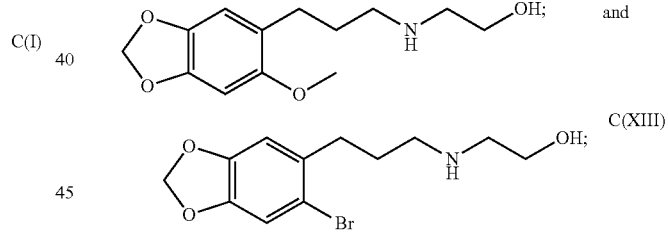
D(I)
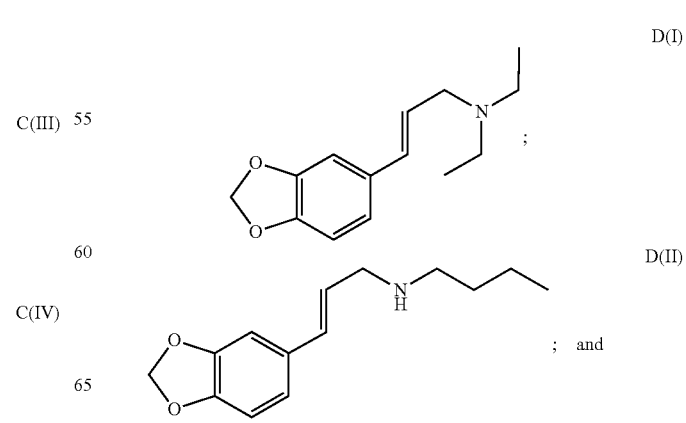
D(II); and -continued

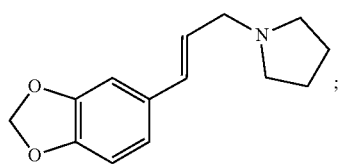

(E): E(I); E(II); E(III); E(IV); and E(V):

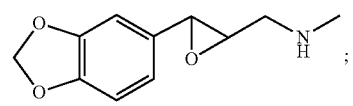
E(I)

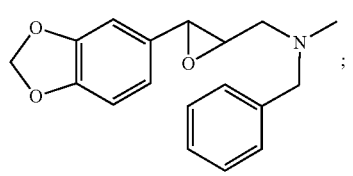
E(II)

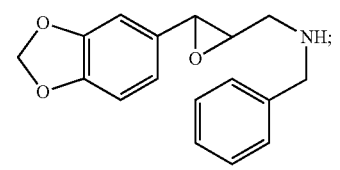
E(III)

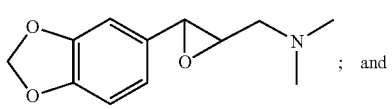
E(IV)

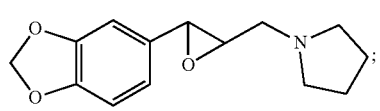
E(V)

(F): F(I); F(II); F(III); F(IV); F(V); and F(VI):

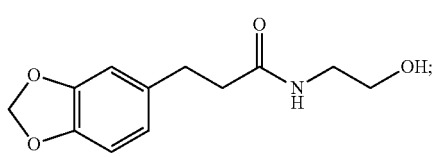
F(I)

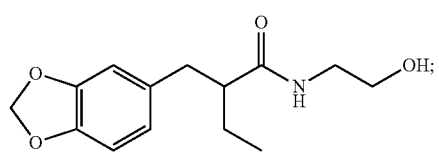
F(II)

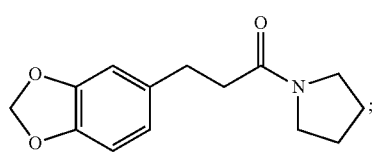
F(III)

-continued

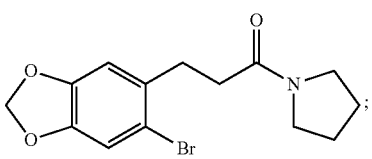
F(IV)

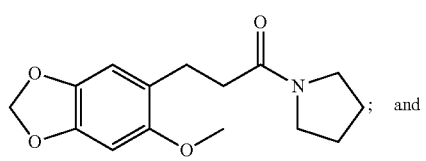
F(V) and

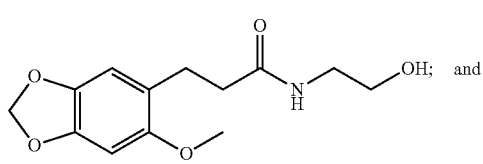
F(VI)

(G): G(I); G(II); G(III); G(IV); and G(V):

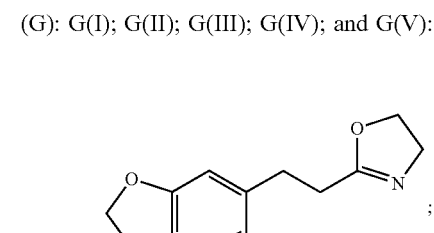
G(I)

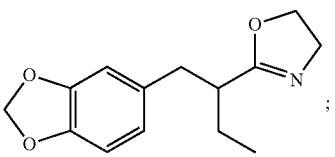
G(II)

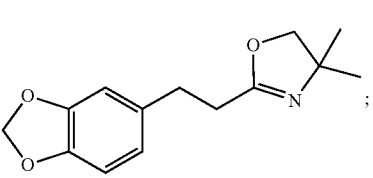
G(III)

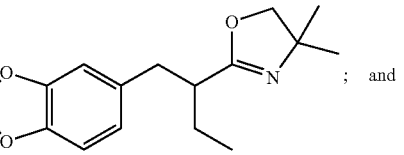
G(IV) and

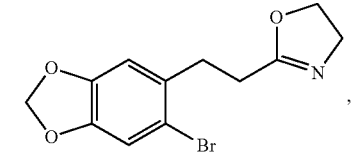
G(V)

wherein in each of compound A(I) to G(V), optionally, the nitrogen atom of the N-propylamine portion may be protonated and includes a negatively charged anion balancing the positively charged nitrogen atom.

In at least one embodiment, in an aspect, the compound can be a stereoisomeric compound selected from the stereoisomeric compounds corresponding with A(I), A(II), A(III), C(VII), C(IX), C(XI), F(II), G(II), and G(IV) comprising an N-propylamine portion wherein the $C_2$ atom of the N-propylamine portion thereof is a chiral carbon atom.

In at least one embodiment, in an aspect, the compound can be a first stereoisomeric compound present in a mixture, the mixture comprising a second stereoisomeric compound, the second stereoisomeric compound being the stereoisomeric counterpart of the first stereoisomeric compound, wherein, optionally, the mixture is a racemic mixture.

In at least one embodiment, in an aspect, the stereoisomeric compound can be substantially free from its corresponding counterpart stereoisomeric compound.

In at least one embodiment, in an aspect, the compound having formula A(II) can be selected from the stereoisomeric compounds having the formula $A(II_a)$ or $A(II_b)$:

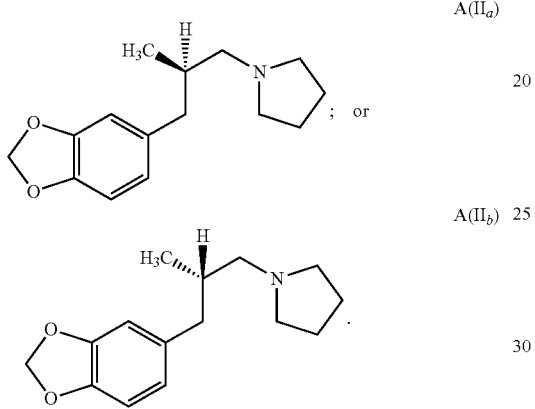

In at least one embodiment, in an aspect, the selected compound can be in a mixture further comprising the other stereoisomeric compound wherein, optionally, the mixture is a racemic mixture.

In another aspect, the present disclosure relates to pharmaceutical and recreational drug formulations comprising fused heterocyclic mescaline derivatives. Accordingly, in one aspect, the present disclosure provides, in at least one embodiment, a pharmaceutical or recreational drug formulation comprising an effective amount of a chemical compound selected from a compound having chemical formula (I) or (II):

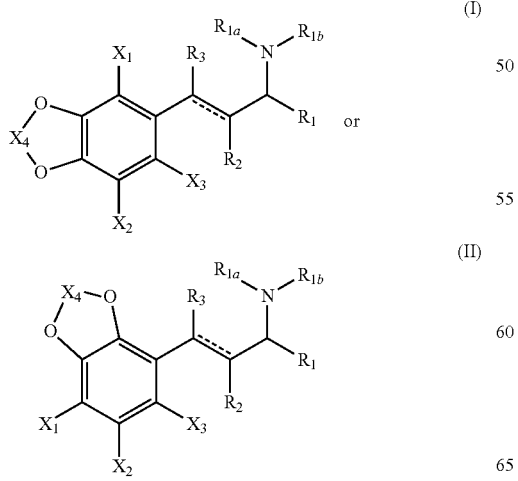

wherein, in chemical formula (I) or (II):

🗸 is a single or double bond;
$X_1$, $X_2$, and $X_3$ are independently selected from a hydrogen atom, O-alkyl, acyl, N-alkyl, OH, a halogen, or $NH_2$;
$X_4$ is an alkylene group or substituted alkylene group;
$R_1$ is a hydrogen, an alkyl group, or an oxo group, or
$R_1$, is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;
$R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and
$R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring,
together with a pharmaceutically acceptable excipient, diluent, or carrier.

In another aspect, the present disclosure relates to methods of treatment of psychiatric disorders. Accordingly, the present disclosure further provides, in one embodiment, a method for treating a brain neurological disorder, the method comprising administering to a subject in need thereof a pharmaceutical formulation comprising a compound having chemical formula (I) or (II):

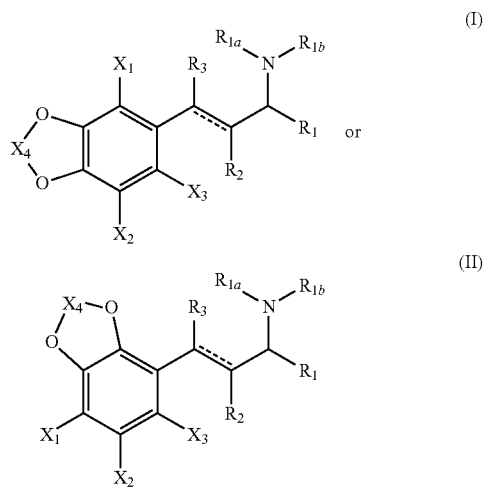

wherein, in chemical formula (I) or (II):

🗸 is a single or double bond;
$X_1$, $X_2$, and $X_3$ are independently selected from a hydrogen atom, O-alkyl, acyl, N-alkyl, OH, a halogen, or $NH_2$;
$X_4$ is an alkylene group or substituted alkylene group;
$R_1$ is a hydrogen, an alkyl group, or an oxo group, or
$R_1$ is joined together with $R_{1b}$, together with the carbon atom to which $R_1$ is attached, and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;

$R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and $R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring, wherein the pharmaceutical formulation is administered in an effective amount to treat the brain neurological disorder in the subject.

In at least one embodiment, in an aspect, upon administration the compound having chemical formula (I) or (II) can interact with a receptor in the subject to thereby modulate the receptor and exert a pharmacological effect.

In at least one embodiment, in an aspect, the receptor can be a G-protein coupled receptor (GPCR).

In at least one embodiment, in an aspect, the receptor can be a 5-HT receptor.

In at least one embodiment, in an aspect, the receptor can be a $5\text{-HT}_{1A}$ receptor, a $5\text{-HT}_{2A}$ receptor, a $5\text{-HT}_{2B}$ receptor, a $5\text{-HT}_{2C}$ receptor, a $5\text{-HT}_7$ receptor, an $\alpha_{2A}$ receptor, a $D_3$ receptor, or an $MT_1$ receptor.

In at least one embodiment, in an aspect, upon administration the compound having chemical formula (I) or (II) can interact with a transmembrane transport protein in the subject to thereby modulate the transmembrane transport protein and exert a pharmacological effect.

In at least one embodiment, in an aspect, the transmembrane transport protein can be a dopamine active transporter (DAT), a norephedrine transporter (NET), or a serotonin transporter (SERT) transmembrane transport protein.

In at least one embodiment, in an aspect, the disorder can be a G-protein coupled receptor (GPCR)-mediated disorder.

In at least one embodiment, in an aspect, the disorder can be a 5-HT receptor-mediated disorder.

In at least one embodiment, in an aspect, the disorder can be a $5\text{-HT}_{1A}$ receptor-mediated disorder, a $5\text{-HT}_{2A}$ receptor-mediated disorder, a $5\text{-HT}_{2B}$ receptor-mediated disorder, a $5\text{-HT}_{2C}$ receptor-mediated disorder, a $5\text{-HT}_{1D}$ receptor-mediated disorder, a $5\text{-HT}_7$ receptor-mediated disorder, a $\alpha_{2A}$ receptor-mediated disorder, a $D_3$ receptor-mediated disorder, or an $MT_1$ receptor-mediated disorder.

In at least one embodiment, in an aspect, a dose can be administered of about 0.001 mg to about 5,000 mg.

In another aspect, the present disclosure provides, in at least one embodiment, a method for modulating (i) a receptor selected from $5\text{-HT}_{1A}$ receptor, a $5\text{-HT}_{2A}$ receptor, a $5\text{-HT}_{2B}$ receptor, a $5\text{-HT}_{2C}$ receptor, a $5\text{-HT}_7$ receptor, an $\alpha_{2A}$ receptor, a $D_3$ receptor, or an $MT_1$ receptor; or (ii) a transmembrane transport protein selected from a dopamine active transporter (DAT), a norephedrine transporter (NET) or a serotonin transporter (SERT) transmembrane transport protein, the method comprising contacting (i) the $5\text{-HT}_{1A}$ receptor, the $5\text{-HT}_{2A}$ receptor, the $5\text{-HT}_{2B}$ receptor, the $5\text{-HT}_{2C}$ receptor, the $5\text{-HT}_7$ receptor, the $\alpha_{2A}$ receptor, the $D_3$ receptor, or the $MT_1$ receptor; or (ii) the dopamine active transporter (DAT), the norephedrine transporter (NET), or the serotonin transporter (SERT) transmembrane transport protein with a selected from a first chemical compound having chemical formula (I), and a second chemical compound having chemical formula (II):

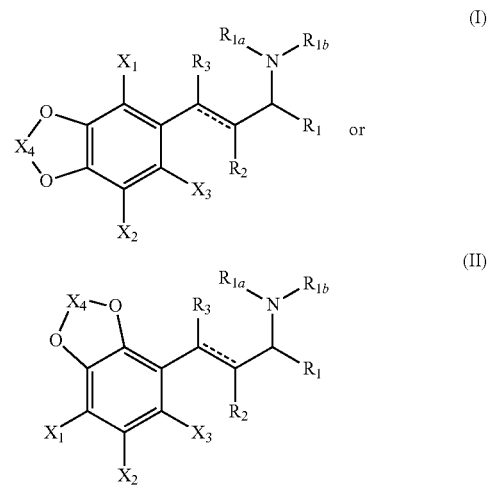

wherein, in chemical formula (I) or (II):

⚏ is a single or double bond;

$X_1$, $X_2$, and $X_3$ are independently selected from a hydrogen atom, O-alkyl, acyl, N-alkyl, OH, a halogen, or $NH_2$;

$X_4$ is an alkylene group or substituted alkylene group;

$R_1$ is a hydrogen, an alkyl group, or an oxo group, or $R_1$ is joined together with $R_{1b}$, together with the carbon atom to which $R_1$ is attached, and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;

$R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and $R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring, under reaction conditions sufficient to modulate (i) the $5\text{-HT}_{1A}$ receptor, the $5\text{-HT}_{2A}$ receptor, the $5\text{-HT}_{2B}$ receptor, the $5\text{-HT}_{2C}$ receptor, the $5\text{-HT}_7$ receptor, the $\alpha_{2A}$ receptor, the $D_3$ receptor, or the $MT_1$ receptor; (ii) the dopamine active transporter (DAT), the norephedrine transporter (NET), or the serotonin transporter (SERT) transmembrane transport protein.

In at least one embodiment, in an aspect, the reaction conditions can be in vitro reaction conditions.

In at least one embodiment, in an aspect, the reaction conditions can be in vivo reaction conditions.

In another aspect, the present disclosure relates to methods of making mescaline derivatives. Accordingly, in an aspect, in at least one embodiment, provided herein is a method of making a first chemical compound having chemical formula (I) or (II):

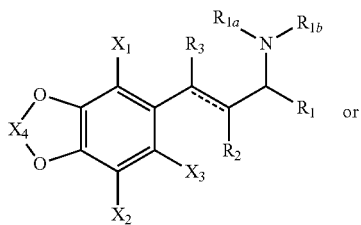

(I)

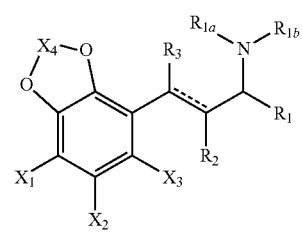

(II)

wherein, in chemical formula (I) or (II):

- ⟋⟋ is a single or double bond;
- $X_1$, $X_2$, and $X_3$ are independently selected from a hydrogen atom, O-alkyl, acyl, N-alkyl, OH, a halogen, or $NH_2$;
- $X_4$ is an alkylene group or substituted alkylene group;
- $R_1$ is a hydrogen, an alkyl group, or an oxo group, or $R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;
- $R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and
- $R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring, and wherein the method involves the performance of at least one chemical synthesis reaction selected from the reactions depicted in FIGS. 3A(i), 3A(ii), 3B(i), 3B(ii), 3B(iii), and 3C.

In at least one embodiment, in an aspect, the compound having chemical formula (I) can be a compound having formula (A):

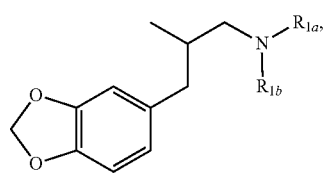

(A)

wherein $R_{1a}$ and $R_{1b}$ are each independently selected from an alkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring, and the at least one chemical synthesis reaction is a reaction selected from (g); (f) and (g); (e), (f), and (g); and (d), (e), (f), and (g) depicted in FIGS. 3A(i) and 3A(ii).

In at least one embodiment, in an aspect, the compound having chemical formula (I) can be a compound having formula (B):

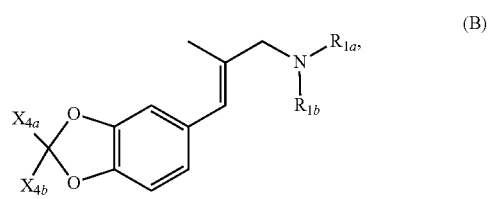

(B)

wherein in formula (B), $X_{4a}$ and $X_{4b}$ are, independently or simultaneously, a halogen atom or a hydrogen atom, wherein $R_{1a}$ and $R_{1b}$ are each independently selected from an alkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring, and the at least one chemical synthesis reaction is a reaction selected from (i); (f); (f) and (i); (e) and (f); (e), (f), and (i); (d), (e), and (f); and (d), (e), (f), and (i) depicted in FIG. 3A(i).

In at least one embodiment, in an aspect, the compound having chemical formula (I) can be a compound having formula (C):

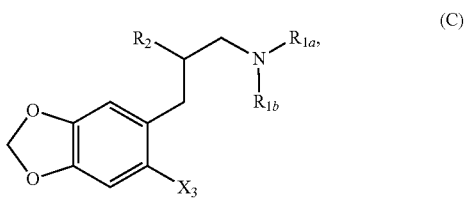

(C)

wherein $R_{1a}$ and $R_{1b}$ are each independently selected from an alkyl group, a hydroxylalkyl group, or a hydrogen atom, or $R_{1a}$ and $R_{1b}$ are joined together, along with the nitrogen atom to which they are attached, to form a 3-10-membered optionally substituted heterocyclic ring, wherein $R_2$ is selected from an alkyl group or a hydrogen atom, and wherein $X_3$ is an O-alkyl group, a halogen, or a hydrogen atom, and the at least one chemical synthesis reaction is a reaction selected from:

(i) {(h); (c) and (h); (b), (c), and (h); and (a), (b), (c), and (h) in FIGS. 3A(i) and 3A(ii)};

(ii) {(f); (d) and (f); (c2), (d), and (f); (c1), (d), and (f); (b), (c2), (d), and (f); (a), (b), (c2), (d), and (f); and (a), (c1), (d), and (f) in FIGS. 3B(i) and 3B(ii)};

(iii) {(e); (d) and (e); (c2), (d), and (e); (c1), (d), and (e); (b), (c2), (d), and (e); (a), (b), (c2), (d), and (e); and (a), (c1), (d), and (e) in FIGS. 3B(i) and 3B(ii)};

(iv) {(d); (c1) and (d); (c2) and (d); (b), (c2) and (d); and (a), (c1), and (d); and (a), (b), (c2) and (d) in FIGS. 3B(i) and 3B(ii)}; or (v) {(i); (c1) and (i); (c2) and (i); (b), (c2), and (i); and (a), (c1), and (i); and (a), (b), (c2) and (i)} in FIGS. 3B(i) and 3B(ii); or (vi) {(g); (d) and (g); (c2), (d), and (g); (c1), (d), and (g); (b), (c2), (d), and (g); (a), (b), (c2), (d), and (g); and (a), (c1), (d), and (g) in FIGS. 3B(i) and 3B(ii)}.

In at least one embodiment, in an aspect, the compound having chemical formula (I) can be a compound having formula (D):

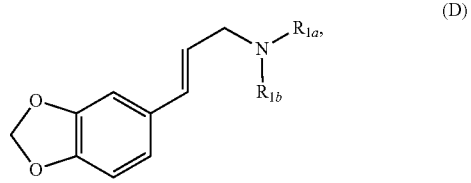

(D)

wherein $R_{1a}$ and $R_{1b}$ are each independently selected from an alkyl group, a hydrogen atom, or $R_{1a}$ and $R_{1b}$ are joined together, along with the nitrogen atom to which they are attached, to form a 3-10-membered optionally substituted heterocyclic ring, and the at least one chemical synthesis reaction is a reaction selected from (c); (b) and (c); and (a), (b), and (c) depicted in FIGS. 3A(i) and 3A(ii).

In at least one embodiment, in an aspect, the compound having chemical formula (I) can be a compound having formula (E):

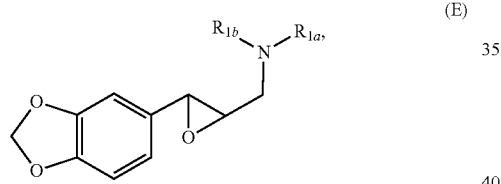

(E)

wherein $R_{1a}$ and $R_{1b}$ are each independently selected from an alkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring, and the at least one chemical synthesis reaction is a reaction selected from (b); and (a) and (b) depicted in FIG. 3C.

In at least one embodiment, in an aspect, the compound having chemical formula (I) can be a compound having formula (F):

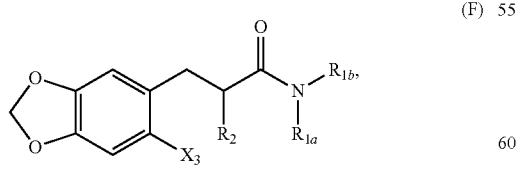

(F)

wherein $R_{1a}$ and $R_{1b}$ are each independently selected from a hydroxylalkyl group or a hydrogen atom, or $R_{1a}$ and $R_{1b}$ are joined together, along with the nitrogen atom to which they are attached, to form a 3-10-membered optionally substituted heterocyclic ring, and wherein $R_2$ is an alkyl group or a hydrogen atom, and $X_3$ is an O-alkyl group, a halogen, or a hydrogen atom, and the at least one chemical synthesis reaction is a reaction selected from: (c1); (c2); (b) and (c2); (a) and (c1); (a), (b), and (c2) depicted in FIGS. 3B(i) and 3B(ii).

In at least one embodiment, in an aspect, the compound having chemical formula (I) can be a compound having formula (G):

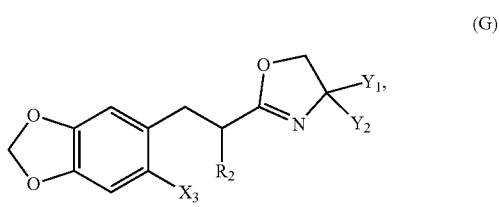

(G)

wherein $X_3$ is a hydrogen atom, a halogen atom, or an O-alkyl group, wherein $R_2$, $Y_1$ and $Y_2$ are each independently an alkyl group or a hydrogen atom, and the at least one chemical synthesis reaction is a reaction selected from {(h); (c1) and (h); (c2) and (h); (b), (c2), and (h); and (a), (c1), and (h); and (a), (b), (c2) and (h) in FIGS. 3B(i), 3B(ii), and 3B(iii).

In another aspect the present disclosure provides, in at least one embodiment, a use of a chemical compound having chemical formula (I) or (II):

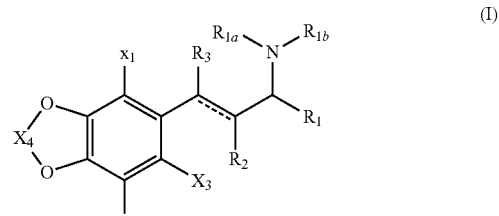

(I)

or

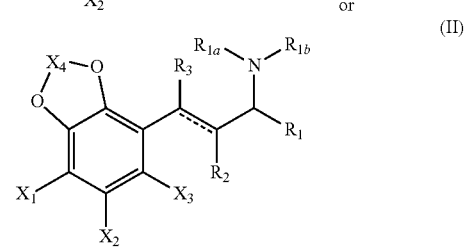

(II)

wherein, in chemical formula (I) or (II):

⚏ is a single or double bond;

$X_1$, $X_2$, and $X_3$ are independently selected from a hydrogen atom, O-alkyl, acyl, N-alkyl, OH, a halogen, or $NH_2$;

$X_4$ is an alkylene group or substituted alkylene group;

$R_1$ is a hydrogen, an alkyl group, or an oxo group, or $R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;

$R_{1a}$ and $R_{1b}$ are each independently selected from an alkyl group, a hydroxylalkyl group, an optionally substituted alkyl-aryl group, or a hydrogen atom, or R$_{1a}$ and R$_{1b}$ are joined together, along with the nitrogen atom to which they are attached, to form a 3-10-membered optionally substituted heterocyclic ring; and R$_2$ and R$_3$ are each independently selected from an alkyl group, O-alkyl group, a hydrogen atom, or R$_2$ and R$_3$ are joined together with an oxygen atom together with the carbon atoms to which they are attached to form an oxirane ring, in the manufacture of a pharmaceutical or recreational drug formulation.

In at least one embodiment, in an aspect, the manufacture can comprise formulating the chemical compound with an excipient, diluent, or carrier.

In another aspect the present disclosure provides, in at least one embodiment, a use of a having chemical formula (I) or (II):

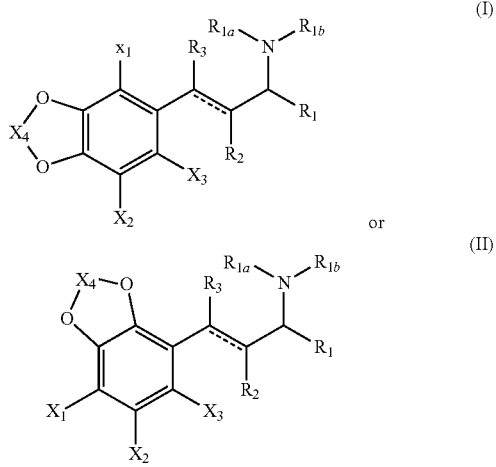

wherein, in chemical formula (I) or (II):

⚡ is a single or double bond;

X$_1$, X$_2$, and X$_3$ are independently selected from a hydrogen atom, O-alkyl, acyl, N-alkyl, OH, a halogen, or NH$_2$;

X$_4$ is an alkylene group or substituted alkylene group;

R$_1$ is a hydrogen, an alkyl group, or an oxo group, or R$_1$ is joined together with R$_{1b}$, together with the carbon atom to which R$_1$ is attached and the nitrogen atom to which R$_{1b}$ is attached, to form an optionally substituted saturated or unsaturated 3-10 membered heterocyclic ring, and when the heterocyclic ring is unsaturated, R$_{1a}$ is optionally absent;

R$_{1a}$ and R$_{1b}$ are each independently selected from an alkyl group, a hydroxylalkyl group, an optionally substituted alkyl-aryl group, or a hydrogen atom, or R$_{1a}$ and R$_{1b}$ are joined together, along with the nitrogen atom to which they are attached, to form a 3-10-membered optionally substituted heterocyclic ring; and R$_2$ and R$_3$ are each independently selected from an alkyl group, O-alkyl group, a hydrogen atom, or R$_2$ and R$_3$ are joined together with an oxygen atom together with the carbon atoms to which they are attached to form an oxirane ring, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

Figure 1:
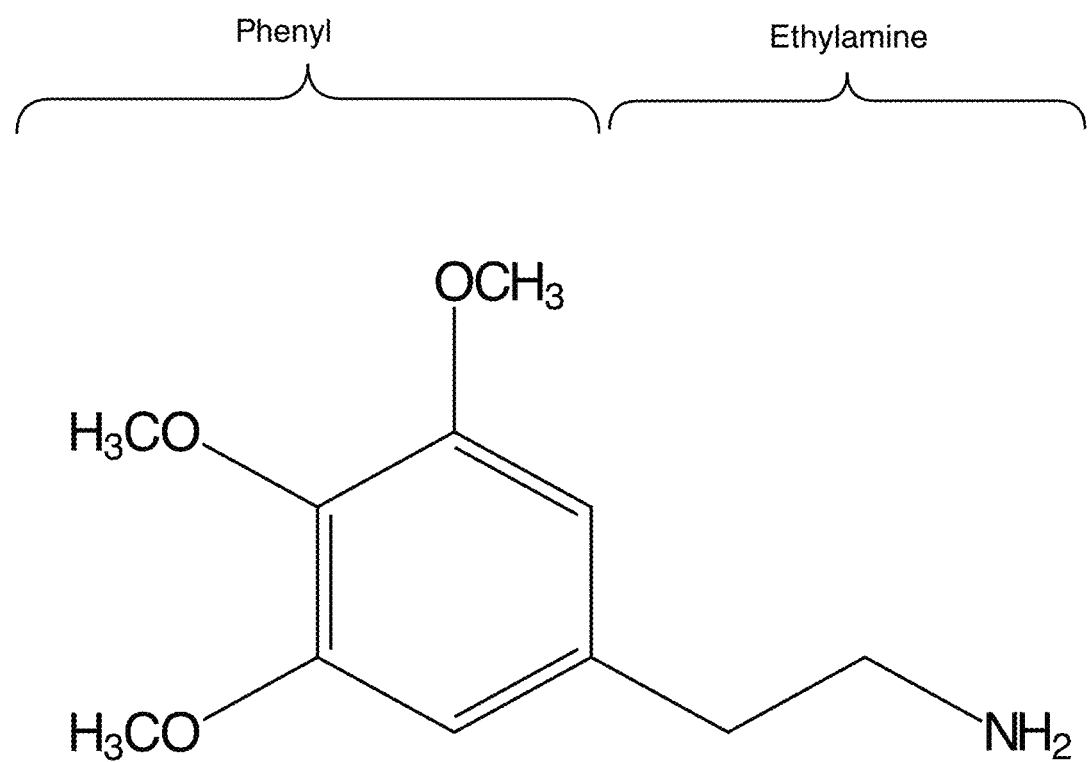
FIG. 1 depicts the chemical structure of mescaline, and identifies a phenyl portion, comprising a substituted phenyl group, and an ethylamine portion of the compound.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore, any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Definitions

The term "mescaline" refers to a chemical compound having the structure set forth in FIG. 1. It is noted that mescaline is also known in the art as 3,4,5 trimethoxyphenethylamine. It is further noted that mescaline includes a phenyl portion comprising a substituted phenyl group, and an ethylamine portion, as shown in FIG. 1.

Figure 2:
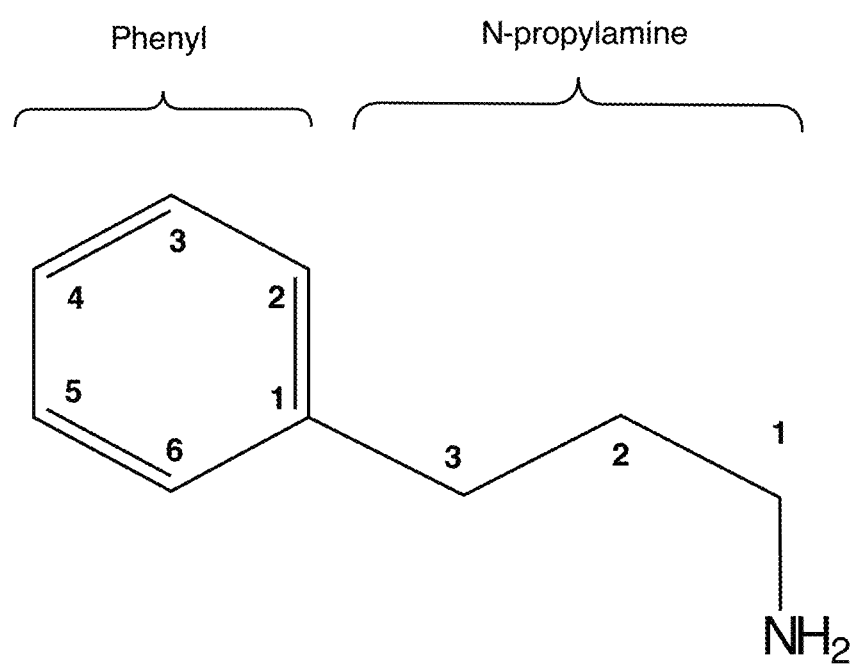
FIG. 2 depicts a certain prototype structure of mescaline derivative compounds. The prototype structure contains a phenyl portion, comprising a substituted phenyl group, and an N-propylamine portion, as indicated. Carbon atoms have been numbered C$_1$, C$_2$, C$_3$ etc. to indicate their position in the phenyl portion or N-propylamine portion, respectively. Thus, for example, it will be clear from FIG. 2 that the N-propylamine chain extends from the C$_1$ carbon of the phenyl group. Furthermore, it is noted that certain compounds may be named in accordance with the same. Thus, for example, the C$_1$ carbon atom of the N-propylamine chain is aminated, and the chain is referred to as N-propylamine. By way of another example, in 2,3 (1,3) dioxolanephenyl N-propylamine, phenyl portion carbon atoms C$_2$ and C$_3$, are each participating in the formation of a (1,3) dioxolane group (i.e., a pentane in which the carbons at positions 1 and 3 have been replaced with an oxygen atom). Similarly, in 3,4,5 trimethoxyphenethylamine (mescaline), phenyl portion carbon atoms C$_3$, C$_4$, and C$_5$ are each bonded to a methoxy group.

The term "mescaline derivative prototype structure" refers to the chemical structure shown in FIG. 2. The mescaline derivatives disclosed herein include the mescaline derivative prototype structure shown in FIG. 2, wherein various atoms may be substituted, as herein described. It is noted that the prototype structure comprises a phenyl portion and an N-propylamine (instead of an ethylamine portion as is the case for mescaline, see: FIG. 1). Furthermore, it is noted that specific carbon atoms in the mescaline derivative prototype structure are numbered. In this respect, it is noted that specific carbon atoms in the phenyl portion of the prototype structure are numbered separately from the carbon atoms in the N-propylamine portion. Reference may be made herein to these numbered carbons, for example, $C_1$ of the phenyl portion, $C_2$ of the phenyl portion, or $C_3$ of the N-propylamine portion, and so forth. It is noted that the N-propylamine chain extends from the $C_1$ carbon atom of the phenyl portion of the prototype structure. It is further noted that, in general terms, disclosed herein are mescaline derivatives in which: (i) adjacent carbon atoms $C_2$ and $C_3$ (formula ($I_a$) and formula ($I_b$)) or $C_3$ and $C_4$ (formula ($II_a$) and formula ($II_b$)) of the phenyl portion of the prototype structure participate in a fusion to a heterocycle, notably, in some embodiments, a 5-membered heterocycle, and notably, in some embodiments, a (1,3) dioxolane ring; and (ii) the N-propylamine chain extending from the $C_1$ atom of the phenyl portion of the prototype structure is, in example embodiments, a substituted N-propylamine chain, notably an N-propylamine chain which may possess a substituted $C_2$ and/or a substituted $C_3$ carbon atom (—$CHR_2$—$CHR_3$—) or (—$CR_2$=$CR_3$—), wherein $R_2$ and/or $R_3$ are a substituent. Thus, the herein disclosed mescaline derivatives can be said to be N-propylamine fused heterocyclic mescaline derivatives.

A straight bond, or a wavy or squiggly bond, drawn to a chiral atom, including, notably a chiral carbon atom, within a structural chemical formula indicates that the stereochemistry of the chiral atom is undefined. Examples of such chemical structural formulas are structural formulas (a), (b), and (c):

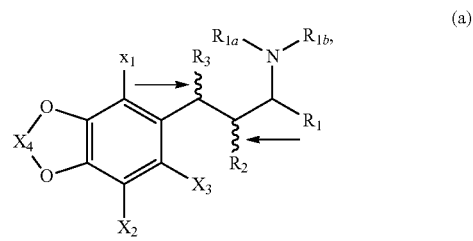

(a)

(b)

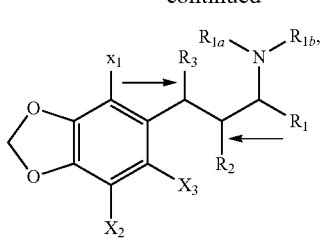

(c)

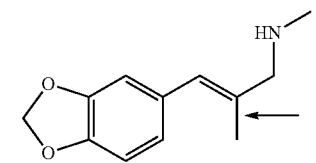

Thus, for example, a straight bond, or a wavy or squiggly bond, drawn to a chiral atom is intended to denote the S- or R-configuration, as well as mixtures thereof, in a single figure. When a straight bond, or a wavy or squiggly bond, are attached to a double bond moiety (such as —C═C—), included are the cis- or trans- (or (E)- or (Z)-) geometric isomers, or mixtures thereof.

The term "chiral carbon atom" as used herein refers to a carbon atom bonded to four different substituents.

The terms "stereoisomer" and "stereoisomeric compound", as used herein, are intended to refer to a chemical compound in reference to another chemical compound, wherein both compounds have the same chemical formula when the structural formula is denoted with straight bonds. However, when the structural formula of the two compounds is denoted with one or more wedge bonds ( , ) drawn to an atom, to thereby define the three dimensional configuration of the compounds, the compounds are three-dimensionally differently configured. In this respect, the wedge bonds can signify that stereoisomers of a compound exist. A pair of stereoisomers can include two compounds which are configured three-dimensionally such that they are mirror images of one another. Thus, for example, compounds (a(i)) and (a(ii)), when $R_2=R_1=H$ or when $R_2=H$ and $R_1$ is an oxo group, are stereoisomers which are mirror images of one another, (a(i))

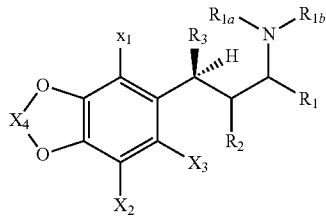

and (a(ii))

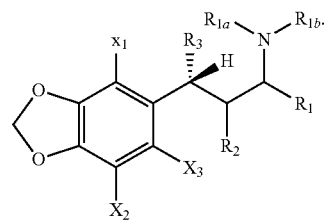

It is noted that stereoisomers may occur in mixtures containing varying relative amounts of the stereoisomers, including mixtures comprising equimolar, or approximately equimolar quantities of two stereoisomers, which may also referred to as "racemic mixtures".

The representation "  ", as used herein to depict chemical structures or formulas, refers to a chemical bond which may be either saturated or unsaturated.

The terms "hydroxy group", and "hydroxy", as used herein, refer to a molecule containing one atom of oxygen bonded to one atom of hydrogen, and having the chemical formula —OH. A hydroxy group through its oxygen atom may be chemically bonded to another entity.

The terms "amino" and "amino group", as used herein, refers to a molecule containing one atom of nitrogen bonded to hydrogen atoms and having the formula —NH$_2$. An amino group also may be protonated and having the formula —NH$_3^+$. In its protonated form the amino group may form an ammonium salt, for example, a chloride or sulfate ammonium salt, or an organic ammonium salt, all of which may be represented herein as NH$_3^+$Z$^-$. An amino group through its nitrogen atom may be chemically bonded to another entity. Furthermore, it is noted that an entity attached to an amino group may be referred to herein as an "aminated" entity, e.g., an aminated mescaline derivative is a mescaline derivative possessing an amino group.

The term "oxo group", as used herein, as used herein refers to the group ═O, and, for example, can be formed by replacing two hydrogens bonded to the same carbon atom with ═O.

The term "carbonyl group", as used herein, as used herein, refers to the group C═O, and can be formed by replacing two hydrogens bonded to the same carbon atom with ═O.

The term "oxirane", as used herein, refers to a three-membered oxygen containing heterocycle having the chemical formula:

$$\overset{O}{\underset{}{\triangle}}.$$

The terms "halogen", "halogen group", "halo-" and "halogenated", as used herein, refer to the class of chemical elements consisting of fluorine (F), chlorine (Cl), bromine (Br), and iodine (I). Accordingly, halogenated compounds can refer to "fluorinated", "chlorinated", "brominated", or "iodinated" compounds.

The term "alkyl group", as used herein, refers to a hydrocarbon group arranged in a chain having the chemical formula —C$_n$H$_{2n+1}$. Alkyl groups include, without limitation, methyl groups (—CH$_3$), ethyl groups (—C$_2$H$_5$), propyl groups (—C$_3$H$_7$) and butyl groups (—C$_4$H$_9$). The alkyl groups (including O-alkyl, and the alkyl groups present in acyl and O-acyl) in any of the embodiments of the disclosure is C$_1$-C$_{20}$-alkyl. In another embodiment, the alkyl group is C$_1$-C$_{10}$-alkyl. In another embodiment, the alkyl group is C$_1$-C$_6$-alkyl. In another embodiment, the alkyl group is methyl, ethyl, propyl, butyl or pentyl.

The terms "O-alkyl group", and "alkoxy group", as used herein interchangeably, refer to a hydrocarbon group arranged in a chain having the chemical formula —O—C$_n$H$_{2n+1}$. O-alkyl groups include, without limitation, O-methyl groups (—O—CH$_3$) (i.e., methoxy), O-ethyl groups (—O—C$_2$H$_5$) (i.e., ethoxy), O-propyl groups (—O—C$_3$H$_7$) (i.e., propoxy) and O-butyl groups (—O—C$_4$H$_9$) (i.e., butoxy).

The terms "N-alkyl group", as used herein, refers to a hydrocarbon group arranged in a chain having the chemical formula —N—$C_nH_{2n+1}$. N-alkyl groups include, without limitation, N-methyl groups (—N—$CH_3$), N-ethyl groups (—N—$C_2H_5$), N-propyl groups (—N—$C_3H_7$), and N-butyl groups (—N—$C_4H_9$).

The term "hydroxylalkyl", as used herein, refers to a hydrocarbon group arranged in a straight chain substituted with at least one hydroxy group, including a straight chain having the chemical formula —$C_nH_{2n}OH$, or a hydrocarbon group arranged in branched chain substituted with at least one hydroxy group. In the noted chemical formula, depending on the carbon chain, length specific hydroxylalkyl groups may be termed a methanol group (n=1) or hydroxymethyl, an ethanol group (n=2) or hydroxyethyl, a propanol group (n=3) or hydroxypropyl, a butanol group (n=4) or hydroxybutyl etc. A further example hydroxylalkyl includes a hydrocarbon group having the formula:

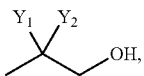

wherein $Y_1$ and $Y_2$ are each simultaneously or independently a hydrogen atom, or an alkyl group (e.g., —$CH_3$, —$CH_2$—$CH_3$).

The term "acyl group", as used herein, refers to a carbon atom double bonded to an oxygen and single bonded to an alkyl group. The carbon atom further can be bonded to another entity. An acyl group can be described by the chemical formula: —C(=O)—$C_nH_{2n+1}$ or e.g., ($C_1$-$C_6$)-acyl, ($C_1$-$C_3$)-acyl etc. Furthermore, depending on the carbon chain, length specific acyl groups may be termed a formyl group (n=0), an acetyl group (n=1), a propionyl group (n=2), a butyryl group (n=3), a pentanoyl group (n=4), etc.

The term "O-acyl group", as used herein, refers to an acyl group in which the carbon atom is single bonded to an additional oxygen atom. The additional oxygen atom can be bonded to another entity. An O-acyl group can be described by the chemical formula: —O—C(=O)—$C_nH_{2n+1}$ or e.g., —O—($C_1$-$C_6$)-acyl, —O—($C_1$-$C_3$)-acyl etc. Furthermore, depending on the carbon chain, length specific O-acyl groups may be termed an O-formyl group (n=0), an O-acetyl group (n=1), an O-propionyl group (n=2), an O-butyryl group (n=3), an O-pentanoyl group (n=4) etc.

The term "alkylene", as used herein, refers to a divalent alkyl group.

The term "hetero", as used herein (e.g., "heterocycle", "heterocyclic", "heterocyclic group"), refers to a saturated or partially saturated or aromatic cyclic group, in which one or two ring atoms are a heteroatom selected from N, O, or S, the remaining ring atoms being C. Included are, for example, ($C_3$-$C_{20}$), ($C_3$-$C_{10}$), and ($C_3$-$C_6$) cyclic groups comprising one or two hetero atoms selected from O, S, or N.

The term "aryl group", as used herein, refers to an aromatic ring compound in which at least one hydrogen atom has been removed from the aromatic ring to permit the bonding of a carbon atom in the aromatic ring to another entity. The aryl groups can optionally be a substituted $C_6$-$C_{14}$-aryl. The aryl group can further optionally be substituted $C_6$-$C_{10}$-aryl, or phenyl. Further aryl groups include phenyl, naphthyl, tetrahydronaphthyl, phenanthrenyl, biphenylenyl, indanyl, or indenyl and the like.

The term "alkyl-aryl", as used herein, refers to an alkylene group substituted with an aryl group.

The term "receptor", as used herein, refers to a protein present on the surface of a cell, or in a cell not associated with a cellular surface (e.g., a soluble receptor) capable of mediating signaling to and/or from the cell, or within the cell and thereby affect cellular physiology. Receptors may be classified in classes, such as the G-protein coupled receptors ("GPCRs"), families, such as 5-HT receptors, and sub-families such as 5-$HT_{1A}$ receptors, 5-$HT_{2A}$ receptors, and 5-$HT_{2B}$ receptors, and so on. In this respect, "signaling" refers to a response in the form of a series of chemical reactions which can occur when a molecule, including, for example, the fused heterocyclic mescaline derivatives disclosed herein, interacts with a receptor. Signaling generally proceeds across a cellular membrane and/or within a cell, to reach a target molecule or chemical reaction, and results in a modulation in cellular physiology. Thus, signaling can be thought of as a transduction process by which a molecule interacting with a receptor can modulate cellular physiology, and, furthermore, signaling can be a process by which molecules inside a cell can be modulated by molecules outside a cell. Signaling and interactions between molecules and receptors, including for example, affinity, binding efficiency, and kinetics, can be evaluated through a variety of assays, including, for example, assays known as receptor binding assays (for example, radioligand binding assays, such as e.g., [$^3$H]ketanserin assays may be used to evaluate receptor 5-$HT_{2A}$ receptor activity), competition assays, and saturation binding assays, and the like.

The term "G-protein coupled receptor" or "GPCR", as used herein, refers to a class of evolutionarily related transmembrane receptors capable of interacting with a class of proteins known as G-proteins (guanine nucleotide binding proteins). GPCRs can mediate cellular responses to external stimuli (Weis and Kobilka, 2018, Annual Review of Biochemistry 87: 897-919) and can be activated by interacting with a ligand, including neurotransmitters, such as serotonin or dopamine, for example, which, can then initiate an interaction of the receptor with a G-protein and can elicit dissociation of the G-protein into α and βγ subunits. In turn, these α and βγ subunits can mediate further downstream signaling. GPCRs can also activate other signaling pathways, for example, through arrestin proteins and kinases. Certain ligands can preferentially activate a subset of all GPCR signaling pathways. Signaling pathways downstream of a GPCR can mediate therapeutic efficacy, or can cause drug adverse effects (Bock and Bermudez, 2021, FEBS Journal 288: 2513-2528).

The term "5-HT receptor", as used herein, refers to a family of GPCRs receptors found in the central and peripheral nervous system and include sub-families, such as, 5-$HT_{1A}$ receptors, 5-$HT_{2A}$ receptors, and 5-$HT_{2B}$ receptors. 5-HT receptors can mediate signaling through specific G-proteins, including notably $G\alpha_i$, $G\alpha_{q/11}$, and $G\alpha_s$ and can be involved in the control of multiple physiological processes including cognition, mood, and modulation of sleep-wake cycles, for example (McCorvy and Roth, 2015, Pharmacology and Therapeutics 150: 129-142). 5-HT receptors can further mediate signaling through arrestin as well as G-protein independent signaling pathways. 5-HT-receptors are implicated in multiple brain neurological disorders including migraine headaches, and neuropsychiatric disorders, such as schizophrenia and depression, for example.

The term "5-$HT_{1A}$ receptor", as used herein, refers to a sub-family of a family of receptors for the neurotransmitter and peripheral signal mediator serotonin. 5-$HT_{1A}$ receptors can mediate a plurality of central and peripheral physiologic functions of serotonin. Ligand activity at $5\text{-}HT_{1A}$ is generally not associated with hallucination, although many hallucinogenic compounds are known to modulate $5\text{-}HT_{1A}$ receptors to impart physiological responses (Inserra et al., 2020, Pharmacol. Rev 73: 202). $5\text{-}HT_{1A}$ receptors are implicated in various brain neurological disorders, including depression and anxiety, schizophrenia, and Parkinson's disease (Behav. Pharm. 2015, 26:45-58).

The term "$5\text{-}HT_{2A}$ receptor", as used herein, refers to a sub-family of a family of receptors for the neurotransmitter and peripheral signal mediator serotonin. $5\text{-}HT_{2A}$ receptors can mediate a plurality of central and peripheral physiologic functions of serotonin. Central nervous system effects can include mediation of hallucinogenic effects of hallucinogenic compounds. $5\text{-}HT_{2A}$ receptors are implicated in various brain neurological disorders (Nat. Rev. Drug Discov. 2022, 21:463-473; Science 2022, 375:403-411).

The term "$5\text{-}HT_{2B}$ receptor" (also referred to herein as "HT2B" and "HTR2B"), as used herein, refers to a sub-family of a family of receptors for the neurotransmitter and peripheral signal mediator serotonin. $5\text{-}HT_{2B}$ receptors can mediate a plurality of central and peripheral physiologic functions of serotonin. Central nervous system effects can include mediation of hallucinogenic effects of hallucinogenic compounds. $5\text{-}HT_{2B}$ receptors are implicated in various brain neurological disorders, including schizophrenia (Pharmacol. Ther. 2018, 181:143-155) and migraine (Cephalalgia 2017, 37:365-371).

The term "$5\text{-}HT_{2C}$ receptor" (also referred to herein as "HT2C" and "HTR2C"), as used herein, refers to a sub-family of a family of receptors for the neurotransmitter and peripheral signal mediator serotonin. Antagonism of $5\text{-}HT_{2C}$ receptors by drugs such as agomelatine can increase availability of norepinephrine and dopamine in the prefrontal cortex, and can lead to antidepressant and nootropic effects (Savino et al., 2023, Brain Science 13: 734). Further, $5\text{-}HT_{2C}$ receptors can play a role in food intake and body weight control (Przegaliński et al., 2023, Nutrients 15:1449).

The term "$5\text{-}HT_7$ receptor" (also referred to herein as "HT7" and "HTR7"), as used herein, refers to a sub-family of a family of receptors for the neurotransmitter and peripheral signal mediator serotonin. $5\text{-}HT_{1D}$ receptors are implicated in various brain neurological disorders, including Alzheimer's, dementia, and associated depressive disorders (Quintero-Villegas and Valdes-Ferrer, 2022, Molecular Medicine 28: 70).

The term "$\alpha_{2A}$ receptor" (also referred to herein as "$\alpha$-2A", and "alpha2A") as used herein, refers to a sub-family of a family of receptors for catecholamine neurotransmitters and signal mediators such as norepinephrine (noradrenaline) and epinephrine (adrenaline). $\alpha$-2A receptors are implicated in various brain neurological disorders, including schizophrenia, bipolar disorders, and post-traumatic stress disorder (PTSD) (Saggu et al., 2023, Molecular Psychiatry 28: 588-600).

The term "$MT_1$ receptor" (also referred to herein as "MT1"), used herein, refers to a sub-family of a family of receptors for the neural transmitter and signal mediator melatonin. $MT_1$ receptors are implicated in various brain neurological disorders, including sleep disorders and depression (Boiko et al., 2022, Neurochemical Research 47: 2909-2924).

The term "$D_3$ receptor" (also referred to herein as "D3"), used herein, refers to a sub-family of a family of receptors for the neural transmitter and signal mediator dopamine. $D_3$ receptors are implicated in various brain neurological disorders, including schizophrenia, drug addiction, and Parkinson's disease (Kim, 2023, International Journal of Molecular Sciences 24: 6742).

The term "DAT", as used herein, refers to a transmembrane transport protein also known as "dopamine active transporter", which is involved of transporting dopamine into the cytosol. DAT is implicated in various brain neurological disorders, notably dopamine related disorders such as attention deficit hyperactivity disorder (ADHD), bipolar disorder, and clinical depression, anxiety (Am. J. Med. Genet. B Neuropsychiatr. Genet. 2018, 177:211-231).

The term "NET", as used herein, refers to a transmembrane transport protein also known as "norepinephrine transporter" or "noradrenaline transporter" or "NAT" which is involved in $Na^+/Cl^-$ dependent re-uptake of extracellular norepinephrine or noradrenaline. NET is implicated in various brain neurological disorders, including attention deficit hyperactivity disorder (ADHD) and clinical depression (Neurosci. Biobehav. Rev, 2013, 37:1786-800).

The term "SERT", as used herein, refers to a transmembrane transport protein also known as "serotonin transporter" which is involved in neuronal serotonin transport, notably from the synaptic cleft back to the presynaptic neuron, thereby terminating the action of serotonin. SERT is implicated in various brain neurological disorders, including anxiety and depression (Pharmacol. Rep. 2018, 70:37-46).

The term "modulating receptors", as used herein, refers to the ability of a compound disclosed herein to alter the function of receptors. A receptor modulator may activate the activity of a receptor or inhibit the activity of a receptor depending on the concentration of the compound exposed to the receptor. Such activation or inhibition may be contingent on the occurrence of a specific event, such as activation of a signal transduction pathway, and/or maybe manifest only in particular cell types. The term "modulating receptors," also refers to altering the function of a receptor by increasing or decreasing the probability that a complex forms between a receptor and a natural binding partner to form a multimer. A receptor modulator may increase the probability that such a complex forms between the receptor and the natural binding partner, may increase or decrease the probability that a complex forms between the receptor and the natural binding partner depending on the concentration of the compound exposed to the receptor, and or may decrease the probability that a complex forms between the receptor and the natural binding partner. It is further noted that the fused heterocyclic mescaline derivatives of the present disclosure may alter the function of a receptor by acting as an agonist or antagonist of the receptor, and that fused heterocyclic mescaline derivatives according to the present disclosure may alter the function of a receptor by directly interacting therewith or binding thereto, or by indirectly interacting therewith through one or more other molecular entities. In general, the receptor may be any receptor, including any receptor set forth herein, such as, any of a $5\text{-}HT_{1A}$, $5\text{-}HT_{2A}$, a $5\text{-}HT_{2B}$, $5\text{-}HT_{2C}$, $5\text{-}HT_7$, $\alpha_{2A}$, $MT_1$ receptor, for example. Accordingly, it will be clear, that in order to refer modulating specific receptors, terms such as "modulating $5\text{-}HT_{1A}$ receptors", "modulating $5\text{-}HT_{2A}$ receptors", "modulating $5\text{-}HT_{2B}$ receptors", and so forth, may be used herein.

The term "receptor-mediated disorder", as used herein, refers to a disorder that is characterized by abnormal receptor activity. A receptor-mediated disorder may be completely or partially mediated by modulating a receptor. In particular, a receptor-mediated disorder is one in which modulation of the receptor results in some effect on an underlying disorder e.g., administration of a receptor modulator results in some improvement in at least some of the subjects being treated. In general, the receptor may be any receptor, including any receptor set forth herein, such as any of a $5\text{-HT}_{1A}$, $5\text{-HT}_{2A}$, a $5\text{-HT}_{2B}$, $5\text{-HT}_{2C}$, $5\text{-HT}_7$, $\alpha_{2A}$, $D_3$, or a $MT_1$ receptor, for example. Accordingly, it will be clear, that in order to refer specific receptor-mediated disorders, terms such as "$5\text{-HT}_{1A}$ receptor-mediated disorder", "$5\text{-HT}_{2A}$ receptor-mediated disorder", "$5\text{-HT}_{2B}$ receptor-mediated disorder", and so forth, may be used.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject, and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The term "substantially free", as used herein to describe a composition, references the substantial absence of a second compound in a composition comprising a first compound. Preferably the composition containing the first compound contains less than 5%, less than 2.5%, less than 1%, less than 0.5%, less than 0.1%, or less than 0.01% by mole percent of the second compound.

The terms "substantially pure" and "isolated", as may be used interchangeably herein describe a compound, e.g., a mescaline derivative, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

General Implementation

As hereinbefore mentioned, the present disclosure relates to mescaline derivatives. In particular, the present disclosure provides novel heterocyclic mescaline derivatives, wherein the phenyl portion participates in the formation of a heterocyclic ring structure, including, in example embodiments, a dioxolane ring, fused to the phenyl portion. Thus, the compounds of the present disclosure can be said to be fused heterocyclic mescaline derivatives. Furthermore, the mescaline derivatives include an N-propylamine chain (instead of an ethylamine chain, as is the case for mescaline). The N-propylamine chain can contain various substituent groups, including, notably $C_2$ and/or $C_3$ substituent groups. In addition, the amine group in the N-propylamine chain can be substituted. Thus, the herein disclosed mescaline derivatives can be said to be N-propylamine fused heterocyclic mescaline derivatives. In general, the herein provided novel compounds exhibit functional properties which deviate from the functional properties of mescaline. Thus, for example, the mescaline derivatives of the present disclosure, can exhibit pharmacological properties which deviate from mescaline. Furthermore, the mescaline derivatives may exhibit physico-chemical properties which differ from mescaline. Thus, for example, the fused heterocyclic mescaline derivatives may exhibit superior solubility in a solvent, for example, an aqueous solvent. The fused heterocyclic mescaline derivatives in this respect are useful in the formulation of pharmaceutical and recreational drug formulations. In one embodiment, the fused heterocyclic mescaline derivatives of the present disclosure can conveniently be chemically synthesized. The practice of this method avoids the extraction of mescaline from cactus plants and the performance of subsequent chemical reactions to achieve the fused heterocyclic mescaline derivatives. Furthermore, the growth of cactus plants can be avoided thus limiting the dependence on climate and weather, and potential legal and social challenges associated with the cultivation of cactus plants containing psychoactive compounds. The method can efficiently yield substantial quantities of the fused heterocyclic mescaline derivatives.

In what follows selected embodiments are described with reference to the drawings.

Initially example fused heterocyclic mescaline derivatives will be described. Thereafter example methods of using and making the fused heterocyclic mescaline derivatives will be described.

Accordingly, in one aspect the present disclosure provides derivatives of a compound known as mescaline of which the chemical structure is shown in FIG. 1. The derivatives herein provided are, in particular, fused heterocyclic derivatives of mescaline. It is noted that in this respect, that the term "fused heterocyclic", refers to a derivative wherein a heterocycle is bonded to two adjacent carbon atoms present in the phenyl ring of mescaline. Similarly, the term "fused dioxolane", refers to a derivative wherein a dioxolane is bonded to two adjacent carbon atoms present in the phenyl ring of mescaline. Furthermore, the derivatives are N-propylamine mescaline derivatives. In this respect, referring to FIG. 2, "N-propylamine" refers to a mescaline derivative comprising an N-propylamine chain wherein, in particular, in example embodiments specifically the $C_2$ and/or $C_3$ atom of the N-propylamine chain are substituted with one or more substituents.

Thus, in one aspect, the present disclosure provides, in accordance with the teachings herein, in at least one embodiment, a chemical compound having chemical formula (I) or (II):

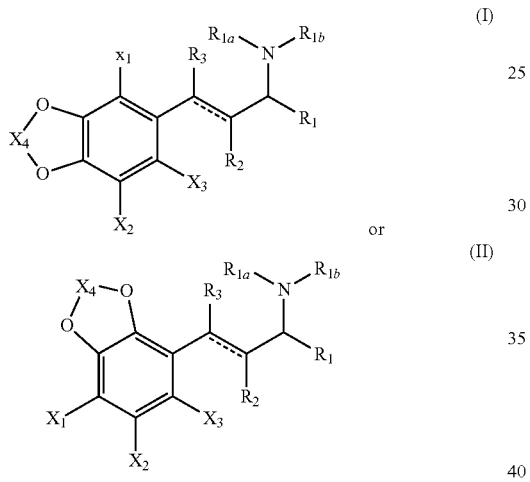

wherein, in chemical formula (I) or (II):

- is a single or double bond;
- $X_1$, $X_2$, and $X_3$ are independently selected from a hydrogen atom, O-alkyl, acyl, N-alkyl, OH, a halogen, or $NH_2$;
- $X_4$ is an alkylene group or substituted alkylene group;
- $R_1$ is a hydrogen, an alkyl group, or an oxo group, or $R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;
- $R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and
- $R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring.

In one embodiment, the chemical compound having formula (I) can be a compound having formula ($I_a$) or ($I_b$), and the compound having formula (II) can a compound having formula ($II_a$) or ($II_b$):

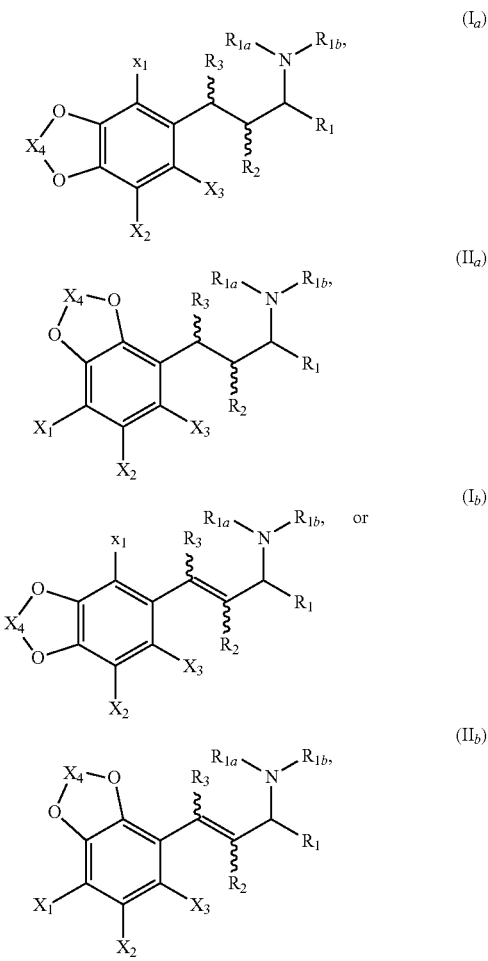

wherein, in chemical formula ($I_a$), ($I_b$), ($II_a$), or ($II_b$):

- $X_1$, $X_2$, and $X_3$ are independently selected from a hydrogen atom, O-alkyl, acyl, N-alkyl, OH, a halogen, or $NH_2$;
- $X_4$ is an alkylene group or substituted alkylene group;
- $R_1$ is a hydrogen, an alkyl group, or an oxo group, or $R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;
- $R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and
- $R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring.

Thus, referring to formula ($I_a$), ($I_b$), ($II_a$), and ($II_b$), $X_1$, $X_2$, and $X_3$ can be independently selected from a hydrogen atom, O-alkyl, N-alkyl, acyl, OH, a halogen, or $NH_2$. In example embodiments, $X_1$, $X_2$, and $X_3$ can each independently be selected from a hydrogen atom, O-alkyl (e.g., O—($C_1$-$C_{10}$)-alkyl, O—($C_1$-$C_6$)-alkyl, or O—($C_1$-$C_3$)-alkyl (methoxy, ethoxy, propoxy)), acyl (e.g., —(C═O)($C_1$-$C_6$)-acyl, —(C═O)($C_1$-$C_3$)-acyl) N-alkyl (e.g., N—($C_1$-$C_{10}$)-alkyl, N—($C_1$-$C_6$)-alkyl, or N—($C_1$-$C_3$)-alkyl), OH, halogen (C, F, Cl, I), or $NH_2$. In further example embodiments, all three of $X_1$, $X_2$, and $X_3$ can be identical substituents. In further example embodiments, all three of $X_1$, $X_2$, and $X_3$ can be identical O-alkyl groups (e.g., methoxy groups, ethoxy groups), non-identical O-alkyl groups, or partially identical O-alkyl groups (i.e., 2 identical O-alkyl groups, 1 non-identical O-alkyl group); identical N-alkyl groups, non-identical N-alkyl groups, or partially identical N-alkyl groups (i.e., 2 identical N-alkyl groups, 1 non-identical N-alkyl group); identical acyl groups, non-identical acyl groups, or partially identical acyl groups (i.e., 2 identical acyl groups, 1 non-identical acyl group); identical; or identical, non-identical or partially identical halogens (i.e., 2 identical halogens, 1 non-identical halogen). In further example embodiments, two of $X_1$, $X_2$, and $X_3$ can be identical substituents. In yet further example embodiments, all three of $X_1$, $X_2$, and $X_3$ can be non-identical substituents.

Turning to $X_4$, and referring further to formula ($I_a$), ($I_b$), ($II_a$), and ($II_b$), $X_4$ can be an alkylene group or substituted alkylene group. In an example embodiment, $X_4$ can be a non-substituted alkylene, including for example a ($C_1$-$C_{10}$)-alkylene, ($C_1$-$C_6$)-alkylene, or a ($C_1$-$C_3$)-alkylene (methylene (—$CH_2$—), ethylene (—$CH_2CH_2$—), propylene (—$CH_2CH_2CH_2$—)).

In an example embodiment, $X_4$ can be a substituted alkylene, including, for example, a ($C_1$-$C_{10}$) substituted alkylene, ($C_1$-$C_6$) substituted alkylene or a ($C_1$-$C_3$) substituted alkylene (substituted methylene (e.g., —CHR—, wherein R is a substituent), substituted ethylene (e.g., —CHR$CH_2$—, wherein R is a substituent), substituted propylene (e.g., —$CH_2$CHR$CH_2$—, wherein R is a substituent). Substituents can, for example, be selected from an oxo group (forming a carbonyl), hydroxy, halogen (F, Cl, Br, I), O-alkyl (e.g., O—($C_1$-$C_{10}$)-alkyl, O—($C_1$-$C_6$)-alkyl, or —O—($C_1$-$C_3$)-alkyl), N-alkyl (e.g., N—($C_1$-$C_{10}$)-alkyl, N—($C_1$-$C_6$)-alkyl, or N—($C_1$-$C_3$)-alkyl), acyl (e.g., ($C_1$-$C_{10}$)-acyl, ($C_1$-$C_6$)-acyl, or ($C_1$-$C_3$)-acyl), O-acyl (e.g., O—($C_1$-$C_{10}$)-acyl, O—($C_1$-$C_6$)-acyl, or O—($C_1$-$C_3$)-acyl) aryl (e.g., $C_6$-$C_{10}$ aryl, e.g., phenyl, naphthyl), and alkyl-aryl group (e.g., ($C_1$-$C_{10}$)-alkyl-aryl, ($C_1$-$C_6$)-alkyl-aryl, or ($C_1$-$C_3$)-alkyl-aryl). Further included are singly and multiply substituted alkylenes. Multiply substituted alkylenes include substitutions of the same alkylene carbon atom (thus a halogen substituent may be e.g., —$CH_2CF_2$— or —$CF_2$—) or substitutions of different carbon atoms (e.g., —CHF—CHF—).

In an example embodiment, $X_4$ can be a non-substituted alkylene, notably a (methylene (—$CH_2$—)), and the compound having chemical formula ($I_a$), ($I_b$), ($II_a$), and ($II_b$), can have a chemical formula ($I_c$), ($I_d$), ($II_c$), and ($II_d$):

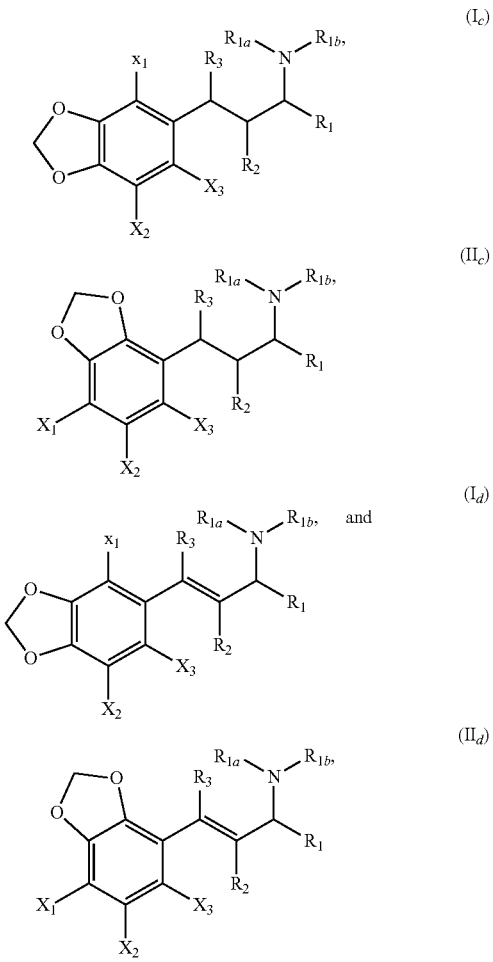

respectively.

As herein before noted, the current disclosure includes, in an aspect, in particular, mescaline derivatives including a substituted N-propylamine chain, notably in example embodiments, an N-propylamine chain possessing a substituted $C_2$ and/or a substituted $C_3$ carbon atom (—CHR$_2$—CHR$_3$—) (formula ($I_a$), ($II_a$), ($I_c$), and ($II_c$) or (—CR$_2$═CR$_3$—) (formula ($I_b$), ($II_b$), ($I_d$) and ($II_d$)), wherein $R_2$ and/or $R_3$ are a substituent.

Next, further example embodiments of mescaline derivatives including a chain will be described with respect to example selections of $R_2$ and $R_3$ substituents included in the N-propylamine chain. Referring to formula ($I_a$), ($I_b$), ($II_a$), and ($II_b$), $R_2$ and $R_3$ can each independently be selected from an alkyl group, O-alkyl group, or a hydrogen atom. Furthermore, referring to formula ($I_a$), ($I_b$), ($II_a$), and ($II_b$), as well as to formula ($I_c$), ($I_d$), ($II_c$) and ($II_d$), it is noted that in particular example embodiments, $X_1$, $X_2$, $X_3$ can each be selected to be H, as herein illustrated by example compounds A(I)-C(III); C(VI)-C(XII); D(I)-F(III), and G(I)-G(IV). These example embodiments, are in particular, but without limitation, intended to be included in conjunction with the hereinafter described example embodiments with respect to $R_2$ and $R_3$.

Thus, for example, referring to formula ($I_a$), ($I_b$), ($II_a$), ($II_b$), ($I_c$), ($I_d$), ($II_c$), and ($II_d$), in an example embodiment, $R_2$ and $R_3$ can each independently be selected from an alkyl group, O-alkyl group, or a hydrogen atom.

Continuing to refer to formula ($I_a$), ($I_b$), ($II_a$), ($II_b$), ($I_c$), ($I_d$), ($II_c$), and ($II_d$), in an example embodiment, $R_2$ and $R_3$ can each be a ($C_1$-$C_6$)-alkyl group, ($C_1$-$C_3$)-alkyl group, or a methyl group.

Continuing to refer to formula ($I_a$), ($I_b$), ($II_a$), ($II_b$), ($I_c$), ($I_d$), ($II_c$), and ($II_d$), in an example embodiment, $R_2$ can be a ($C_1$-$C_6$)-alkyl group, ($C_1$-$C_3$)-alkyl group, or a methyl group, and $R_3$ can be a hydrogen atom.

Continuing to refer to formula ($I_a$), ($I_b$), ($II_a$), ($II_b$), ($I_c$), ($I_d$), ($II_c$), and ($II_d$), in an example embodiment, $R_3$ can be a ($C_1$-$C_6$)-alkyl group, ($C_1$-$C_3$)-alkyl group, or a methyl group, and $R_2$ can be a hydrogen atom.

Continuing to refer to formula ($I_a$), ($I_b$), ($II_a$), ($II_b$), ($I_c$), ($I_d$), ($II_c$), and ($II_d$), in an example embodiment, $R_2$ and $R_3$ can each be a hydrogen atom.

Continuing to refer to formula ($I_a$), ($I_b$), ($II_a$), ($II_b$), ($I_c$), ($I_d$), ($II_c$), and ($II_d$), in an example embodiment, $R_2$ can be a ($C_1$-$C_6$)—O-alkyl group, ($C_1$-$C_3$)—O-alkyl group, or a methoxy group, and $R_3$ can be a hydrogen atom.

Continuing to refer to formula ($I_a$), ($I_b$), ($II_a$), ($II_b$), ($I_c$), ($I_d$), ($II_c$), and ($II_d$), in an example embodiment, $R_3$ can be a ($C_1$-$C_6$)—O-alkyl group, ($C_1$-$C_3$)—O-alkyl group, or a methoxy group, and $R_2$ can be a hydrogen atom.

Continuing to refer to formula ($I_a$), ($I_b$), ($II_a$), ($II_b$), ($I_c$), ($I_d$), ($II_c$), and ($II_d$), in an example embodiment, $R_2$ and $R_3$ can be a methoxy group.

Referring to formula ($I_a$), ($II_a$), ($I_c$), and ($II_c$), in an example embodiment, $R_2$ and $R_3$ can be joined together along with an oxygen atom to form an oxirane.

Referring again to formula ($I_a$), ($I_b$), ($II_a$), ($II_b$), ($I_c$), ($I_d$), ($II_b$), and ($II_d$), in an example embodiment $R_1$ can be a hydrogen, an alkyl group, including a ($C_1$-$C_6$) alkyl group, ($C_1$-$C_3$) alkyl group, or a methyl group, or $R_1$ can be an oxo group, or continuing to refer to formula ($I_a$), ($I_b$), ($II_a$), ($II_b$), ($I_c$), ($I_d$), ($II_c$), and ($II_d$), in another example embodiment, $R_1$ can be joined together with $R_{1b}$, together with the carbon atom to which $R_1$ is attached and the nitrogen atom to which $R_{1b}$ is attached, to form a 3-10 membered heterocyclic ring, for example, a 5-membered ring or a 6-membered ring. Furthermore, the heterocyclic ring can be optionally substituted or saturated or unsaturated, and furthermore, when the heterocyclic ring is unsaturated, $R_{1a}$ can optionally be absent.

Referring again to formula ($I_a$), ($I_b$), ($II_a$), ($II_b$), ($I_c$), ($I_d$), ($II_c$), and ($II_d$), in an example embodiment, $R_{1a}$ can be a hydrogen atom and $R_{1b}$ can be a ($C_1$-$C_6$)-alkyl group.

Continuing to refer to formula ($I_a$), ($I_b$), ($II_a$), ($II_b$), ($I_c$), ($I_d$), ($II_c$), and ($II_d$), in an example embodiment, $R_{1a}$ and $R_{1b}$ can each be a ($C_1$-$C_6$)-alkyl group or a ($C_1$-$C_3$)-alkyl group.

Continuing to refer to formula ($I_a$), ($I_b$), ($II_a$), ($II_b$), ($I_c$), ($I_d$), ($II_c$), and ($II_d$), in an example embodiment, $R_{1a}$ can be a hydrogen atom and $R_{1b}$ can be a hydroxylalkyl group, for example a hydroxyl-($C_1$-$C_6$)-alkyl group, or hydroxyl-($C_1$-$C_3$)-alkyl group, or —$CH_2$—$CH_2$—$CH_2OH$, —$CH_2$—$CH_2OH$, or —$CH_2OH$, or, in other embodiments, a hydroxylalkyl group having the formula:

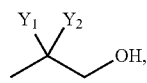

wherein $Y_1$ and $Y_2$ are each simultaneously or independently a hydrogen atom, or an alkyl group (e.g., —$CH_3$, —$CH_2$—$CH_3$, or —$CH_2$—$CH_2$—$CH_3$).

Continuing to refer to formula ($I_a$), ($I_b$), ($II_a$), ($II_b$), ($I_c$), ($I_d$), ($II_c$), and ($II_d$), in an example embodiment, $R_{1a}$ can be a hydrogen atom and $R_{1b}$ can be an alkyl-aryl group, including a ($C_1$-$C_6$)-alkyl-aryl group, such as a ($C_1$-$C_6$)-alkyl-phenyl group (e.g., ($CH_2$)-phenyl), or ($C_1$-$C_3$)-alkyl-aryl group, such as a ($C_1$-$C_3$)-alkyl-phenyl group.

Continuing to refer to formula ($I_a$), ($I_b$), ($II_a$), ($II_b$), ($I_c$), ($I_d$), ($II_c$), and ($II_d$), in an example embodiment, $R_{1a}$ and $R_{1b}$ can be each independently selected from an alkyl group, a hydroxylalkyl group, an optionally substituted alkyl-aryl group, or a hydrogen atom, including, for example, compounds having chemical formula (A); (B); (C); (D); (E); (F); or (G) (as described further below), wherein $R_{1a}$ and $R_{1b}$ are thus selected.

Continuing to refer to formula ($I_a$), ($I_b$), ($II_a$), ($II_b$), ($I_c$), ($I_d$), ($II_c$), and ($II_d$), in an example embodiment, $R_{1a}$ and $R_{1b}$ can be joined together, along with the nitrogen atom to which they are attached, to form a 3-10-membered optionally substituted heterocyclic ring, wherein the heterocyclic ring further includes an oxygen atom.

Continuing to refer to formula ($I_a$), ($I_b$), ($II_a$), ($II_b$), ($I_c$), ($I_d$), ($II_c$), and ($II_d$), in an example embodiment, $R_{1a}$ and $R_{1b}$ can be joined together, along with the nitrogen atom to which they are attached, to form a 3-10-membered, for example, a 5-membered or a 6-membered, optionally substituted heterocyclic ring, wherein the heterocyclic ring further includes an oxygen atom, and wherein the heterocyclic ring is further substituted with at least one ($C_1$-$C_6$)-alkyl group, for example, at least one methyl group, or at least two methyl groups, wherein the ($C_1$-$C_6$)-alkyl group may be two substituents on a single (i.e., the same) heterocyclic carbon atom, or two or more substituents on two or more different heterocyclic carbon atoms.

Continuing to refer to formula ($I_a$), ($I_b$), ($II_a$), ($II_b$), ($I_c$), ($I_d$), ($II_c$), and ($II_d$), in an example embodiment, $R_1$ can be joined together with $R_{1b}$ to form an optionally substituted saturated or unsaturated 3-10 membered ring, for example a 5-membered or 6-membered heterocyclic ring, wherein the heterocyclic ring along with the nitrogen atom includes an oxygen atom, and can be optionally substituted with at least two alkyl groups, for example, methyl groups, the alkyl groups being substituents on the same heterocyclic carbon atom. The 3-10 membered heterocyclic ring may be saturated or partially saturated, and when the heterocyclic ring is unsaturated, $R_{1a}$ can optionally be absent.

In some embodiments, wherein $R_1$ are joined together with $R_{1b}$ to form an optionally substituted saturated or unsaturated 3-10 membered ring, when the heterocyclic ring is unsaturated, $R_{1a}$ can be absent, and in particular, when the heterocyclic ring is unsaturated, and the nitrogen is participating in the formation of an unsaturated bond, $R_{1a}$ can be absent.

In further embodiments, the amino group (—$NR_{1a}R_{1b}$) in the compound of formula (I), (II), ($I_a$), ($I_b$), ($II_a$), ($II_b$), ($I_c$), ($I_d$), ($II_c$), and ($II_d$) can be protonated to form (—$N^+HR_{1a}R_{1b}$), and chemical formula (I), (II), ($I_a$), ($I_b$), ($II_a$), ($II_b$), ($I_c$), ($I_d$), ($II_c$), and ($II_d$) further include a negatively charged anion balancing the positively charged nitrogen atom, for example, a sulfate ion ($SO_4^{2-}$), a nitrate ion ($NO_3^-$), or a chlorine ion ($Cl^-$).

Next, in order to further exemplify the mescaline derivative compounds that are provided in accordance with the present disclosure, example compounds in accordance with formula (I) and (II) are provided. These include compounds having the chemical formula: (A); (B); (C); (D); (E); (F); and (G), and further include compounds have the chemical formula: A(I)-A(III); B(I)-(V); C(I)-C(XIII); D(I)-D(III); E(I)-E(V); F(I)-F(VI); and G(I)-G(V).

Thus, the present disclosure provides, in one aspect, example compounds having chemical formula (A); (B); (C); (D); (E); (F); and (G):

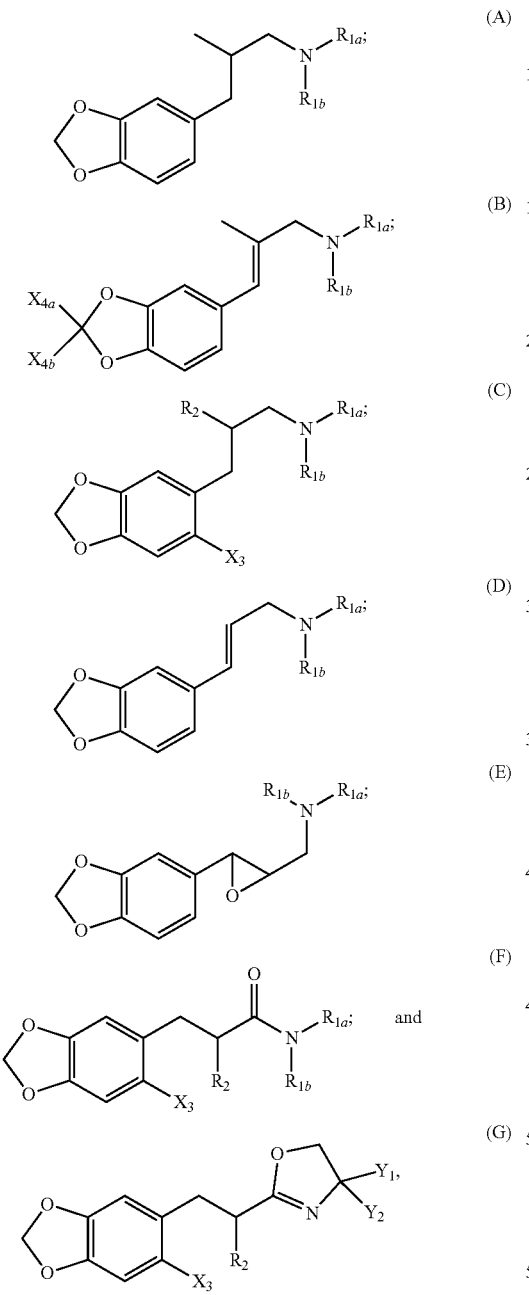

wherein in formula (B), $X_{4a}$ and $X_{4b}$ are, independently or simultaneously, a halogen or a hydrogen atom, wherein $R_{1a}$ and $R_{1b}$ in formula (A), (B), (C), (D), (E), and (F) are independently selected from an alkyl group, an optionally substituted alkyl-aryl group, or a hydrogen atom, or wherein $R_{1a}$ and $R_{1b}$ in formula (A), (B), (C), (D), (E), and (F), are joined together, along with the nitrogen atom to which they are attached, to form a 3-10-membered optionally substituted heterocyclic ring;

wherein $R_2$ in formula (C), (F) and (G), and $Y_1$ and $Y_2$ in (G) are an alkyl group or hydrogen atom; and wherein $X_3$ in formulas (C), (F) and (G) is a halogen, an O-alkyl group or hydrogen atom.

The present disclosure further provides, in one aspect, example compounds A(I)-A(III):

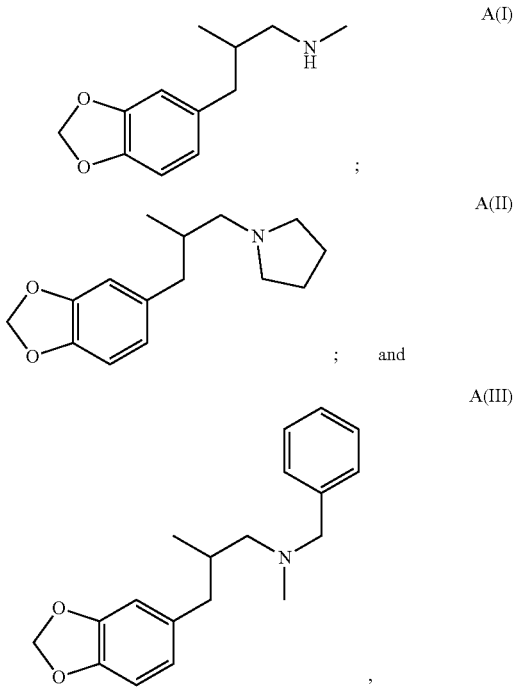

wherein in each of compound A(I) to A(III), optionally, the nitrogen atom of the N-propylamine portion is protonated and A(I) to A(III) includes a negatively charged anion balancing the positively charged nitrogen atom.

In another aspect, the present disclosure provides example compounds B(I)-B(V):

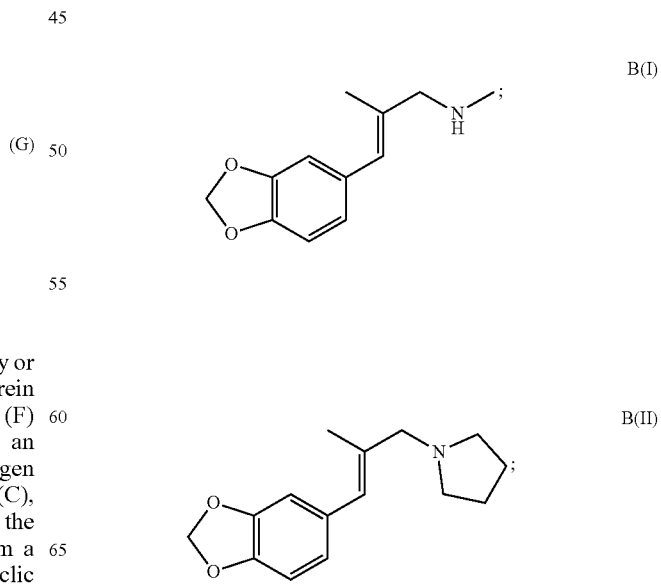

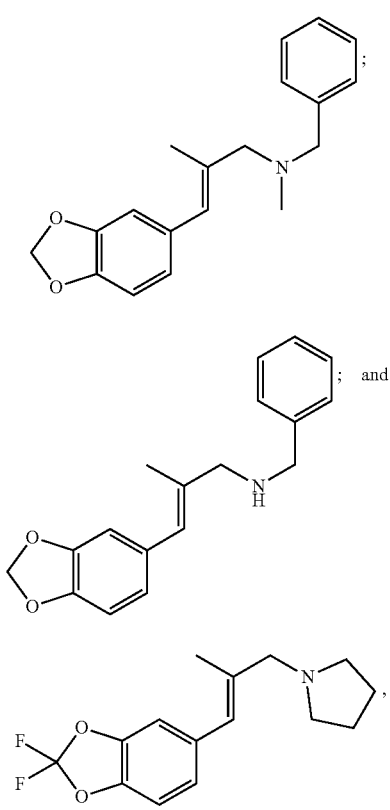

wherein in each of compound B(I) to B(V), optionally, the nitrogen atom of the N-propylamine portion is protonated and B(I) to B(V) includes a negatively charged anion balancing the positively charged nitrogen atom.

In another aspect, the present disclosure provides example compounds C(I)-C(XIII):

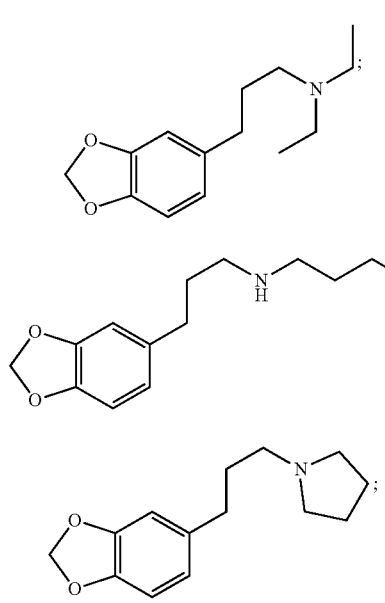

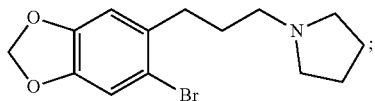
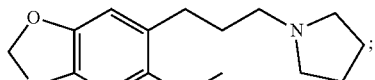
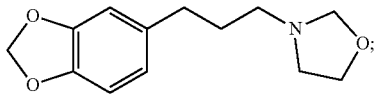
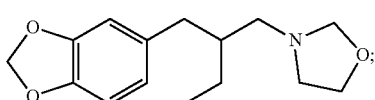
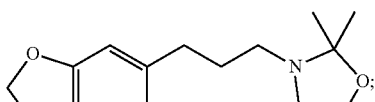
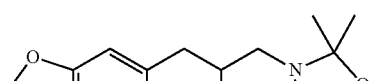
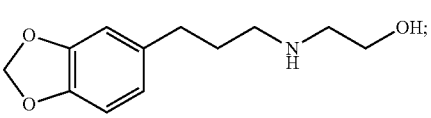
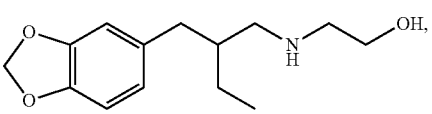
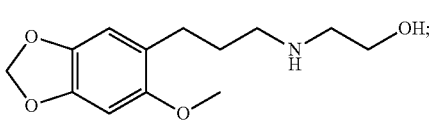
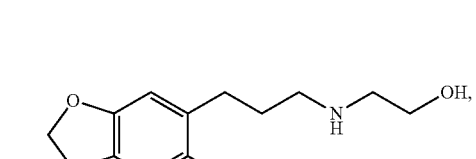

wherein in each of compound C(I) to C(XIII), optionally, the nitrogen atom of the N-propylamine portion is protonated and C(I) to C(XIII) includes a negatively charged anion balancing the positively charged nitrogen atom.

In another aspect, the present disclosure provides example compounds D(I)-D(III):

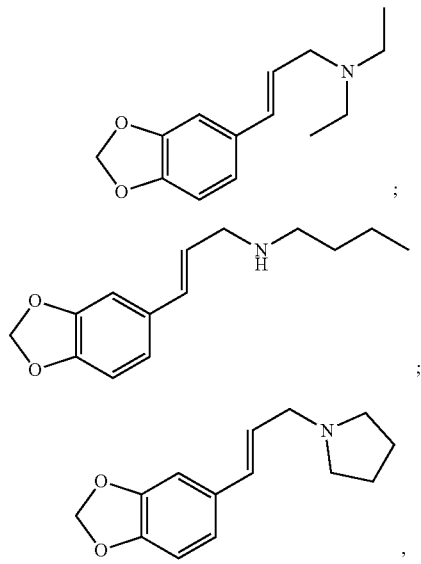

wherein in each of compound D(I) to D(III), optionally, the nitrogen atom of the N-propylamine portion is protonated and D(I) to D(III) includes a negatively charged anion balancing the positively charged nitrogen atom.

In another aspect, the present disclosure provides example compounds E(I)-E(V):

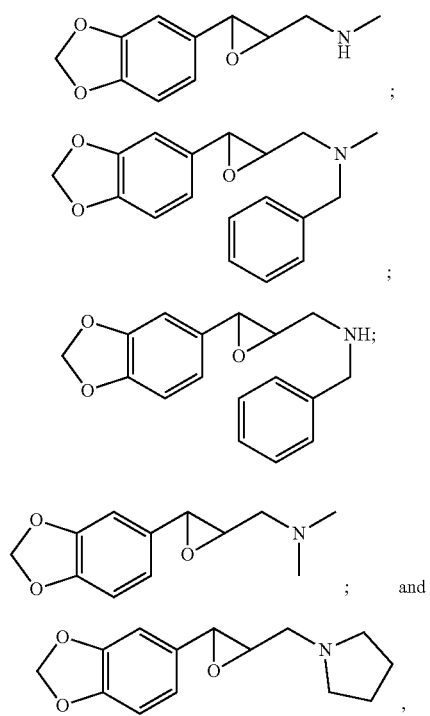

wherein in each of compound E(I) to E(V), optionally, the nitrogen atom of the N-propylamine portion is protonated and E(I) to E(V) includes a negatively charged anion balancing the positively charged nitrogen atom.

In another aspect, the present disclosure provides example compounds F(I)-F(VI):

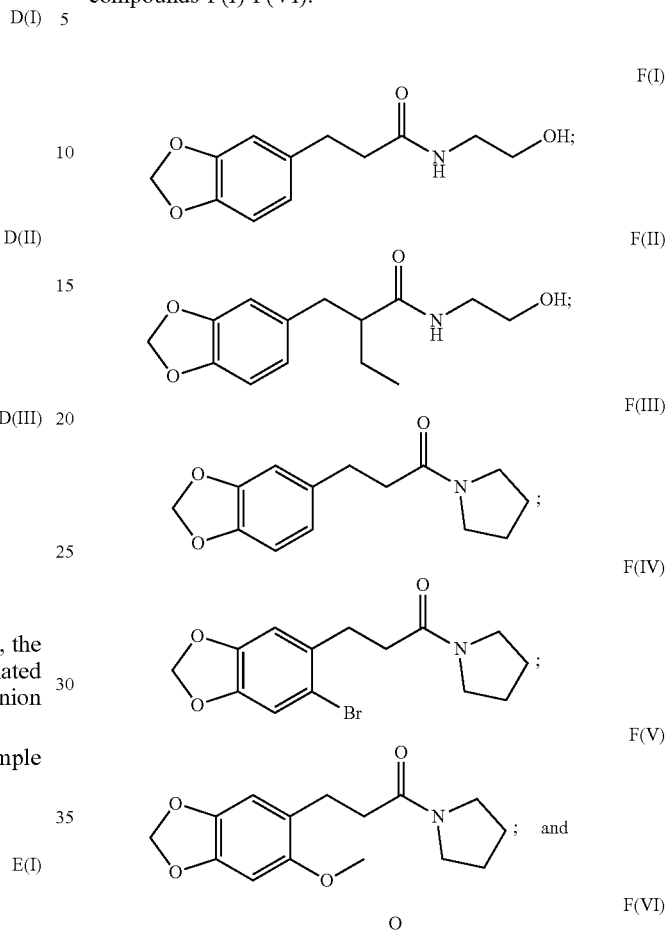

wherein in each of compound F(I) to F(VI), optionally, the nitrogen atom of the N-propylamine portion is protonated and F(I) to F(VI) includes a negatively charged anion balancing the positively charged nitrogen atom.

In another aspect, the present disclosure provides example compounds G(I)-G(V):

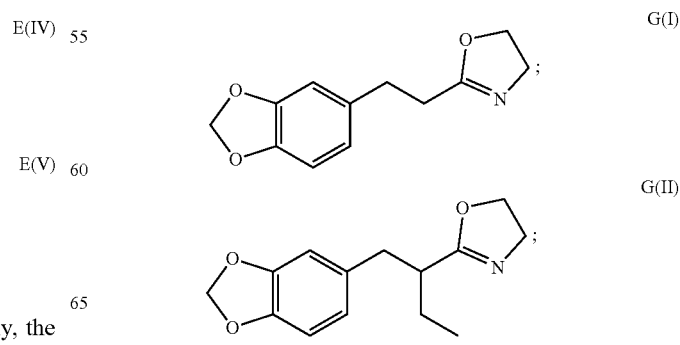

-continued

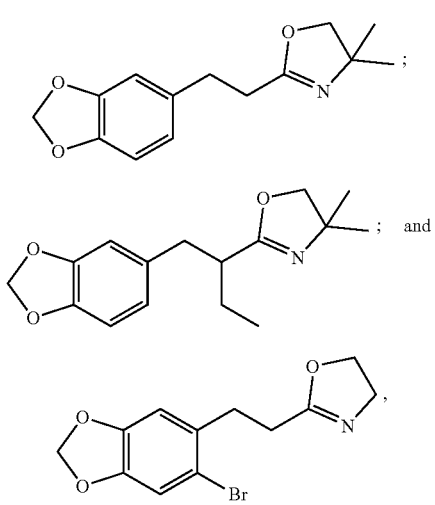

wherein in each of compound G(I) to G(V), optionally, the nitrogen atom of the N-propylamine portion is protonated and G(I) to G(V) includes a negatively charged anion balancing the positively charged nitrogen atom.

Negatively charged anions in each of the foregoing include, for example, a chloride, a nitrate ion, or sulfate ion.

In one embodiment, the compound can be a stereoisomeric compound corresponding with a chemical compound having formula A(I), A(II), A(III), C(VII), C(IX), C(XI), F(II), G(II) or G(IV), wherein the $C_2$ atom of the N-propylamine portion of the chemical compound is a chiral carbon atom. Thus, for example, in one embodiment, the stereoisomeric compound can be selected from the compounds having the formula $A(II_a)$ or $A(II_b)$:

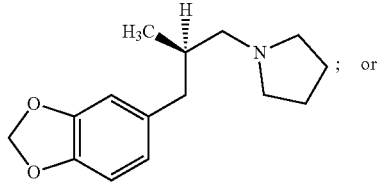

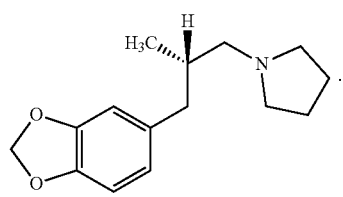

It will be understood, that similarly, stereoisomeric compounds corresponding with a chemical compound having formula A(I), A(III), C(VII), C(XI), F(II), G(II) or G(IV), wherein the $C_2$ atom of the N-propylamine portion of the chemical compound is a chiral carbon atom, can be selected and are included herein.

In one embodiment, the compound can be included in a mixture of a pair of stereoisomeric compounds, the mixture comprising a pair of stereoisomeric compounds. The mixture can have varying relative molar quantities of a first and corresponding second counterpart stereoisomeric compound (e.g., $A(II_a)$ and $A(II_b)$), for example, at least 10% (mole/mole) of a first stereoisomeric compound and 90% (mole/mole) of a second corresponding counterpart stereoisomeric compound, or 20% (mole/mole) of a first stereoisomeric compound and 80% (mole/mole) of a second corresponding counterpart stereoisomeric compound, or 30% (mole/mole) of a first stereoisomeric compound and 70% (mole/mole) of a second counterpart corresponding stereoisomeric compound, or 40% (mole/mole) of a first stereoisomeric compound and 60% (mole/mole) of a second counterpart corresponding stereoisomeric compound, or equimolar or approximately equimolar amounts of a first and of a second corresponding counterpart stereoisomeric compound.

Thus, to briefly summarize, in an aspect, the present disclosure provides novel chemical compounds which are derivatives of mescaline, fused mescaline derivatives, including in an example embodiment, fused dioxolane mescaline derivatives. The novel chemical compounds have chemical formula (I) or (II):

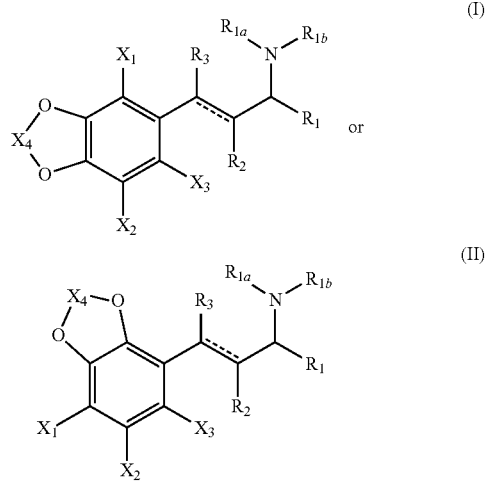

wherein, in chemical formula (I) or (II):

⚏ is a single or double bond;

$X_1$, $X_2$, and $X_3$ are independently selected from a hydrogen atom, O-alkyl, acyl, N-alkyl, OH, a halogen, or $NH_2$;

$X_4$ is an alkylene group or substituted alkylene group;

$R_1$ is a hydrogen, an alkyl group, or an oxo group, or $R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;

$R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and $R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring.

The fused mescaline derivatives of the present disclosure may be used to prepare a pharmaceutical or recreational drug formulation. Thus, in one embodiment, the present disclosure further provides in another aspect, pharmaceutical and recreational drug formulations comprising fused mescaline derivatives. Accordingly, in one aspect, the present disclosure provides in a further embodiment a pharmaceutical or recreational drug formulation comprising a chemical compound a chemical compound selected from a first chemical compound having chemical formula (I), and (II):

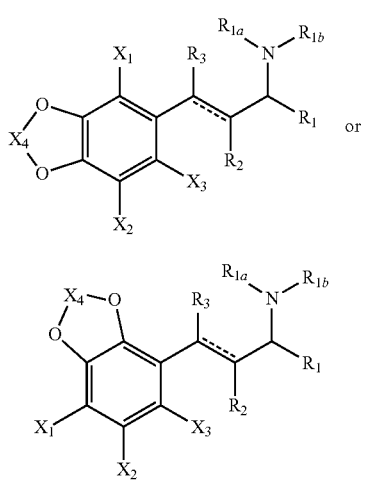

wherein, in chemical formula (I) or (II):

- ⚡ is a single or double bond;
- $X_1$, $X_2$, and $X_3$ are independently selected from a hydrogen atom, O-alkyl, acyl, N-alkyl, OH, a halogen, or $NH_2$;
- $X_4$ is an alkylene group or substituted alkylene group;
- $R_1$ is a hydrogen, an alkyl group, or an oxo group, or $R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;
- $R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and
- $R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring, together with a diluent, carrier, or excipient.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the fused mescaline derivative compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22nd Edition (Pharmaceutical Press and Philadelphia College of Pharmacy at the University of the Sciences, 2012).

The pharmaceutical and drug formulations comprising the fused mescaline derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w) or from 0.5% (w/w) to 3% (w/w) of the tablet.

In addition to the fused heterocyclic mescaline derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the fused heterocyclic mescaline derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates, and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the fused heterocyclic mescaline derivatives of the present disclosure for parenteral administration may be formulated to be immediate and/or modified release. Modified release formulations include delayed-, sustained-, pulsed-, controlled-, targeted and programmed release. Thus, the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally, or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous, or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

In further embodiments, in which the fused heterocycle mescaline compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound selected from a first chemical compound having chemical formula (I) and (II):

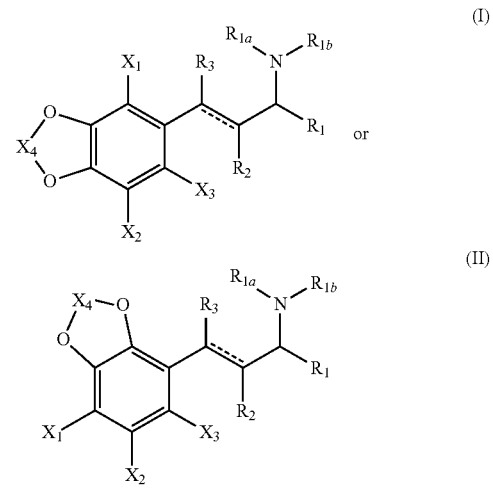

wherein, in chemical formula (I) or (II):

is a single or double bond;

$X_1$, $X_2$, and $X_3$ are independently selected from a hydrogen atom, O-alkyl, acyl, N-alkyl, OH, a halogen, or $NH_2$;

$X_4$ is an alkylene group or substituted alkylene group;

$R_1$ is a hydrogen, an alkyl group, or an oxo group, or $R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;

$R_{1a}$ and $R_{1b}$ are each independently selected from an alkyl group, a hydroxylalkyl group, an optionally substituted alkyl-aryl group, or a hydrogen atom, or R$_{1a}$ and R$_{1b}$ are joined together, along with the nitrogen atom to which they are attached, to form a 3-10-membered optionally substituted heterocyclic ring; and R$_2$ and R$_3$ are each independently selected from an alkyl group, O-alkyl group, a hydrogen atom, or R$_2$ and R$_3$ are joined together with an oxygen atom together with the carbon atoms to which they are attached to form an oxirane ring.

Brain neurological disorders, including psychiatric disorders, that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder (MDD), persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J. Psychiatr. Res. 137: 273-282); substance-related disorders, such as alcohol-related disorders, cannabis related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder. Brain neurological disorders that may be treated further include headache disorders, including migraines, including, for example, aural migraine, non-aural migraine, menstrual migraine, chronic migraine, vestibular migraine, abdominal migraine, hemiplegic migraine, and other headache disorders.

In an aspect, the compounds of the present disclosure may be used to be contacted with a receptor to thereby modulate the receptor. Such contacting includes bringing a compound of the present disclosure and receptor together under in vitro conditions, for example, by introducing the compounds in a sample containing a receptor, for example, a sample containing purified receptors, or a sample containing cells comprising receptors. In vitro conditions further include the conditions described in Example 2 hereof. Contacting further includes bringing a compound of the present disclosure and receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the receptor, the compound may activate the receptor or inhibit the receptor.

In an aspect, receptors with which the compounds of the present disclosure may be contacted include, for example, the 5-HT$_{1A}$ receptor, the 5-HT$_{2A}$ receptor, the 5-HT$_{2B}$ receptor, the 5-HT$_{2C}$ receptor, the 5-HT$_7$ receptor, the α$_{2A}$ receptor, the D$_3$ receptor, or the MT$_1$ receptor.

Thus, in a further aspect, the condition that may be treated in accordance herewith can be any receptor mediated disorder, including, for example, a 5-HT$_{1A}$ receptor-mediated disorder, a 5-HT$_{2A}$ receptor-mediated disorder, a 5-HT$_{2B}$ receptor-mediated disorder, a 5-HT$_{2C}$ receptor-mediated disorder, a 5-HT$_7$ receptor-mediated disorder, a α$_{2A}$ receptor-mediated disorder, a D$_3$ receptor-mediated disorder, or a MT$_1$ receptor-mediated disorder. Such disorders include, but are not limited to schizophrenia, psychotic disorder, attention deficit hyperactivity disorder, autism, and bipolar disorder.

In some embodiments, upon having contacted a receptor and a receptor, the compound may modulate the receptor. However, at the same time other receptors may not be modulated, e.g., a compound may activate or inhibit a first receptor, e.g., a 5-HT$_{1A}$ receptor, however the compound may at the same time not modulate a second receptor, e.g., a 5-HT$_{2A}$ receptor, or upon having contacted a first 5-HT$_{2A}$ receptor and a second 5-HT$_{1A}$ receptor, the compound may modulate the first 5-HT$_{2A}$ receptor, e.g., activate or inhibit the 5-HT$_{2A}$ receptor, however the compound may at the same time not modulate the second 5-HT$_{1A}$ receptor.

In one embodiment, in an aspect, upon administration the compounds of the present disclosure can interact with transmembrane transport protein in the subject to thereby modulate transmembrane transport protein and exert a pharmacological effect. Such contacting includes bringing a compound of the present disclosure transmembrane transport protein together under in vitro conditions, for example, by introducing the compounds in a sample containing a transmembrane transport protein, for example, a sample containing a purified transmembrane transport protein, or a sample containing cells comprising a transmembrane transport protein. Contacting further includes bringing a compound of the present disclosure and a transmembrane transport protein together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject.

In one embodiment, in an aspect, the transmembrane transport protein can be a dopamine active transporter (DAT), a norephedrine transporter (NET), or a serotonin transporter (SERT) transmembrane transport protein.

Turning now to methods of making the fused heterocyclic mescaline derivatives of the present disclosure, it is initially noted, by way of general comment that the fused heterocyclic mescaline derivatives of the present disclosure may be prepared in any suitable manner, including by any organic chemical synthesis methods, biosynthetic methods, or a combination thereof.

Figure 3A:
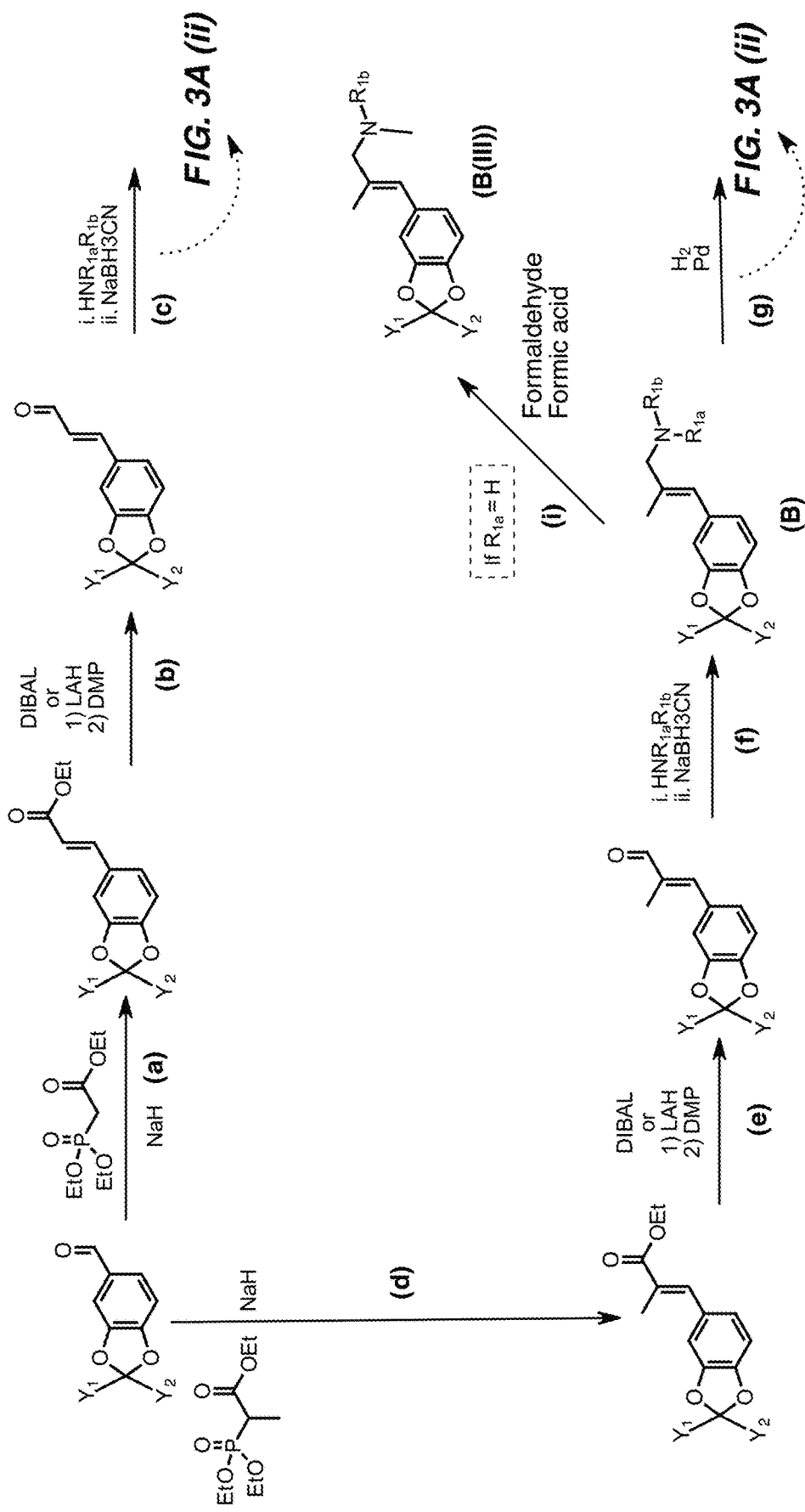
FIGS. 3A(i), 3A(ii), 3B(i), 3B(ii), 3B(iii) and 3C show example synthesis pathways and chemical reactions comprising such pathways for certain example mescaline compounds of the present disclosure, notably example mescaline derivative compounds (A), (B), (C), and (D) (FIGS. 3A(i) and 3A(ii)); compounds (C) and (F) (FIGS. 3B(i), and 3B(ii)); compound (E) (FIG. 3C); and; compound (G) (FIGS. 3B(i), 3B(ii), and 3B(iii)). Individual chemical reactions are denoted as (a), (b), (c), (d), (e), (f), (g), (h) and (i) in FIGS. 3A(i) and 3A(ii); (a), (b), (c), (d), (e), (f), (g), (h) and (i) in FIGS. 3B(i), 3B (ii) and 3B(iii); and (a) and (b) in FIG. 3C.
Figure 3A:
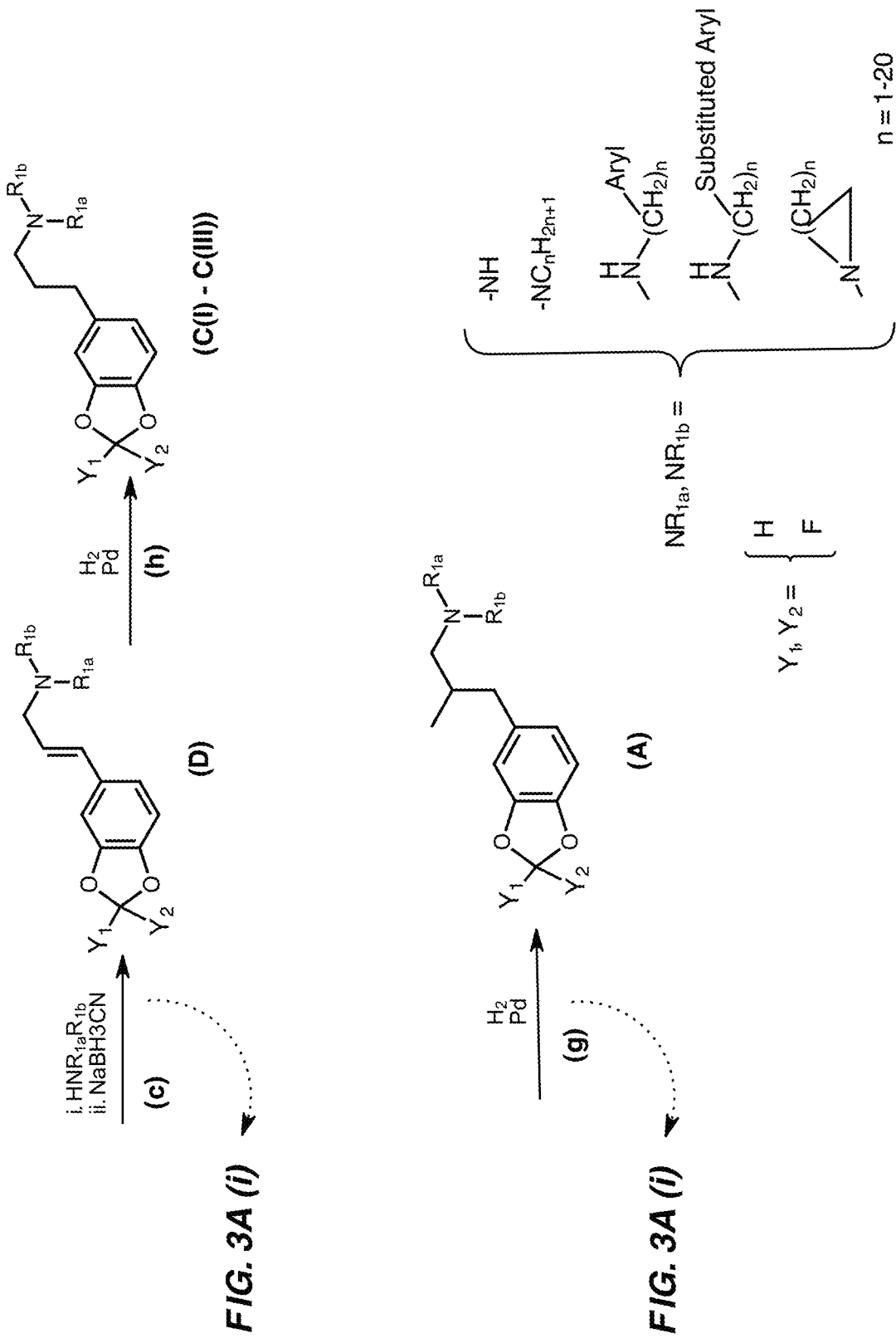

Examples of suitable chemical reactions that may be performed in accordance herewith are depicted in FIGS. 3A(i), 3A(ii), 3B(i), 3B(ii), 3B(iii), and 3C, and are further additionally detailed hereinafter in the Example section.

In general, as is known to those of skill in the art, in order to perform chemical synthetic reactions selected reactants are reacted under reaction conditions which permit the reactants to chemically react with each other and form a product, i.e., the heterocyclic mescaline derivatives of the present disclosure. Such reactions conditions may be selected, adjusted, and optimized as known by those of skill in the art. The reactions may be conducted in any suitable reaction vessel (e.g., a tube, bottle). Suitable solvents that may be used are polar solvents such as, for example, dichloromethane, dichloroethane, toluene, and so called participating solvents such as acetonitrile and diethyl ether. Suitable temperatures may range from, for example, e.g., from about −78° C. to about 60° C. Furthermore, catalysts, also known as promoters, may be included in the reaction such as iodonium dicollidine perchlorate (IDCP), any silver or mercury salts, trimethylsilyl trifluoromethanesulfonate (TMS-triflate, TMSOTf), or trifluoronmethanesulfonic acid (triflic acid, TfOH), N-iodosuccinimide, methyl triflate. Furthermore, reaction times may be varied. As will readily be appreciated by those of skill in the art, the reaction conditions may be optimized, for example, by preparing several reactant preparations and reacting these in separate reaction vessels under different reaction conditions, for example, different temperatures, using different solvents etc., evaluating the obtained fused heterocyclic mescaline derivative reaction product, adjusting reaction conditions, and selecting a desired reaction condition. Further general guidance regarding appropriate reaction conditions for performing the reactions may be found in for example: Y. Zou et al., Eur. J. Med. Chem., 138, 199-211 (2017). K. N. Campbell et al., J. Org. Chem., 16, 1736-1740 (1951). D. Ghosh, et al., Tetrahedr. Lett., 58, 2014-2018 (2017). M. G. Cabiddu et al., Tetrahedron 59, 4383-4387 (2003).

In accordance with the foregoing, in an aspect, included herein, in accordance with at least one embodiment, is a method of making a first chemical compound having chemical formula (I), or (II):

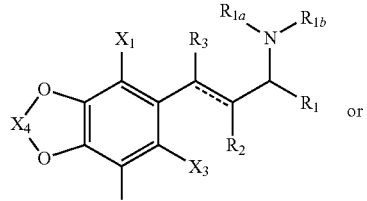

(I)

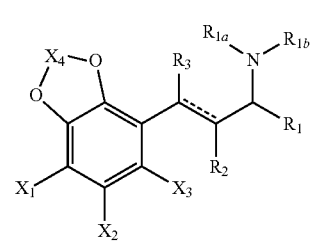

(II)

wherein, in chemical formula (I) or (II):

⚡ is a single or double bond;

$X_1$, $X_2$, and $X_3$ are independently selected from a hydrogen atom, O-alkyl, acyl, N-alkyl, OH, a halogen, or $NH_2$;

$X_4$ is an alkylene group or substituted alkylene group;

$R_1$ is a hydrogen, an alkyl group, or an oxo group, or $R_1$ is joined together with $R_{1b}$, together with the carbon atom to which $R_1$ is attached and the nitrogen atom to which $R_{1b}$ is attached, to form an optionally substituted saturated or unsaturated 3-10 membered heterocyclic ring, and when the heterocyclic ring is unsaturated, $R_{1a}$ is optionally absent;

$R_{1a}$ and $R_{1b}$ are each independently selected from an alkyl group, a hydroxylalkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring; and $R_2$ and $R_3$ are each independently selected from an alkyl group, O-alkyl group, a hydrogen atom, or $R_2$ and $R_3$ are joined together with an oxygen atom together with the carbon atoms to which they are attached to form an oxirane ring, wherein the method involves the performance of at least one chemical synthesis reaction selected from the reactions depicted in FIGS. 3A(i), 3A(ii), and 3B(i), 3B(ii), 3B(iii), and 3C.

Referring to FIGS. 3A(i) and 3A(ii), in one embodiment, the compound having chemical formula (I) can be a compound having formula (A):

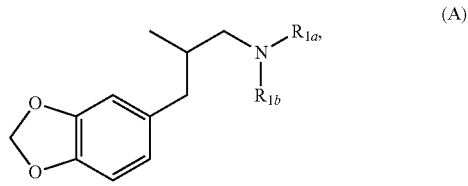

(A)

wherein $R_{1a}$ and $R_{1b}$ are each independently selected from an alkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring, and at least one chemical synthesis reaction is a reaction selected from (g); (f) and (g); (e), (f), and (g); and (d), (e), (f), and (g) depicted in FIGS. 3A(i) and 3A(ii).

Referring to FIG. 3A(i), in one embodiment, the compound having chemical formula (I) can be a compound having formula (B):

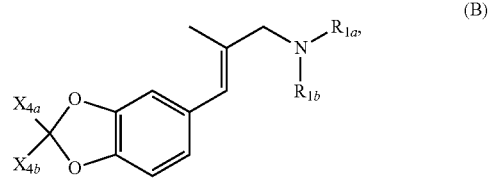

(B)

wherein in formula (B), $X_{4a}$ and $X_{4b}$ are, independently or simultaneously, a halogen atom or a hydrogen atom, $R_{1a}$ and $R_{1b}$ are each independently selected from an alkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring, and at least one chemical synthesis reaction is a reaction selected from (i); (f); (f) and (i); (e) and (f); (e), (f), and (i); (d), (e), and (f); and (d), (e), (f), and (i) depicted in FIG. 3A(i).

Figure 3B:
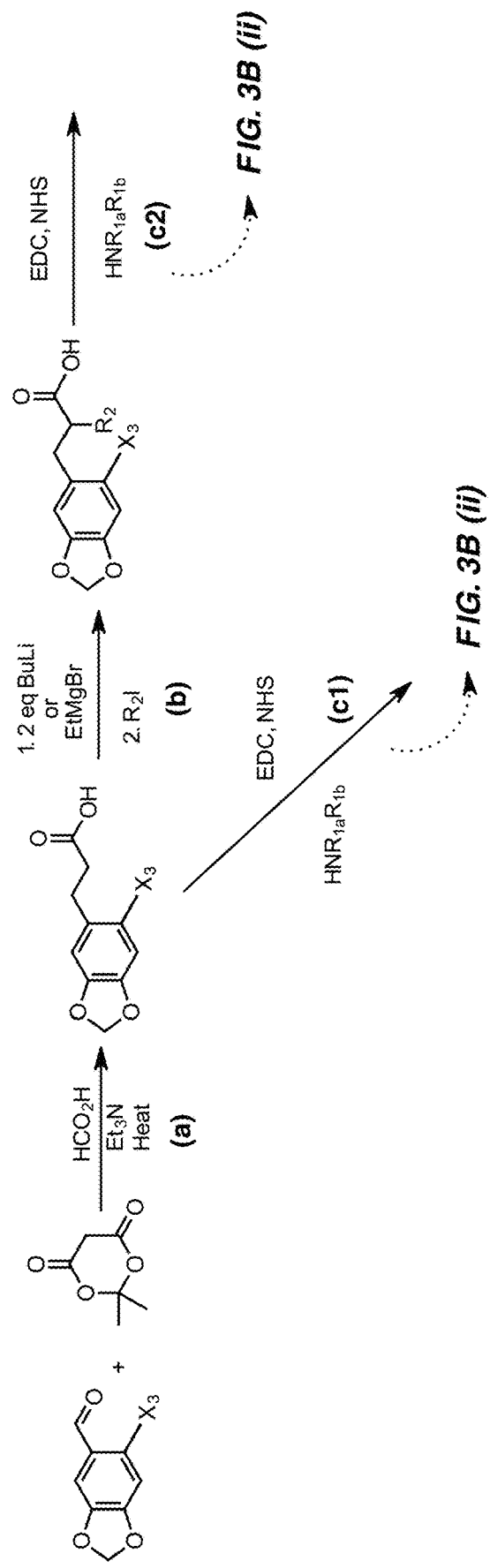
Figure 3B:
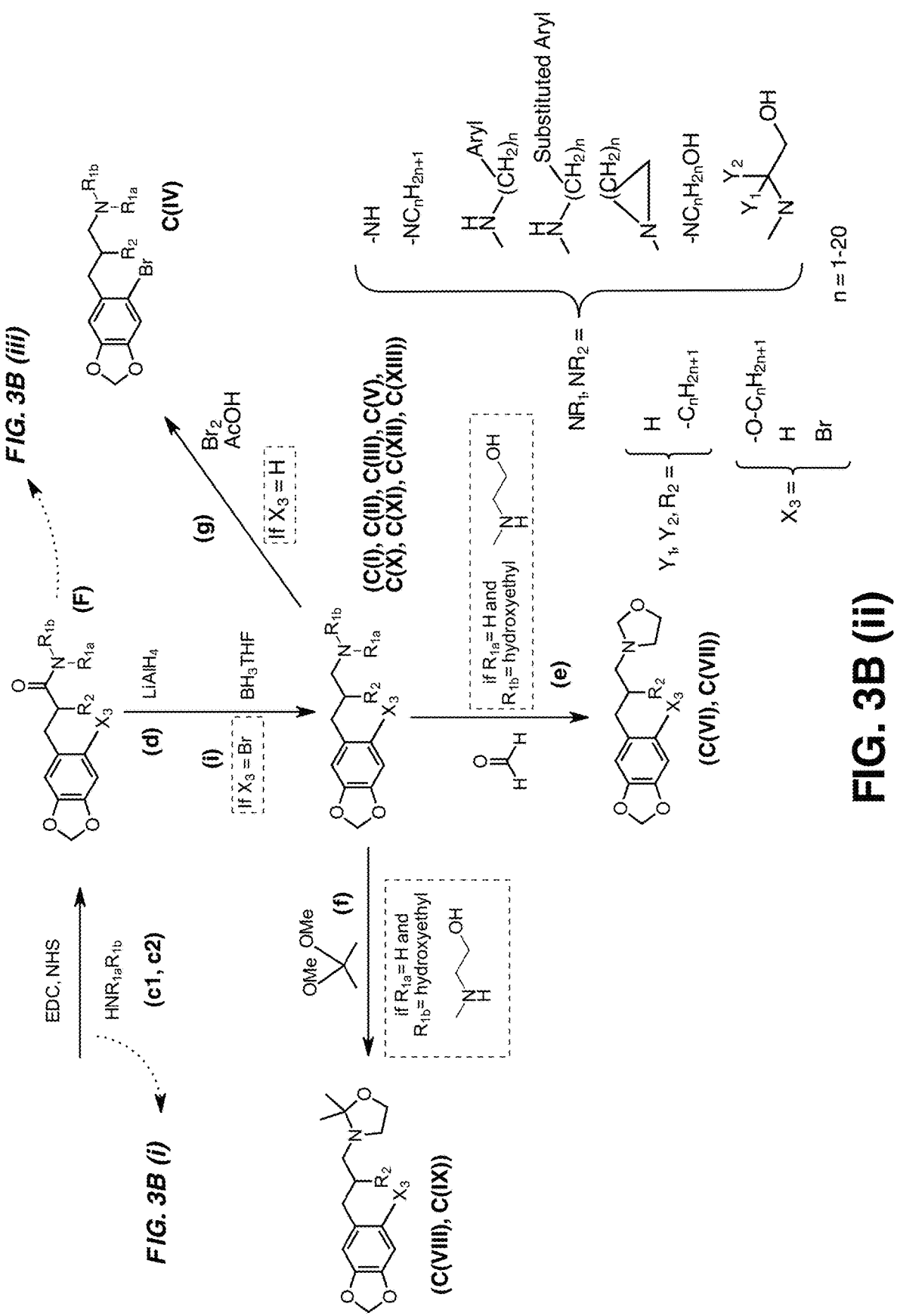

Continuing to refer to FIGS. 3A(i) and 3A(ii) and further referring to FIGS. 3B(i) and 3B(ii), in one embodiment, the compound having chemical formula ($I_a$) or ($I_c$) can be a compound having formula (C):

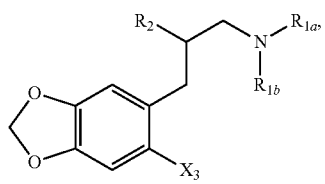

(C)

wherein $R_{1a}$ and $R_{1b}$ are each independently selected from an alkyl group, a hydroxylalkyl group, or a hydrogen atom, or $R_{1a}$ and $R_{1b}$ are joined together, along with the nitrogen atom to which they are attached, to form a 3-10-membered optionally substituted heterocyclic ring, wherein $R_2$ is selected from an alkyl group or a hydrogen atom, and wherein $X_3$ is an O-alkyl group, a halogen, or a hydrogen atom, and at least one chemical synthesis reaction is a reaction selected from:

(i) {(h); (c) and (h); (b), (c), and (h); and (a), (b), (c), and (h) in FIGS. 3A(i) and 3A(ii) (for compounds C(I), C(II), and C(III)}; or from (ii) {(f); (d) and (f); (c2), (d), and (f); (c1), (d), and (f); (b), (c2), (d), and (f); (a), (b), (c2), (d), and (f); and (a), (c1), (d), and (f) in FIGS. 3B(i) and 3B(ii) (for compounds C(VIII) and C(IX)}; or from (iii) {(e); (d) and (e); (c2), (d), and (e); (c1), (d), and (e); (b), (c2), (d), and (e); (a), (b), (c2), (d), and (e); and (a), (c1), (d), and (e) in FIGS. 3B(i) and 3B(ii) (for compounds C(VI) and C(VII)}; or from (iv) {(d); (c1) and (d); (c2) and (d); (b), (c2), and (d); and (a), (c1), and (d); and (a), (b), (c2) and (d) in FIGS. 3B(i) and 3B(ii) (for compounds C(I), C(II), C(III), C(V), C(X), C(XI), and C(XII)}; or from (v) {(i); (c1) and (i); (c2) and (i); (b), (c2), and (i); and (a), (c1), and (i); and (a), (b), (c2) and (i) in FIGS. 3B(i) and 3B(ii) (for compound C(XIII)}; or from (vi) {(g); (d) and (g); (c2), (d), and (g); (c1), (d), and (g); (b), (c2), (d), and (g); (a), (b), (c2), (d), and (g); and (a), (c1), (d), and (g) in FIGS. 3B(i) and 3B(ii) (for compound C(IV)}.

Continuing to refer to FIGS. 3A(i) and 3A(ii), in one embodiment, the compound having chemical formula ($I_b$) or ($I_d$) can be a compound having formula (D):

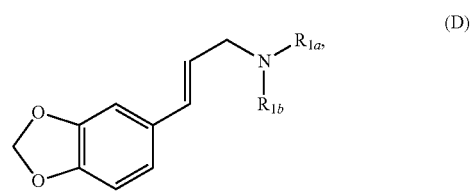

(D)

wherein $R_{1a}$ and $R_{1b}$ are each independently selected from an alkyl group, a hydrogen atom, or $R_{1a}$ and $R_{1b}$ are joined together, along with the nitrogen atom to which they are attached, to form a 3-10-membered optionally substituted heterocyclic ring, and at least one chemical synthesis reaction is a reaction selected from (c); (b) and (c); and (a), (b), and (c) depicted in FIGS. 3A(i) and 3A(ii).

Figure 3C:
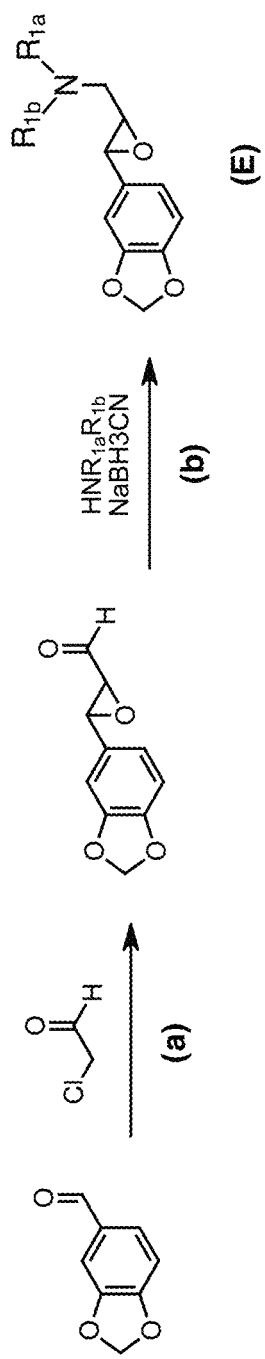

Referring to FIG. 3C, in one embodiment, the compound having chemical formula (I) can be a compound having formula (E):

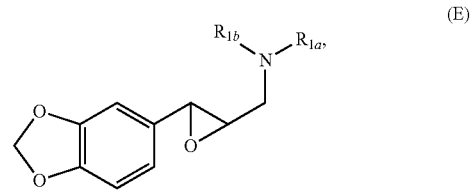

(E)

wherein $R_{1a}$ and $R_{1b}$ are each independently selected from an alkyl group, an optionally substituted alkyl-aryl group, or a hydrogen atom, or $R_{1a}$ and $R_{1b}$ are joined together, along with the nitrogen atom to which they are attached, to form a 3-10-membered optionally substituted heterocyclic ring, and at least one chemical synthesis reaction is a reaction selected from (b); (a) and (b), depicted in FIG. 3C.

Referring to FIGS. 3B(i) and 3B(ii), in one embodiment, the compound having chemical formula (I) can be a compound having formula (F):

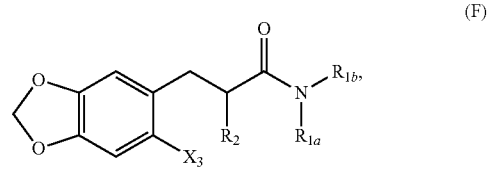

(F)

wherein $R_{1a}$ and $R_{1b}$ are each independently selected from a hydroxylalkyl group, and a hydrogen atom, or $R_{1a}$ and $R_{1b}$ are joined together, along with the nitrogen atom to which they are attached, to form a 3-10-membered optionally substituted heterocyclic ring, and wherein $R_2$ is an alkyl group or a hydrogen atom, $X_3$ is an O-alkyl group, a halogen, or a hydrogen atom, and at least one chemical synthesis reaction is a reaction selected from (c1); (c2); (b) and (c2); (a) and (c1); (a), (b), and (c2) in FIGS. 3B(i) and 3B(ii).

Referring to FIGS. 3B(i), 3B(ii), and 3B(iii), in one embodiment, the compound having chemical formula (I) can be a compound having formula (G):

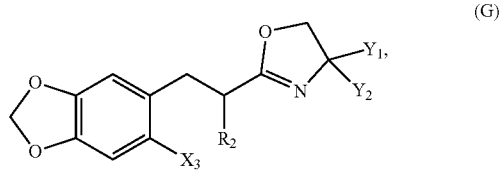

(G)

wherein $R_2$, $Y_1$ and $Y_2$ are each independently an alkyl group or a hydrogen atom, and $X_3$ is a hydrogen or a halogen, and at least one chemical synthesis reaction is a reaction selected from {(h); (c1) and (h); (c2) and (h); (b), (c2), and (h); and (a), (c1), and (h); and (a), (b), (c2) and (h) in FIGS. 3B(i), 3B(ii), and 3B(iii).

It will now be clear from the foregoing that novel heterocyclic mescaline derivatives are disclosed herein. The heterocyclic mescaline derivatives may be formulated for use as a pharmaceutical drug or recreational drug. Example embodiments and implementations of the present disclosure are further illustrated by the following examples.

EXAMPLES

Figure 4A:
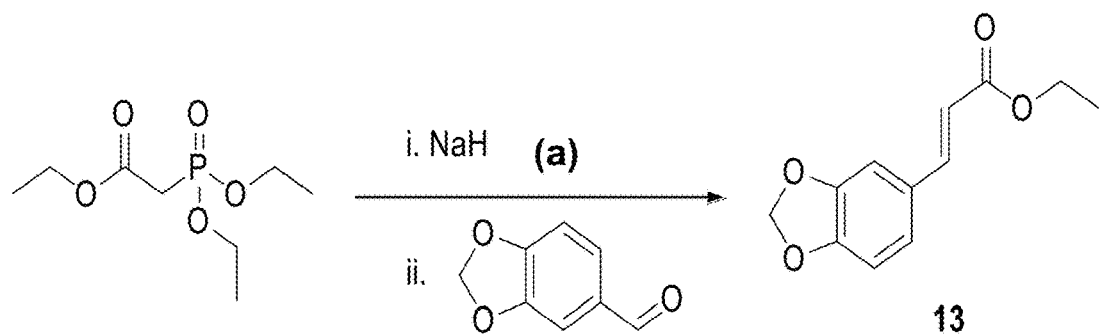
FIGS. 4A, 4B, 4C, and 4D depict example reactions in an example chemical synthesis pathway for the synthesis of a certain example compound according to the present disclosure.

Example 1—Preparation of a First N-Propylamine Fused Heterocyclic Mescaline Derivative Referring to FIG. 4A, to a suspension of sodium hydride (330 mg, 8.24 mmol) in dry THF (5 mL) at 0° C. under inert atmosphere was added a solution of triethyl phosphonoacetate (1.67 mL, 8.24 mmol) in dry THF (10 mL). Following stirring for 30 minutes, a solution of piperonal (1.00 g, 6.59 mmol) in dry THF (5 mL) was added dropwise over 10 minutes. The reaction mixture was allowed to slowly warm to room temperature overnight. Water (5 mL) was added to the stirring mixture, and the solvent was removed under reduced pressure. The remaining aqueous residue was extracted with ethyl acetate (3×25 mL). The combined organic extracts were dried over anhydrous $MgSO_4$, filtered, and concentrated to yield 13 (1.35 g, 93%). $^1$H NMR (400 MHz, $CDCl_3$) δ 7.57 (d, J=16.0 Hz, 1H), 7.00 (d, J=1.8 Hz, 1H), 6.97 (ddd, J=7.9, 1.7, 0.6 Hz, 1H), 6.78 (d, J=8.0 Hz, 1H), 6.24 (d, J=15.9 Hz, 1H), 5.97 (s, 2H), 4.23 (q, J=7.1 Hz, 2H), 1.31 (t, J=7.1 Hz, 3H) (FIG. 4A, chemical reaction (a); see: further also chemical reaction (a), FIG. 3A(i)).

Figure 4B:
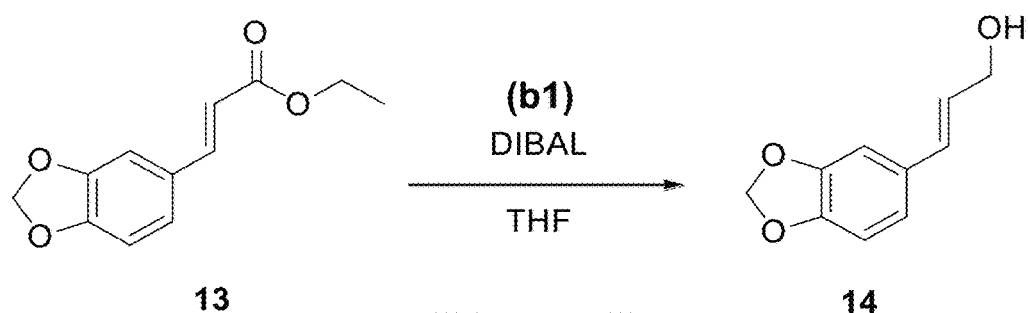

Referring next to FIG. 4B, to a solution of 13 (826 mg, 3.75 mmol) in dry THF (18.8 mL) under nitrogen atmosphere at −78° C. was added DIBAL (1 M in THF, 15.0 mL, 15.0 mmol) over 10 minutes. The reaction mixture was stirred at −78° C. for 3 hours until reaction completion, as monitored by TLC (20% EtOAc/hexanes). The reaction was quenched at 0° C. through dropwise addition of water (4 mL) followed by 15% aqueous NaOH (4 mL), water (10 mL), and stirred at room temperature for 15 minutes. Anhydrous $MgSO_4$ was added, and the slurry stirred for 3 days prior to filtration. The filtrate was concentrated under reduced pressure to yield a light yellow oily solid. Purification by flash column chromatography on silica gel (12 g, 0 to 20% EtOAc/Hex) yielded 14 as an off-white solid (422 mg, 63%). $^1$H NMR (400 MHz, $CDCl_3$) δ 6.92 (d, J=1.7 Hz, 1H), 6.81 (dd, J=7.9, 1.7 Hz, 1H), 6.75 (d, J=8.0 Hz, 1H), 6.51 (dt, J=15.7, 1.5 Hz, 1H), 6.19 (dt, J=15.8, 5.9 Hz, 1H), 5.95 (s, 2H), 4.28 (dd, J=5.9, 1.5 Hz, 2H) (FIG. 4B, chemical reaction (b1), see: further also chemical reaction (b), FIG. 3A(i)).

Figure 4C:
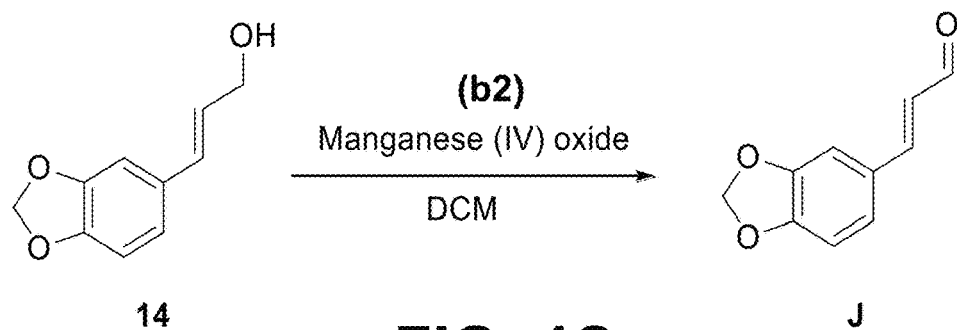

Referring next to FIG. 4C, to a solution of 14 (307 mg, 1.72 mmol) in DCM (17.2 mL) was added manganese (IV) oxide (908 mg, 10.3 mmol). The reaction mixture was stirred under ambient conditions for 18 h. More manganese (IV) oxide (359 mg, 4.08 mmol) was added, and the solution was stirred for a subsequent 3 h, at which point the reaction was complete as determined by TLC (40% EtOAc/Hex). The reaction mixture was diluted with DCM (20 mL), filtered through Celite, and washed with DCM (20 mL). The filtrate was concentrated under reduced pressure to yield a white crude solid. Purification by column chromatography on silica (4 g, 0 to 12% EtOAc/Hex) yielded the product, intermediate J, as a white solid (282 mg, 93%). $^1$H NMR (400 MHz, $CDCl_3$) δ 9.67 (d, J=7.7 Hz, 1H), 7.40 (d, J=15.8 Hz, 1H), 7.12-7.07 (m, 2H), 6.92-6.85 (m, 1H), 6.58 (dd, J=15.8, 7.7 Hz, 1H), 6.07 (s, 2H) (FIG. 4A, chemical reaction (b2), see: further also chemical reaction (b), FIG. 3A(i)).

Figure 4D:
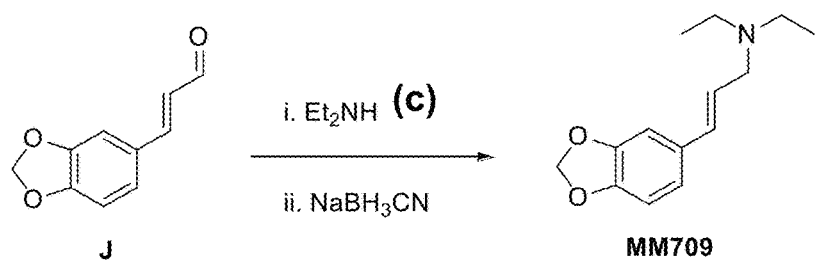

Referring next to FIG. 4D, to a solution of J (136 mg, 772 μmol) in dry MeOH (5.15 mL) under nitrogen atmosphere was added diethylamine (80.3 μL, 772 μmol). The reaction mixture was refluxed for 3 hours. Upon cooling to room temperature, sodium cyanoborohydride (255 mg, 3.86 mmol) was added and the reaction mixture was stirred at room temperature under nitrogen atmosphere for 18 h. Methanol was removed by rotary evaporation, and the residue taken up in ethyl acetate (15 mL) and washed with brine (3×10 mL). The organic phase was dried over anhydrous $MgSO_4$, filtered and concentrated. The crude residue was purified by FC on silica gel (4 g, 0 to 6% MeOH/DCM) to yield MM709 as a yellow, oily solid (45 mg, 25%). LRMS-HESI: calculated 234.15 m/z for $[M+H]^+$, found 234.15. $^1$H NMR (400 MHz, $CDCl_3$) δ 6.95 (d, J=1.7 Hz, 1H), 6.82 (dd, J=8.1, 1.7 Hz, 1H), 6.77 (d, J=8.0 Hz, 1H), 6.49-6.42 (m, 1H), 6.15 (dt, J=15.7, 6.8 Hz, 1H), 5.97 (s, 2H), 3.28 (d, J=6.8 Hz, 2H), 2.62 (q, J=7.2 Hz, 4H), 1.10 (t, J=7.2 Hz, 6H) (FIG. 4A, chemical reaction (c), see: further also chemical reaction (c), FIG. 3A(ii)).

It is noted that MM709 corresponds with chemical compound D(I):

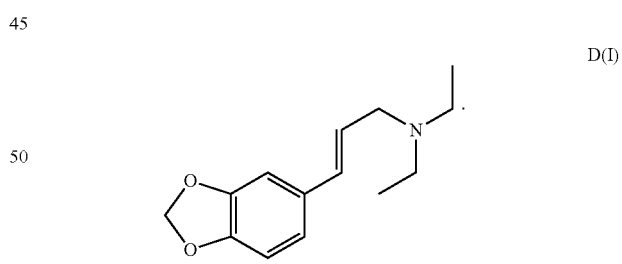

D(I)

5-HT receptor radioligand competition assays. Activity at $5\text{-}HT_{1A}$ and $5\text{-}HT_{2A}$ receptors were assessed as described for Example 2, except the compound with formula D(I) was evaluated in place of the compound with formula B(II). Table 1 shows radioligand competition assay results for positive controls, negative controls, and compound with formula D(I), in the form of $K_i$ values. In view of results for both positive and negative controls, wherein negative controls yield data insufficient for reliable $K_i$ calculations (i.e., $K_i$>1000 μM) the $K_i$ value obtained for the compound with formula D(I) at the $5\text{-}HT_{1A}$ receptor (11.0 μM, Table 1) indicates ligand-receptor binding. Similarly, the $K_i$ value obtained for the compound with formula D(I) at the 5-HT$_{2A}$ receptor (21 μM, Table 1) indicates ligand-receptor binding.

5-HT$_{1A}$ receptor functional cellular response assay. Functional engagement of the 5-HT$_{1A}$ receptor within an engineered cell system was assessed as described for Example 2, except the compound with formula D(I) was evaluated in place of the compound with formula B(II). Table 2 shows functional assay results for positive controls, calibrators, and compound with formula D(I), in the form of EC$_{50}$ values. In view of results for controls and calibrator compounds, wherein a negative cellular response corresponded to an EC$_{50}$ value >1000 μM, the EC$_{50}$ value for the compound with formula D(I) in this assay (>1000 μM, Table 2) suggested little or no ligand-receptor engagement.

In Vitro Survey of Pharmacological Interaction Profiles at Receptors and Transporters Linked to Targeted Health Conditions.

The compound with formula D(I) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A (5-HTR$_{1A}$), HTR2A (5-HTR$_{2A}$), HTR2B (5-HT$_{2B}$), HTR2C (5-HT$_{2C}$), HTR7 (5-HT$_{7}$), alpha2A ($α_{2A}$), MT1 (MT$_1$), D3 (D$_3$)) and 3 transporters (SERT, DAT, NET). Assays were conducted using the same materials and procedures outlined in Example 2, except the compound with formula D(I) was used in place of the compound with formula B(II). Overall assay conditions are summarized in Tables 3 and 4 for GPCR and transporters, respectively. Results for all calibrator compounds, control compounds, and test compounds including the compound with formula D(I) are summarized in Table 5.

Figure 5A:
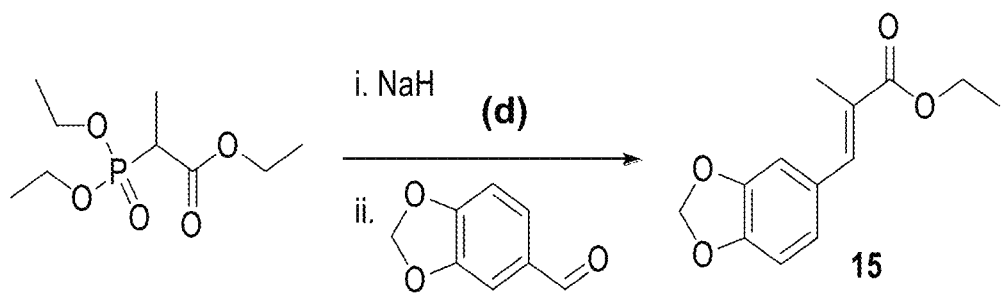
FIGS. 5A, 5B, 5C, and 5D depict further example reactions in another example chemical synthesis pathway for the synthesis of another example compound according to the present disclosure.

Example 2—Preparation of a Second N-Propylamine Fused Heterocyclic Mescaline Derivative Referring to FIG. 5A, to a suspension of sodium hydride (330 mg, 8.24 mmol) in dry THF (5.00 mL) at 0° C. under inert atmosphere was added a solution of triethyl-2-phosphonopropionate (1.82 mL, 8.24 mmol) in dry THF (10.0 mL). Following stirring for 30 minutes, a solution of piperonal (1.00 g, 6.59 mmol) in dry THF (5.00 mL) was added dropwise over 10 minutes. The reaction mixture was allowed to slowly warm to room temperature and stirred for 18 h. Water (5 mL) was added to the stirring mixture, and the solvent was removed under reduced pressure. The remaining aqueous residue was extracted with ethyl acetate (3×25 mL). The combined organic extracts were dried over anhydrous MgSO$_4$, filtered, and concentrated to yield 15 (1.55 g, 100%). $^1$H NMR (400 MHz, CDCl$_3$) δ 7.60 (dd, J=2.0, 1.1 Hz, 1H), 6.96-6.90 (m, 2H), 6.84 (d, J=8.0 Hz, 1H), 5.99 (s, 2H), 4.27 (q, J=7.1 Hz, 2H), 2.12 (d, J=1.5 Hz, 3H), 1.35 (t, J=7.1 Hz, 3H) (FIG. 5A, chemical reaction (d), see: further also chemical reaction (d), FIG. 3A(i)).

Figure 5B:
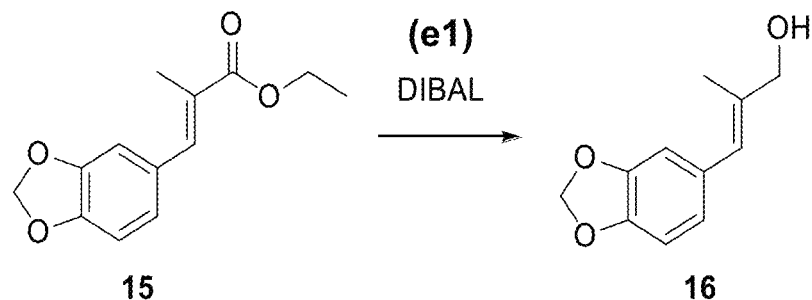

Referring to FIG. 5B, to a solution of 15 (1.55 g, 6.62 mmol) in dry THF (33.1 mL) under nitrogen atmosphere at −78° C. was added diisobutylaluminum hydride (DIBAL) (1 M in THF, 19.9 mL, 19.9 mmol) over 10 minutes. The reaction mixture was stirred at −78° C. for a further 2 hours. The reaction was quenched at 0° C. through dropwise addition of water (0.4 mL) followed by 15% aqueous NaOH (0.4 mL), water (1 mL), and stirred at room temperature for 15 minutes. Anhydrous MgSO$_4$ was added, and the slurry was stirred for 15 minutes prior to filtration. The filtrate was concentrated under reduced pressure to yield a colorless oil. Purification by flash chromatography on silica gel (25 g, 0 to 20% EtOAc/Hex) yielded 16 (1.21 g, 95%).

$^1$H NMR (400 MHz, CDCl$_3$) δ 6.80-6.76 (m, 2H), 6.73 (dd, J=8.1, 1.6 Hz, 1H), 6.41 (q, J=1.6 Hz, 1H), 5.94 (s, 2H), 4.14 (d, J=1.4 Hz, 2H), 1.87 (d, J=1.4 Hz, 3H) (FIG. 5B, chemical reaction (e1), see: further also chemical reaction (e), FIG. 3A(i)).

Figure 5C:
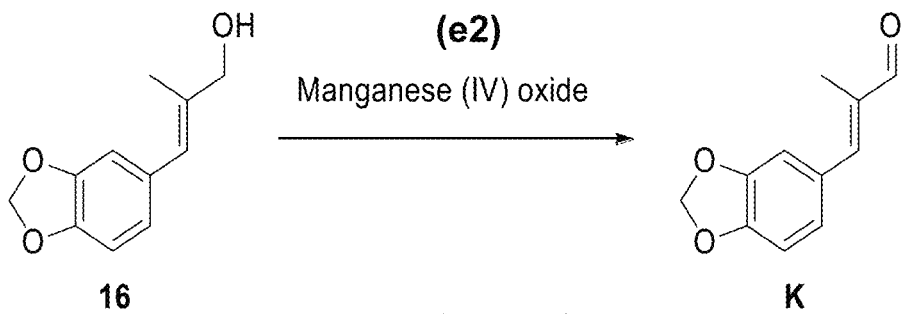

Referring to FIG. 5C, to a solution of 16 (524 mg, 2.73 mmol) in DCM (27.3 mL) was added manganese (IV) oxide (1.44 g, 16.4 mmol). The dark reaction mixture was allowed to stir for 18 hours. More manganese (IV) oxide (565 mg, 6.43 mmol) was added to the reaction mixture and stirred for a subsequent 3 h, at which point the reaction was complete as determined by TLC (40% EtOAc/Hex). The reaction mixture was diluted with DCM (20 mL), filtered through Celite, and washed with DCM (20 mL). The filtrate was concentrated under reduced pressure to yield a white crude solid. Purification by flash column chromatography on silica gel (4 g, 0 to 12% EtOAc/Hex) yielded the product, intermediate K, as a white solid (474 mg, 91%). $^1$H NMR (400 MHz, CDCl$_3$) δ 9.55 (s, 1H), 7.17 (q, J=1.4 Hz, 1H), 7.12-7.07 (m, 2H), 6.92 (d, J=8.0 Hz, 1H), 6.06 (s, 2H), 2.09 (d, J=1.4 Hz, 3H) (FIG. 5C, chemical reaction (e2), see: further also chemical reaction (e), FIG. 3A(i)).

Figure 5D:
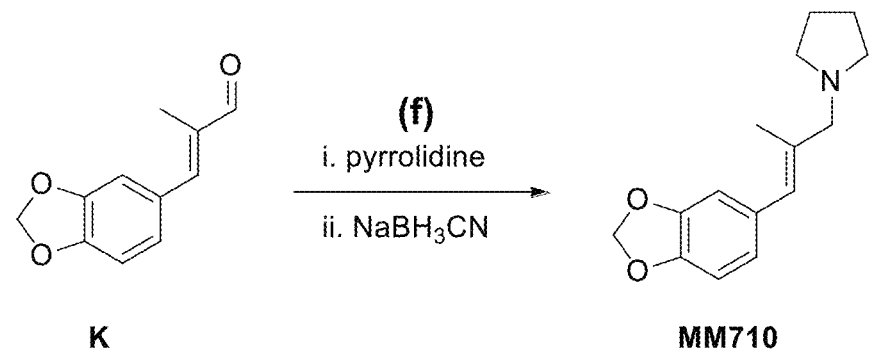

Referring to FIG. 5D, to a solution of K (130 mg, 684 μmol) in dry methanol (4.56 mL) under nitrogen atmosphere was added pyrrolidine (56.4 μL, 684 μmol). The reaction mixture was refluxed for 4 h, then cooled to room temperature and sodium cyanoborohydride (226 mg, 3.42 mmol) was added. After stirring at room temperature overnight, methanol was removed under reduced pressure, the residue was taken up in ethyl acetate (25 mL) and washed with brine (2×20 mL). The organic phase was dried over anhydrous MgSO$_4$, filtered, and concentrated under reduced pressure. Purification by FC on silica gel (4 g, 0 to 6% MeOH/DCM) yielded MM710 as a yellow oil (64 mg, 38%). LRMS-HESI: calculated 246.15 m/z for [M+H]$^+$, found 246.17. $^1$H NMR (400 MHz, CDCl$_3$) δ 6.85-6.73 (m, 3H), 6.39-6.34 (m, 1H), 5.96 (s, 2H), 3.15 (d, J=1.4 Hz, 2H), 2.56 (ddt, J=6.8, 4.8, 2.1 Hz, 4H), 1.94 (d, J=1.4 Hz, 3H), 1.85-1.80 (m, 4H) (FIG. 5D, chemical reaction (f), see: further also chemical reaction (f), FIG. 3A(i)).

It is noted that MM710 corresponds with chemical compound B(II):

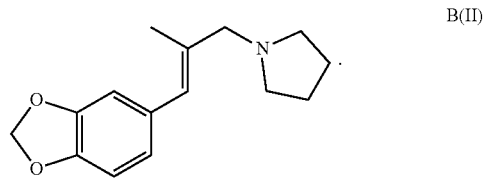

B(II)

5-HT Receptor Radioligand Competition Assays.

Figure 14A:
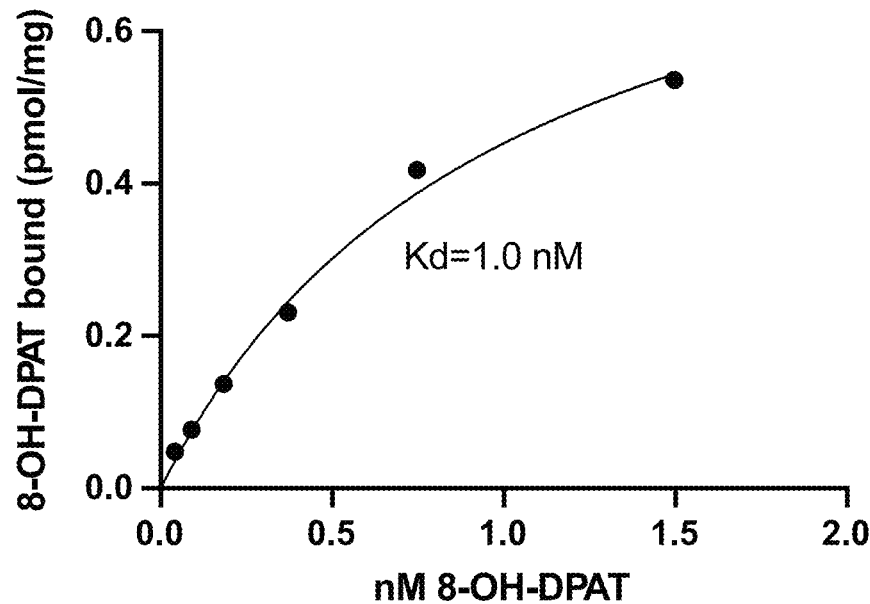
FIGS. 14A, 14B, 14C, 14D, 14E, 14F, 14G, 14H, 14I, 14J, 14K, and 14L depict various graphs representing certain experimental results, notably graphs obtained in the performance of experimental assays to evaluate the pharmaceutical efficacy of an example compound having chemical formula B(II), notably a radioligand 5-$HT_{1A}$ receptor saturation binding assay using radiolabeled 8-hydroxy-DPAT [propyl-2,3-ring-1,2,3-$^3$H] (binding curve) (FIG. 14A); a 5-$HT_{1A}$ receptor competition assay using DMSO (negative control) (FIG. 14B); a 5-$HT_{1A}$ receptor competition assay using tryptophan (negative control) (FIG. 14C); a 5-$HT_{1A}$ receptor competition assay using serotonin (positive control) (FIG. 14D); a 5-$HT_{1A}$ receptor competition assay using mescaline (positive control) (FIG. 14E); a 5-$HT_{1A}$ receptor competition assay using 2C-B (positive control) (FIG. 14F); a 5-$HT_{1A}$ receptor competition assay using MDMA (positive control) (FIG. 14G); a 5-$HT_{1A}$ receptor competition assay using escaline (FIG. 14H); a 5-$HT_{1A}$ receptor competition assay using proscaline (FIG. 14I); a 5-$HT_{1A}$ receptor competition assay using fluoxetine (positive control) (FIG. 14J); a 5-$HT_{1A}$ receptor competition assay using vortioxetine (positive control) (FIG. 14K); a 5-$HT_{1A}$ receptor competition assay using the compound with formula B(II) (FIG. 14L).
Figure 14B:
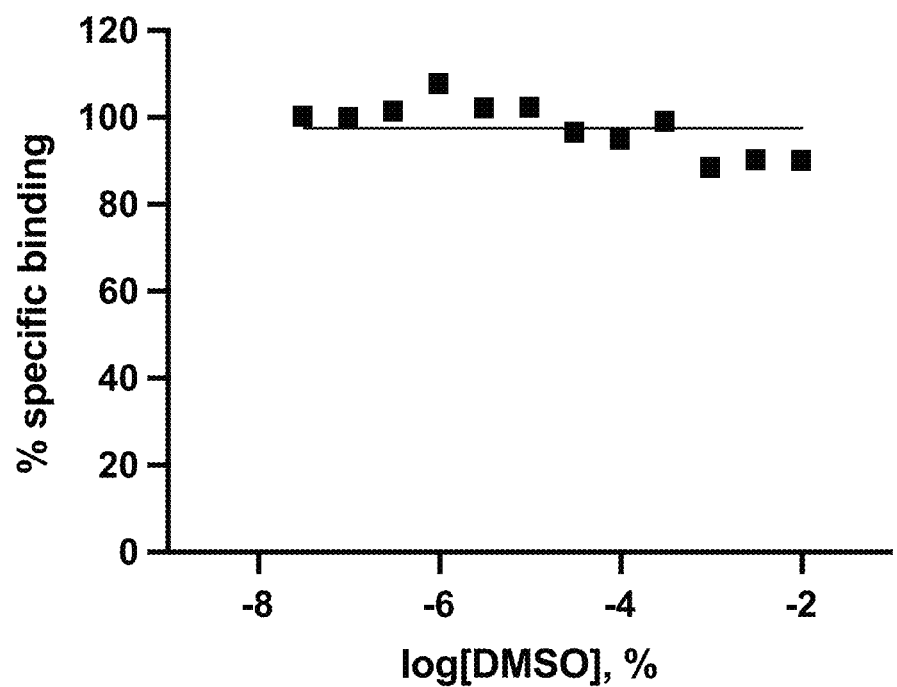
Figure 14C:
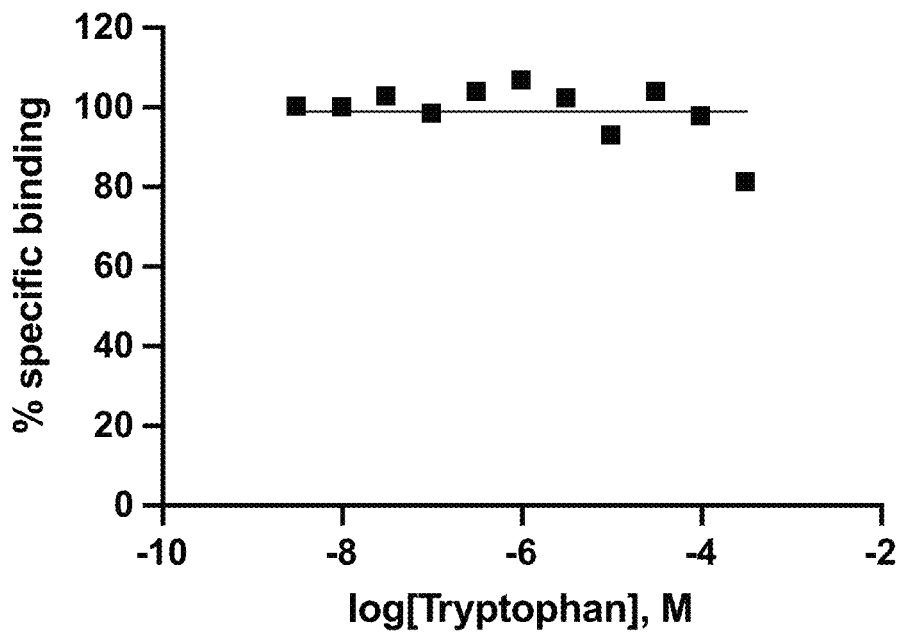
Figure 14D:
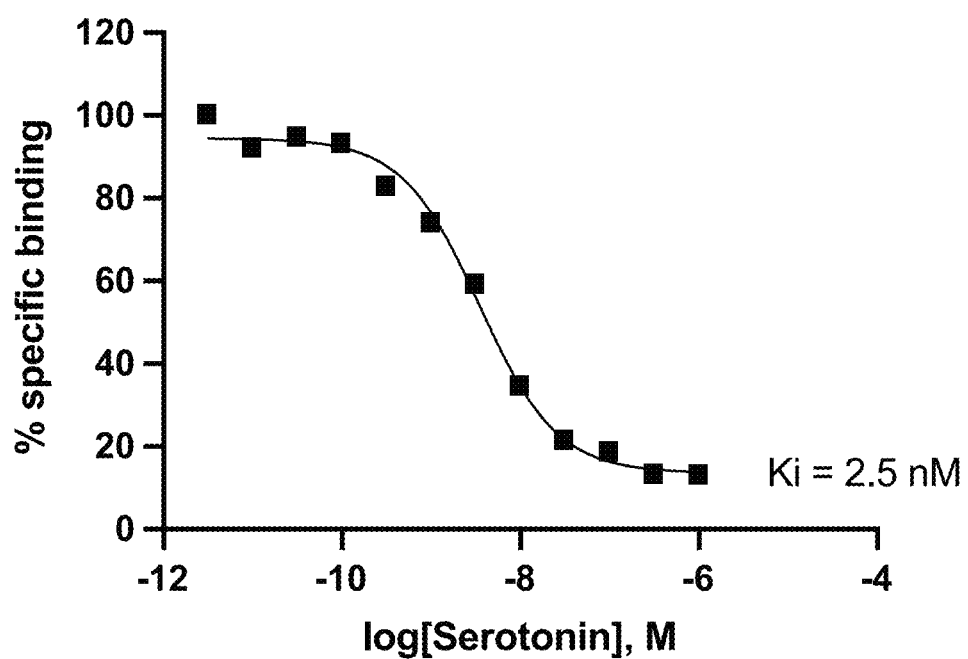
Figure 14E:
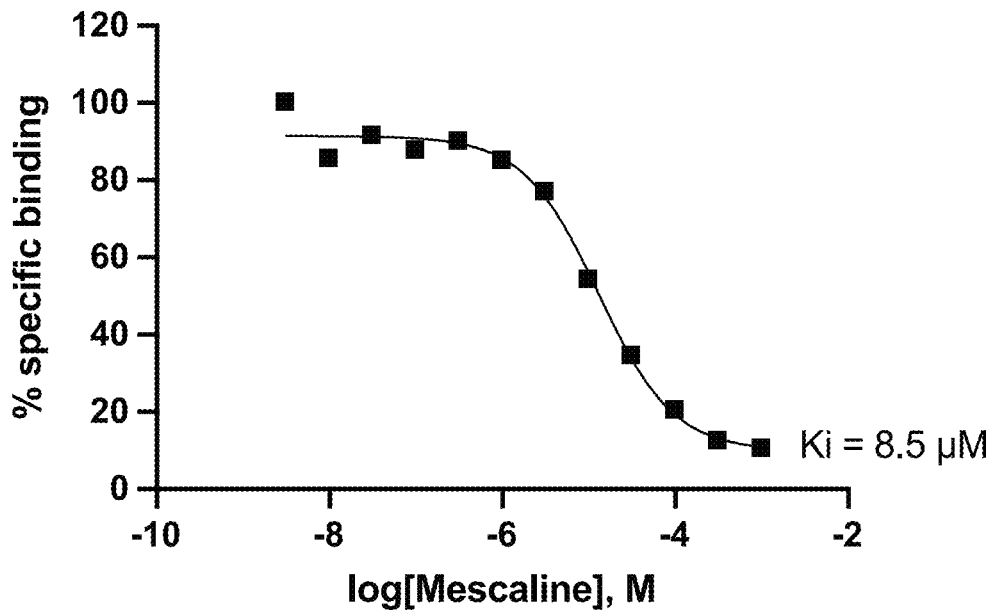
Figure 14F:
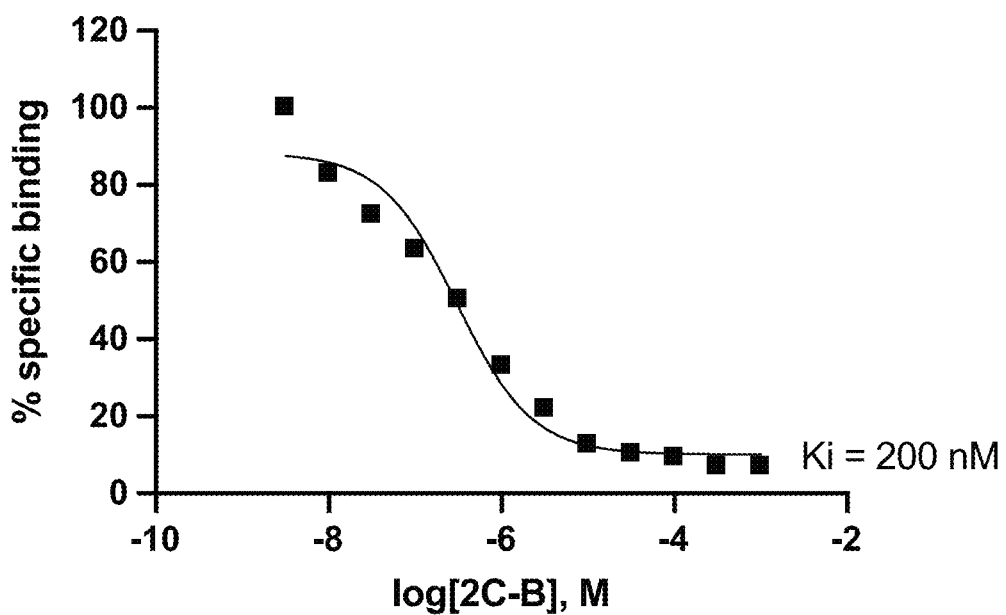
Figure 14G:
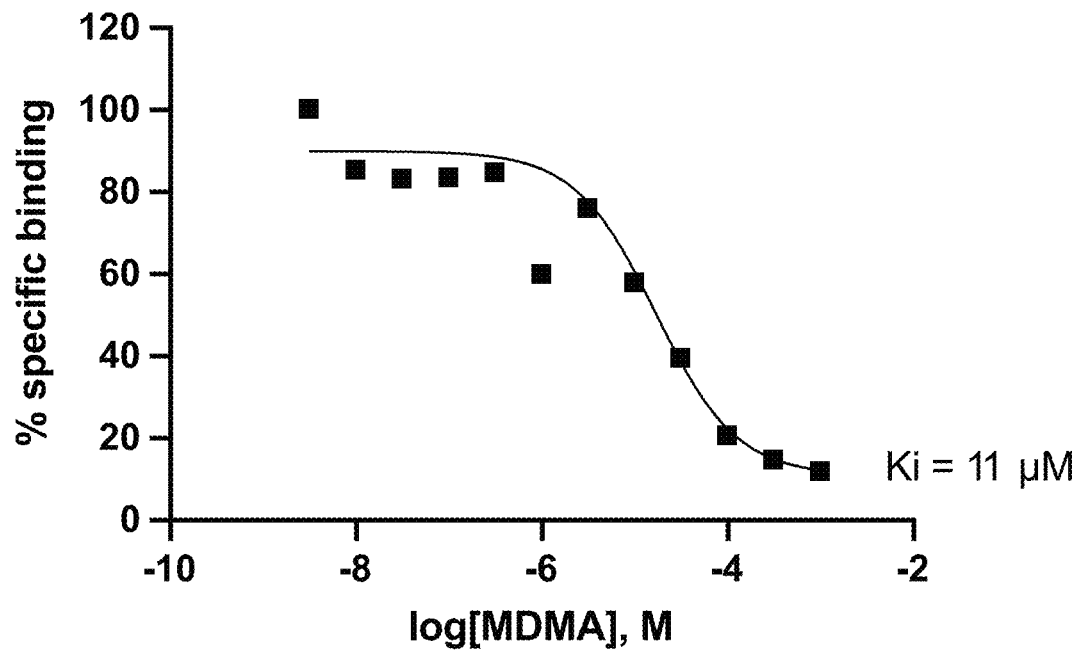
Figure 14H:
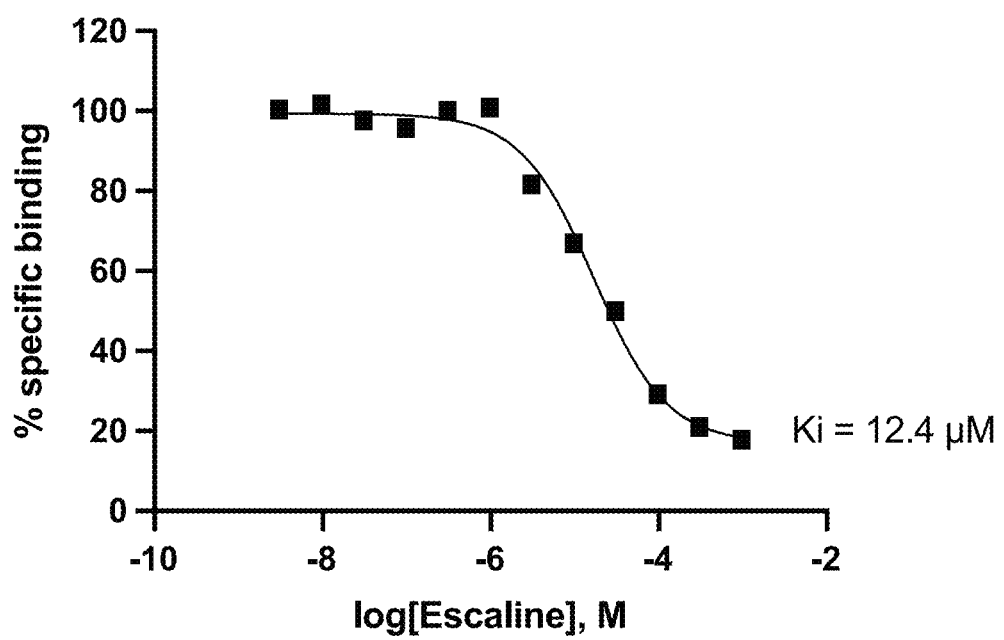
Figure 14I:
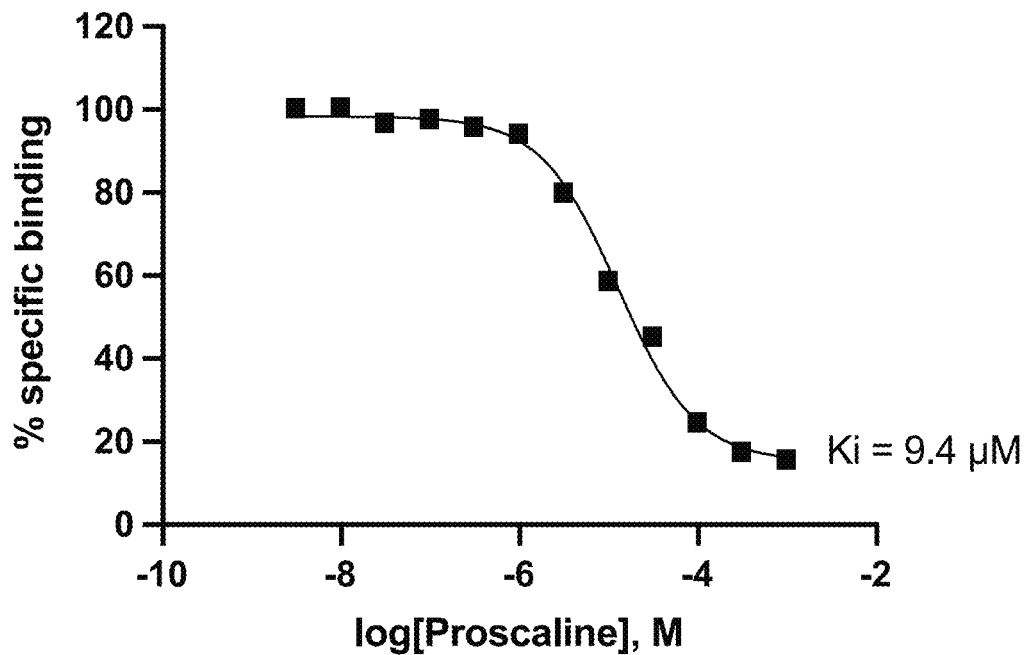
Figure 14J:
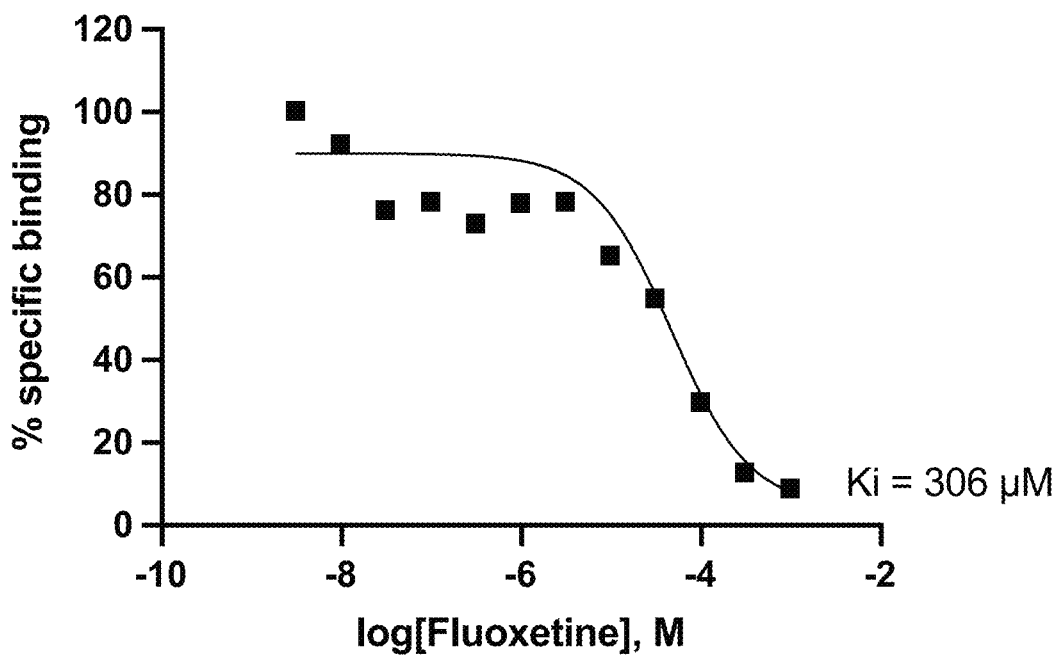
Figure 14K:
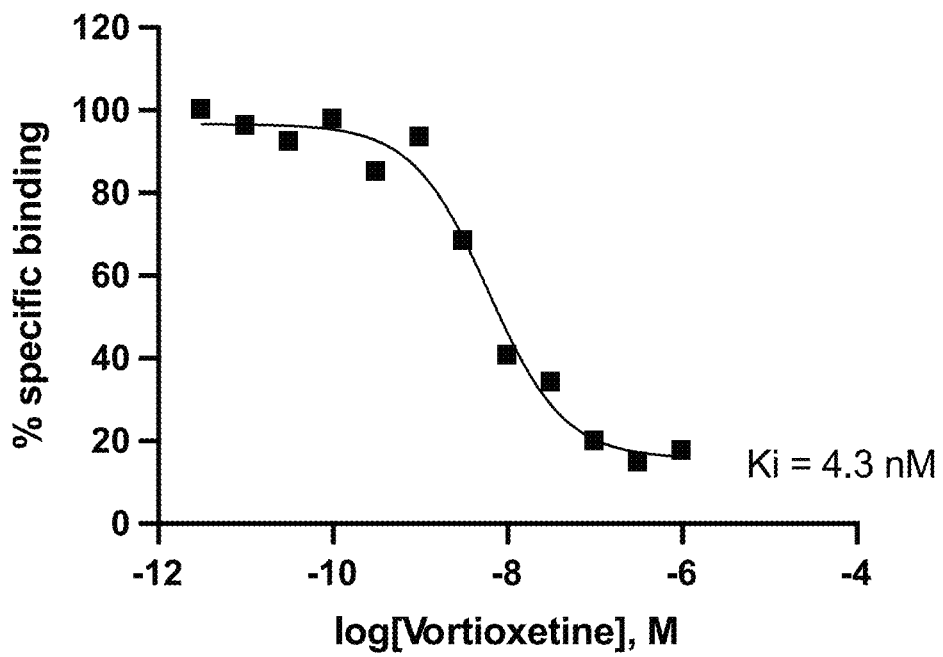
Figure 14L:
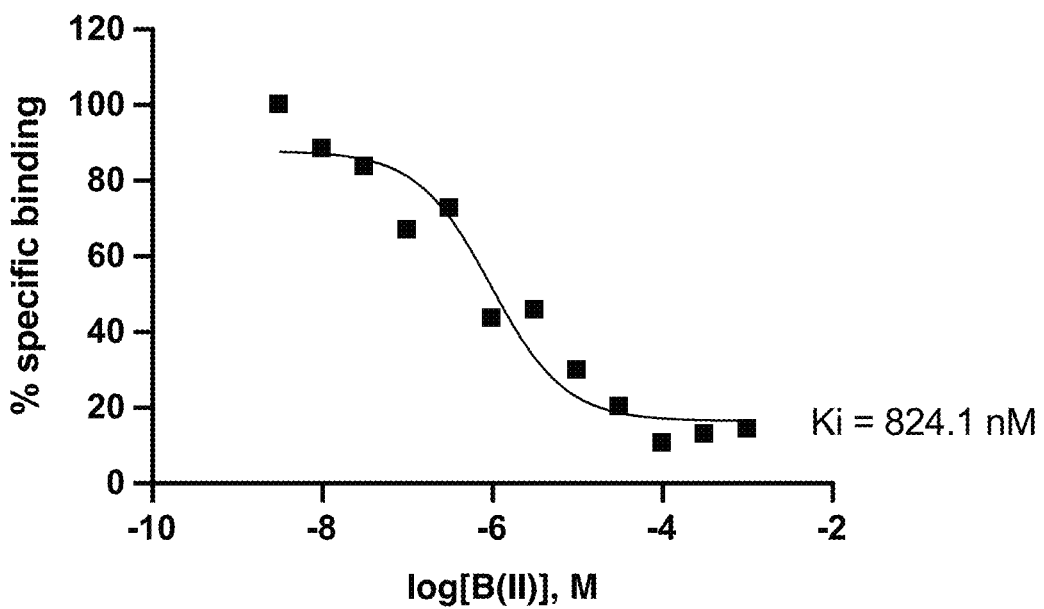

5-HT$_{1A}$ receptor. Competition assays were performed as follows: SPA beads (RPNQ0011), radiolabeled 8-hydroxy-DPAT [propyl-2,3-ring-1,2,3-$^3$H](labelled 7-(dipropylamino)-5,6,7,8-tetrahydronaphthalen-1-ol; NET929250UC), membranes containing 5-HT$_{1A}$ (6110501400UA), and isoplate-96 microplate (6005040)

were from Perkin Elmer (perkinelmer.com). Radioactive binding assays were carried out using a scintillation proximity assay (SPA; Maguire et al., 2012, Methods in Molecular Biology 897:31-77). For saturation binding assays, mixtures of 10 µg of membrane containing $HT_{1A}$ receptor was pre-coupled to 1 mg of SPA beads at room temperature in a tube rotator for 1 h in binding buffer [50 mM Tris-HCl pH 7.4, 10 mM magnesium sulfate, 0.5 mM EDTA, 3.7% (v/v) glycerol, 1 mM ascorbic acid, 10 µM pargyline HCl]. After pre-coupling, the beads and membrane were aliquoted in an isoplate-96 microplate with increasing amounts of 8-hydroxy-DPAT [propyl-2,3-ring-1,2,3-$^3$H] (0.1525 nM to 5 nM) and incubated for two hours at room temperature in the dark with shaking. After incubation, the samples were read on a MicroBeta 2 Microplate Counter (perkinelmer.com). Non-specific binding was carried out in the presence of 100 µM of metergoline (M3668-500MG, Sigma-Aldrich). Equilibrium binding constant for 8-hydroxy-DPAT ($K_D$) was determined from a saturation binding curve using one-site saturation binding analysis from GraphPad PRISM software (Version 9.2.0). Test compound was dissolved to 100 mM in dimethylsulfoxide (DMSO), and dilutions were carried out in assay buffer. Competition binding assays were performed using 0.5 nM hot 8-hydroxy-DPAT and different concentrations of DMSO (up to 1%), tryptophan (3 nM to 1 mM), or unlabelled test compounds (3 nM to 1 mM) similar to the saturation binding assay. $K_i$ values were calculated from the competition displacement data using the competitive binding analysis from GraphPad PRISM software. Serotonin was used as a positive control, as it is the natural, endogenous ligand for all serotonergic receptors. 2C-B, MDMA and mescaline were used as positive controls since they are phenylalkylamine-type molecules with relatively strong (2C-B; Rickli et al., 2015, Neuropharmacology 99: 546) or more moderate (MDMA, Simmler et al., 2013, British J. Pharmacol. 168: 458; mescaline, Rickli et al., 2016, Eur. Neuropharm. 26: 1327) 5-$HT_{1A}$ receptor binding activities, respectively. Escaline and proscaline were included in this study for comparative purposes, for although their 5-$HT_{1A}$ receptor binding mode(s) are understudied they are established mescaline-type hallucinogens with therapeutic potential (Shulgin and Shulgin, 1990. *PIHKAL: A Chemical Love Story*. 1$^{st}$ ed., Transform Press). Fluoxetine and vortioxetine were included as positive controls as they are widely prescribed pharmaceuticals with established binding to the 5-$HT_{1A}$ receptor (Owens et al., 1997, Journal of Pharmacology and Experimental Therapeutics 283:1305-1322; Celada et al., 2013, CNS Drugs 27:703-716). FIG. 14A illustrates the binding curve used to determine the $K_D$ of 8-hydroxy-DPAT. FIGS. 14B and 14C illustrate binding curves of negative controls DMSO and tryptophan, respectively. As seen in FIGS. 14B and 14C, data precluded $K_i$ determination (i.e., $K_i$>1000 µM) which indicated no binding for these negative controls. Binding curves illustrated in FIGS. 14D, 14E, 14F, and 14G reveal data permitting $K_i$ determinations for the positive controls: serotonin, mescaline, 2C-B, and MDMA respectively. The sigmoidal curves and $K_i$ values (i.e., $K_i$<1000 µM) in FIGS. 14D, 14E, 14F, and 14G reveal 5-$HT_{1A}$ receptor binding at indicated ligand concentrations. Data in FIGS. 14H and 14I suggest binding to 5-$HT_{1A}$ receptor of escaline and proscaline respectively, at the indicated concentrations. Data in FIGS. 14J and 14K indicate binding to the 5-$HT_{1A}$ receptor of fluoxetine and vortioxetine respectively. Data in FIG. 14L indicates binding to the 5-$HT_{1A}$ receptor of the compound with formula B(II) above levels observed for negative controls (FIGS. 14A and 14B). Resulting $K_i$ data for controls and test compounds in 5-$HT_{1A}$ receptor binding assays is summarized in Table 1.

Figure 15A:
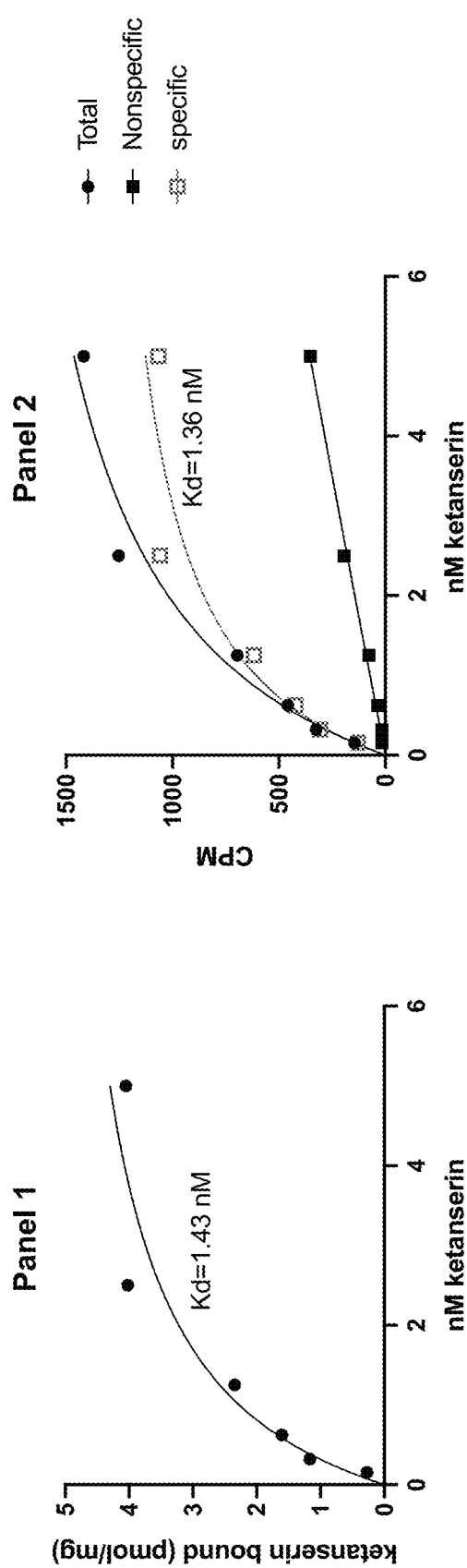
FIGS. 15A, 15B, 15C, 15D, 15E, 15F, 15G, and 15H depict various graphs representing certain experimental results, notably graphs obtained in the performance of experimental assays to evaluate the pharmaceutical efficacy of an example compound having chemical formula B(II), notably a radioligand 5-$HT_{2A}$ receptor saturated binding assay using radiolabeled [$^3$H-ketanserin] (binding curves) (FIG. 15A); a 5-$HT_{2A}$ receptor competition assay using psilocin (positive control) (FIG. 15B); a 5-$HT_{2A}$ receptor competition assay using tryptophan (negative control) (FIG. 15C); a 5-$HT_{2A}$ receptor competition assay using escaline (FIG. 15D); a 5-$HT_{2A}$ receptor competition assay using proscaline (FIG. 15E); a 5-$HT_{2A}$ receptor competition assay using 2C-B (positive control) (FIG. 15F); and a 5-$HT_{2A}$ receptor competition assay using MDMA (positive control) (FIG. 15G), and; a 5-$HT_{2A}$ receptor competition assay using the compound with formula B(II) (FIG. 15H).
Figure 15B:
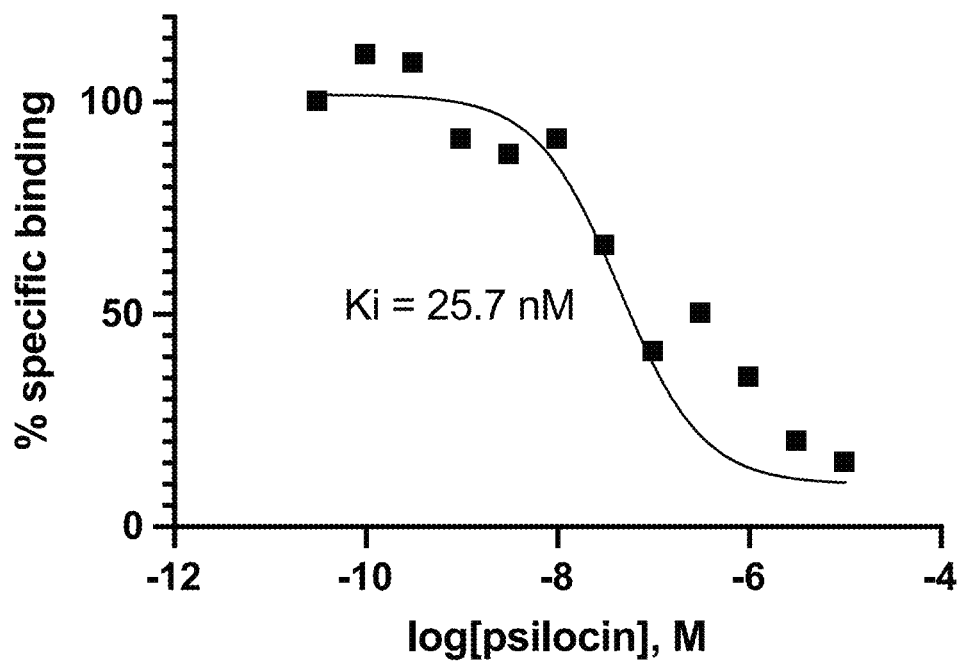
Figure 15C:
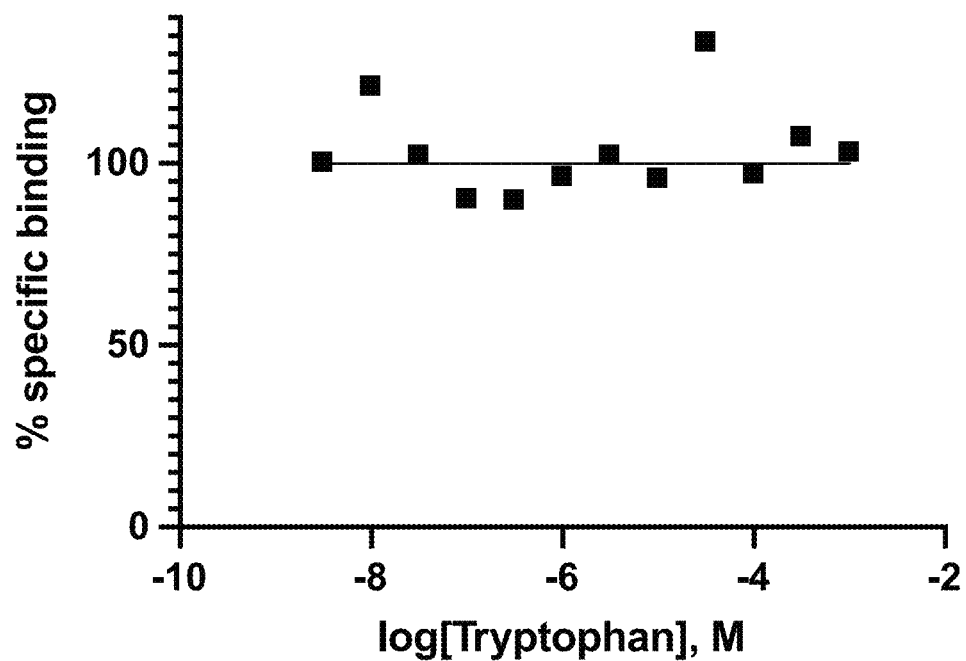
Figure 15D:
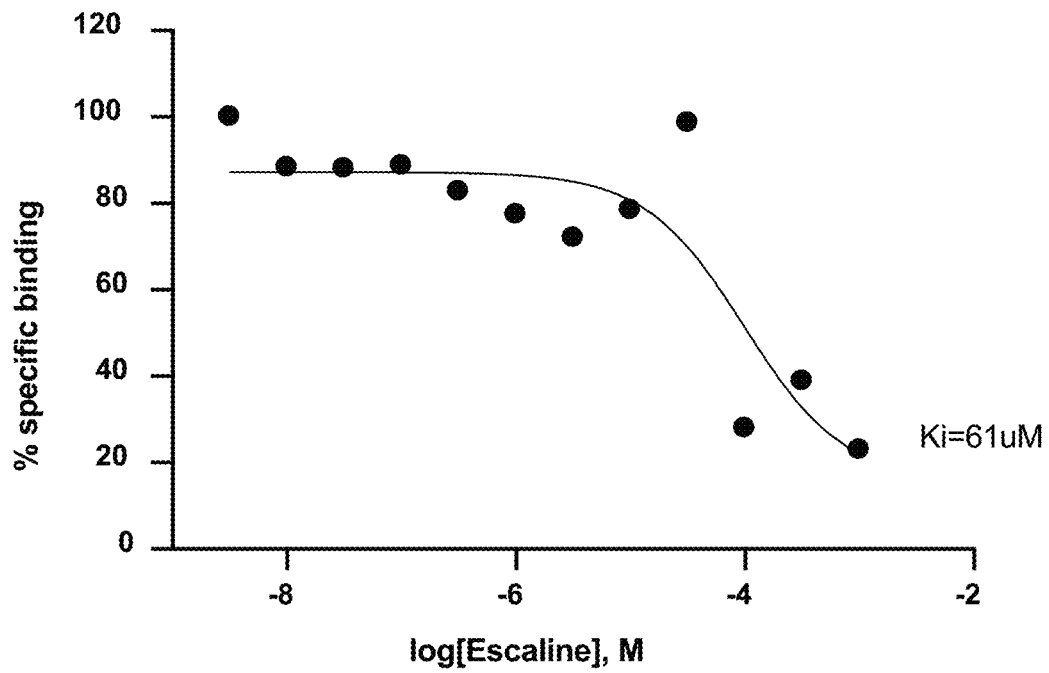
Figure 15E:
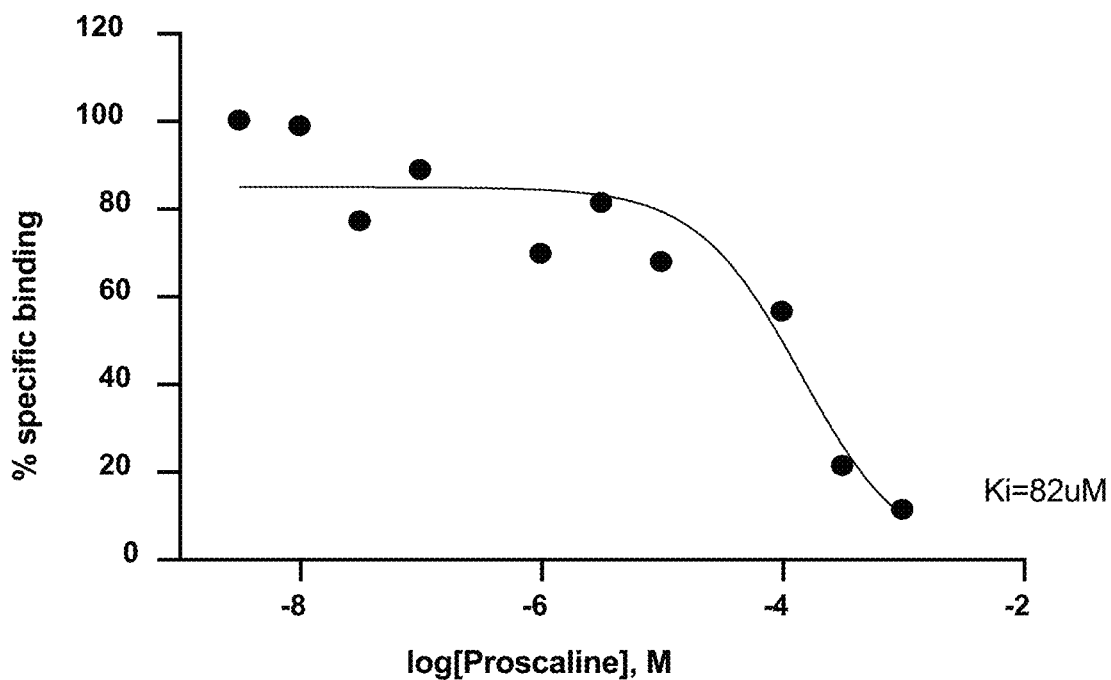
Figure 15F:
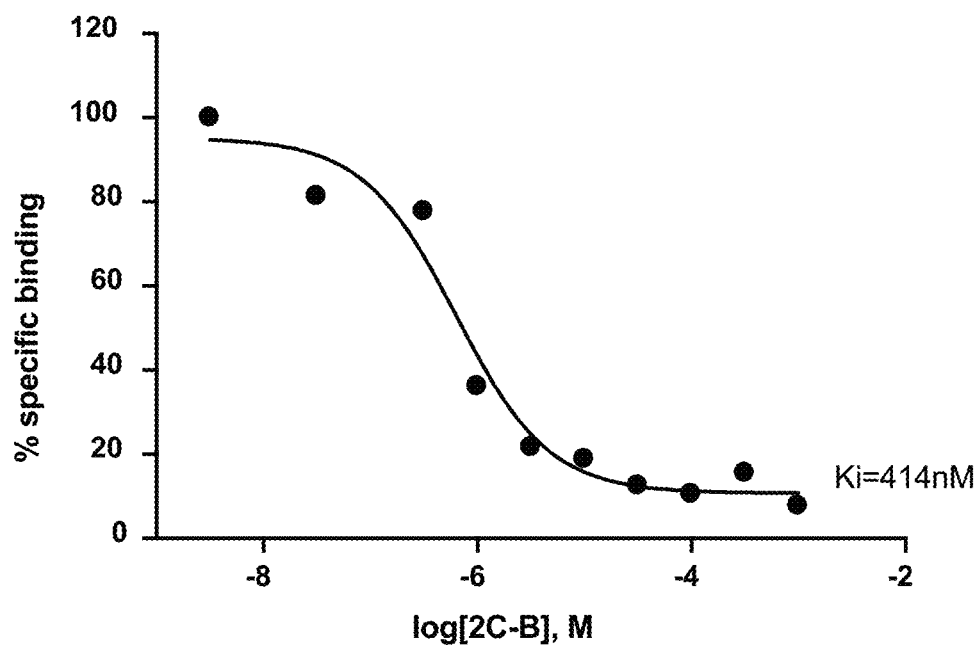
Figure 15G:
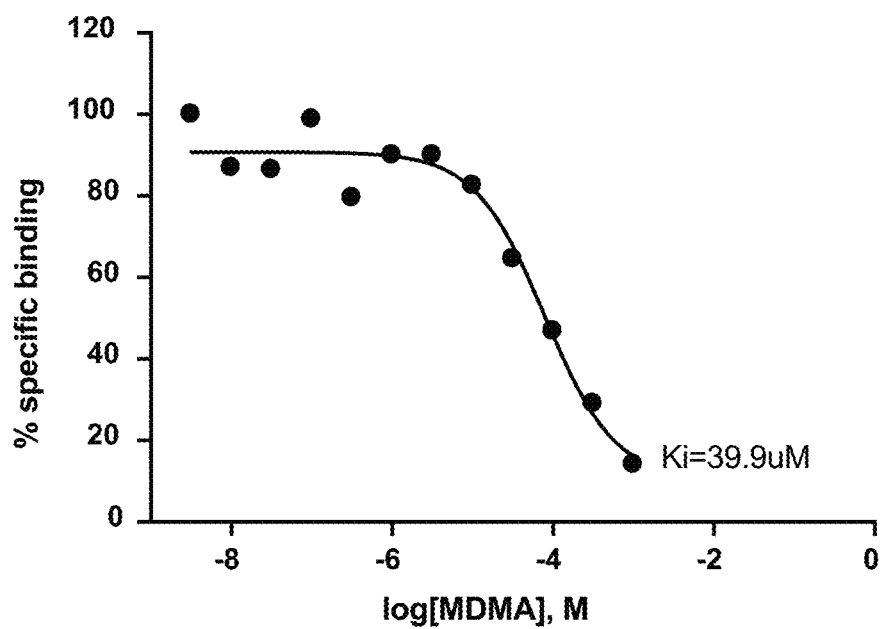
Figure 15H:
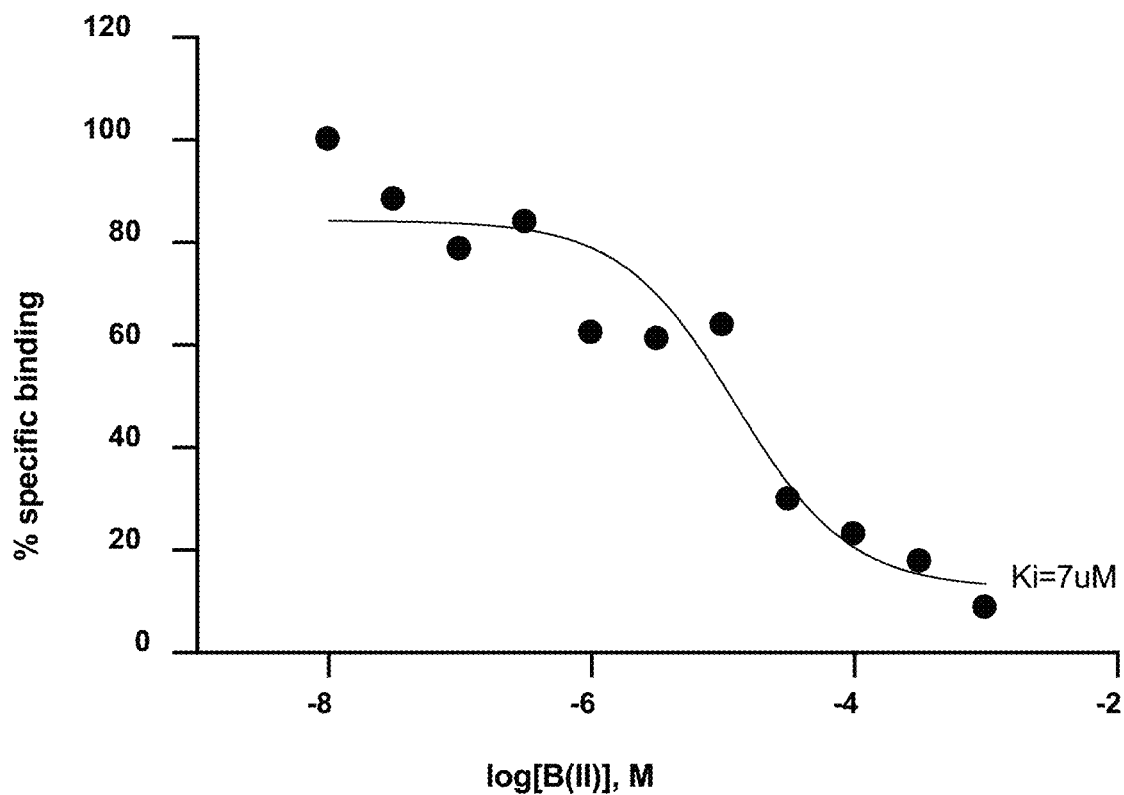

5-$HT_{2A}$ receptor. Competition assays were performed as for 5-$HT_{1A}$ assays with the following differences. SPA beads (RPNQ0010), [$^3$H]ketanserin (NET1233025UC), and membranes containing 5-$HT_{2A}$ (ES-313-M400UA) were from PerkinElmer. After pre-coupling, the beads and membrane were aliquoted in an isoplate-96 microplate with increasing amounts of [$^3$H]ketanserin (0.1525 nM to 5 nM). Determination of non-specific binding was carried out in the presence of 20 mM of spiperone (S7395-250MG, Sigma-Aldrich). Equilibrium binding constant for ketanserin ($K_d$) was determined from saturation binding curves using the 'one-site saturation binding analysis' method in GraphPad PRISM software (Version 9.2.0). Competition binding assays were performed using fixed (1 nM) [$^3$H]ketanserin and different concentrations of unlabeled test compounds (3 nM to 1 mM) similar to the saturation binding assay. Tryptophan was included as a negative control as it has no activity at the 5-$HT_{2A}$ receptor. In contrast, 2C-B and MDMA were used as positive controls since they are phenylalkylamine-type molecules with relatively strong (Marcher-Rørsted et al., 2020, ACS Chem. Neurosci. 11: 1238) or more moderate (Simmler et al., 2013, British J. Pharmacol. 168: 458) 5-$HT_{2A}$ receptor binding activities, respectively. Escaline and proscaline were included in this study for comparative purposes, for although their 5-$HT_{2A}$ receptor binding mode is understudied they are established mescaline-type hallucinogens known to induce head-twitch responses in mice (Halberstadt et al., 2019, J. Psychopharm. 33: 406-414). Mouse head-twitch response has been correlated with 5-$HT_{2A}$ receptor engagement (Halberstadt, 2015, Behav. Brain Res. 277: 99). Psilocin is included as an additional positive control as it exhibits well-established binding to 5-$HT_{2A}$ receptor as a partial agonist. FIG. 15A illustrates data in support of overall $K_D$ determination for ketanserin (Panel 1), in addition to the $K_D$ owed to specific binding (Panel 2). FIG. 15B illustrates data obtained for psilocin and supports binding at the 5-$HT_{2A}$ receptor for this positive control. FIG. 15C illustrates data obtained for tryptophan and supports a lack of binding at the 5-$HT_{2A}$ receptor for this negative control. FIGS. 15D and 15E reveal binding data for escaline and proscaline, respectively, and resulting $K_i$ values (i.e., <1000 µM) reveal binding at the 5-$HT_{2A}$ receptor at indicated concentrations. FIG. 15F reveals binding data for 2C-B and the resulting $K_i$ value (i.e., <1000 µM) reveals binding at the 5-$HT_{2A}$ receptor. FIG. 15G reveals binding data for MDMA and the resulting $K_i$ value (i.e., <1000 µM) reveals binding at the 5-$HT_{2A}$ receptor at the indicated concentrations. Data in FIG. 15H indicates binding to the 5-$HT_{2A}$ receptor of the compound with formula B(II) above levels observed for negative control (FIG. 15C). Resulting $K_i$ data for controls and test compounds in 5-$HT_{2A}$ receptor binding assays is summarized in Table 1.

TABLE 1

Data summary for 5-$HT_{1A}$ and 5-$HT_{2A}$ receptors radioligand competition assays.

| Molecule | 5-$HT_{1A}$, $K_i$ (µM) | 5-$HT_{2A}$, $K_i$ (µM) |
| --- | --- | --- |
| DMSO | >1000 | >1000 |
| tryptophan | >1000 | >1000 |
| serotonin | 0.0025 | N.D. |
| psilocin | N.D. | 0.0257 |
| mescaline | 8.5 | N.D. |

TABLE 1-continued

Data summary for 5-HT$_{1A}$ and 5-HT$_{2A}$ receptors radioligand competition assays.

| Molecule | 5-HT$_{1A}$, K$_i$ (µM) | 5-HT$_{2A}$, K$_i$ (µM) |
|---|---|---|
| 2C-B | 0.200 | 0.414 |
| MDMA | 11 | 39.9 |
| escaline | 12.4 | 61 |
| proscaline | 9.4 | 82 |
| fluoxetine | 0.306 | N.D. |
| vortioxetine | 0.0043 | N.D. |
| D(I) | 11 | 21 |
| B(II) | 824 | 7 |
| F(III) | >1000 | 152 |
| F(IV) | 84.5 | N.D. |
| C(III) | 2.33 | N.D. |
| C(IV) | 0.596 | N.D. |
| A(II) | 8.0 | N.D. |
| C(I) | 2.9 | N.D. |
| F(V) | 363.5 | N.D. |
| C(V) | 5.0 | N.D. |

N.D. = not determined

Functional Receptor Potency Assays.

Figure 16A:
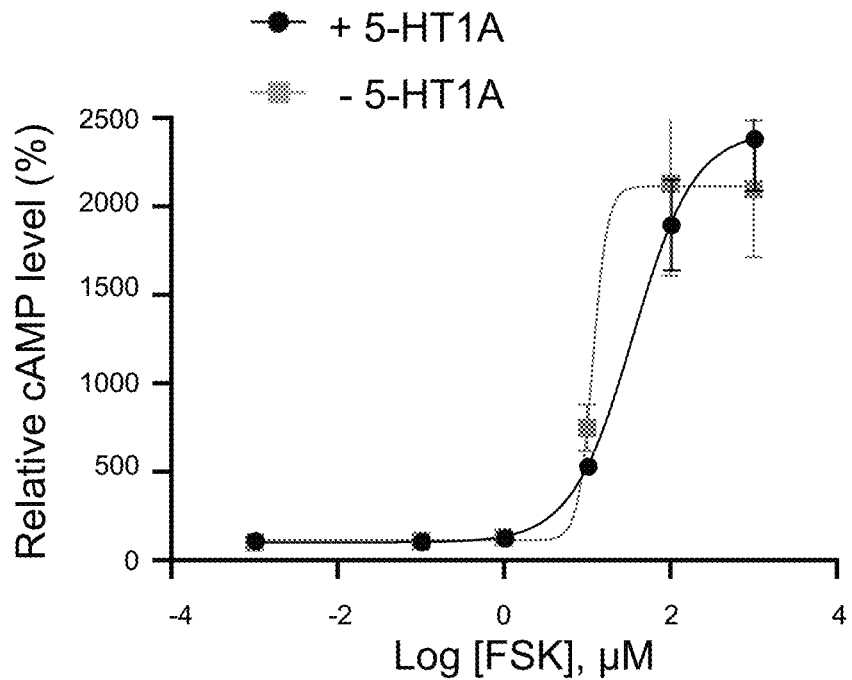
FIGS. 16A, 16B, 16C, 16D, 16E, 16F, 16G, and 16H depict various graphs representing certain experimental results, notably graphs obtained in the performance of experimental assays to evaluate the pharmaceutical efficacy of an example compound having chemical formula B(II), notably a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with varying amounts of forskolin (FIG. 16A); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 µM forskolin and varying amounts of 8-OH-DPAT (FIG. 16B); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 µM forskolin and varying amounts of serotonin (FIG. 16C); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 µM forskolin and varying amounts of psilocin (FIG. 16D); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 µM forskolin and varying amounts of mescaline (FIG. 16E); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 µM forskolin and varying amounts of MDMA (FIG. 16F); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 µM forskolin and varying amounts of 2C-B (FIG. 16G); and a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 µM forskolin and varying amounts of compound B(II) (FIG. 16H).
Figure 16B:
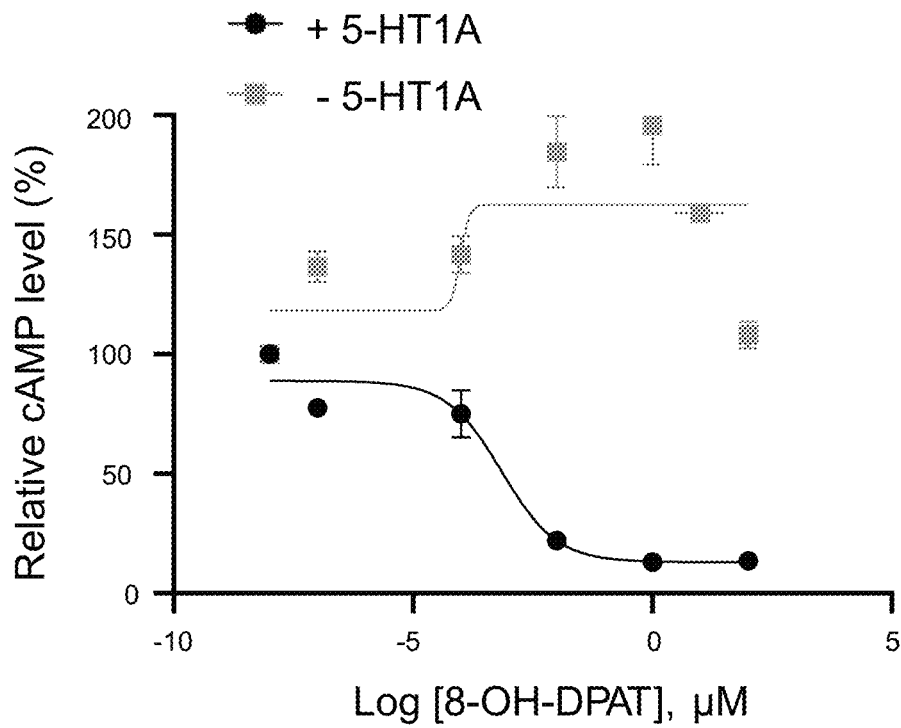
Figure 16C:
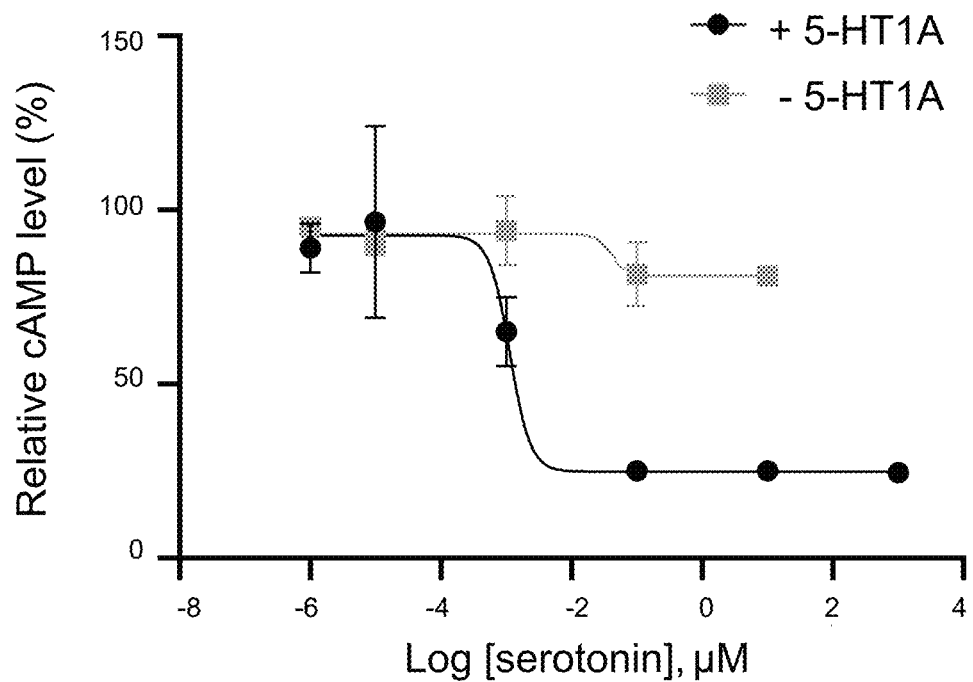
Figure 16D:
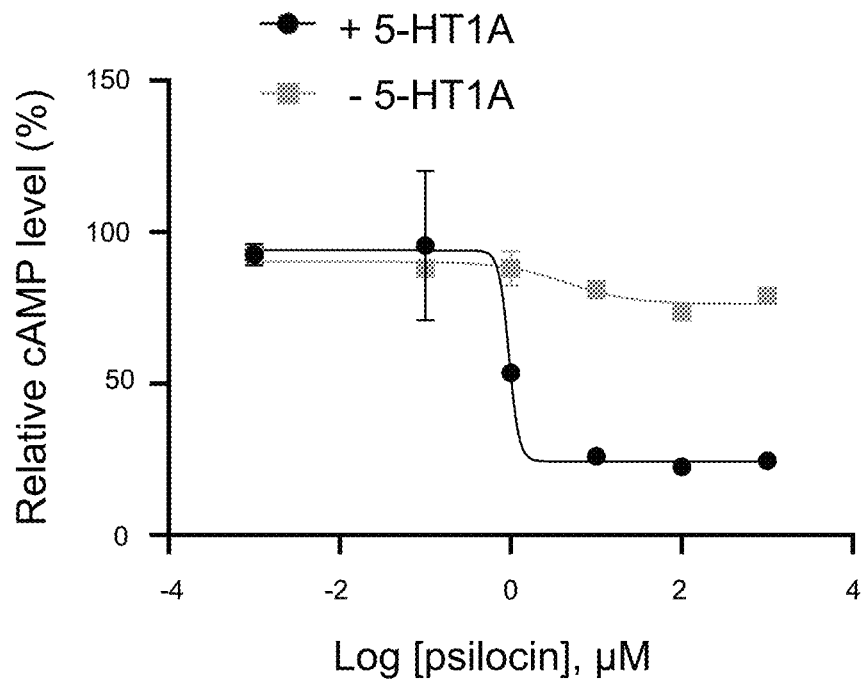
Figure 16E:
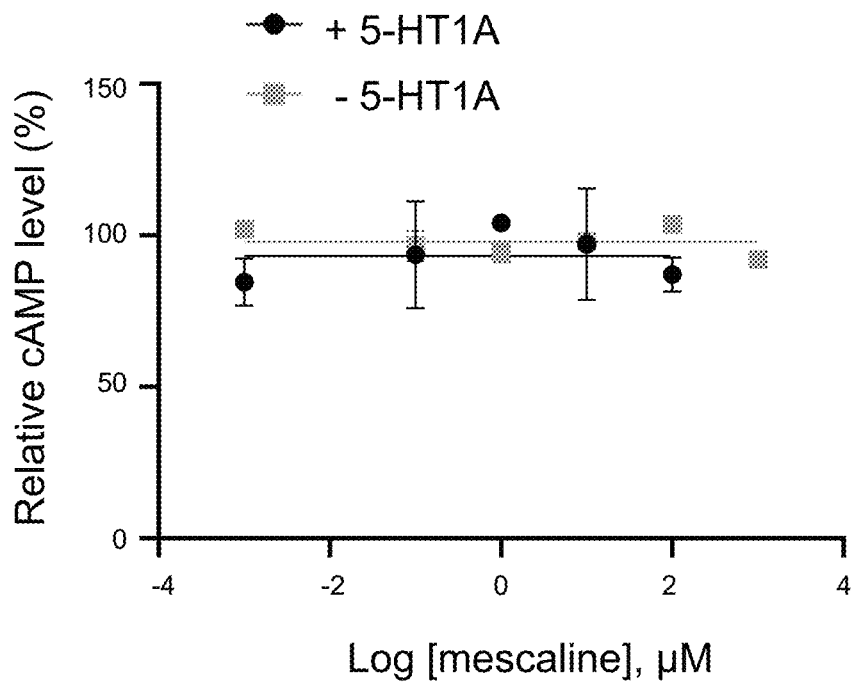
Figure 16F:
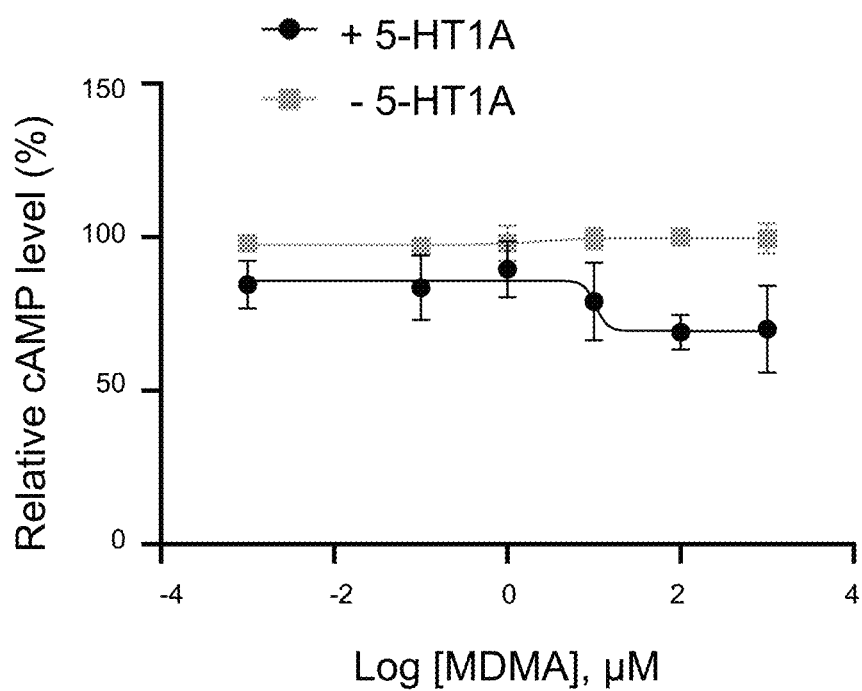
Figure 16G:
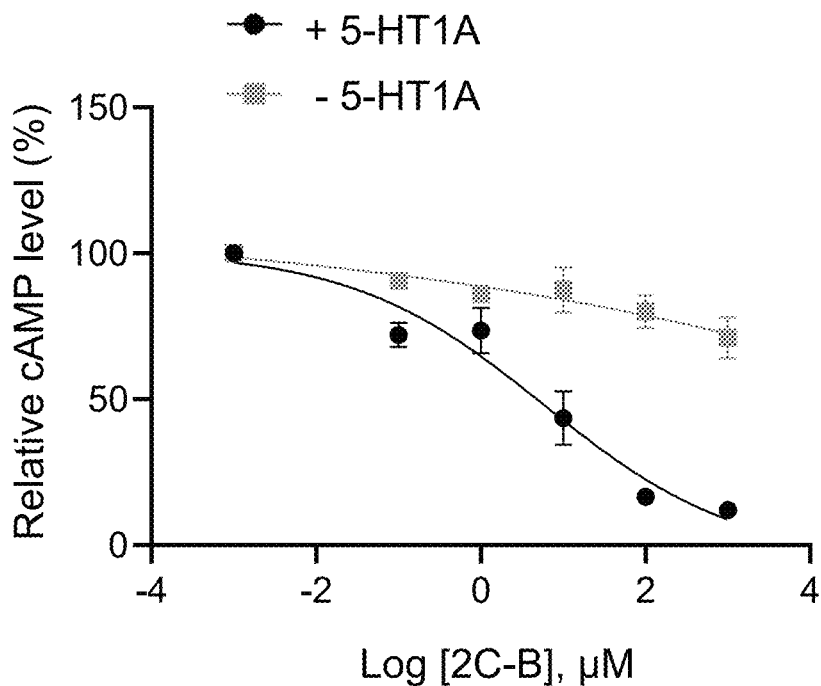
Figure 16H:
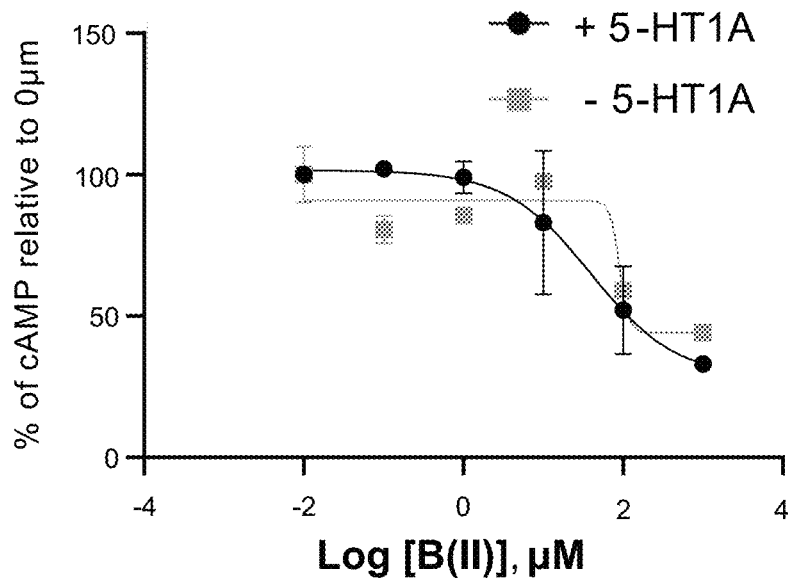

5-HT$_{1A}$ receptor. The Chinese hamster ovary (CHO)-derived cell line, CHO-K1/5-HT$_{1A}$/Gα15 (GenScript M00330), stably transformed to express 5-HT$_{1A}$ serotonin receptor, was used to evaluate specific agonist-mediated stimulation of 5-HT$_{1A}$ signal transduction. In these non-neuronal cells, stimulation of 5-HT$_{1A}$ activates the Gα$_{i/o}$ protein leading to inhibition of adenylyl cyclase (AC) type I (Rojas and Felder, 2016, Frontiers in Cellular Neuroscience 10:272; Polter and Li, 2010, Cell Signalling 22:1406-1412). In cells stimulated with 4 µM forskolin, which directly stimulates AC to elevate intracellular cAMP levels, 5-HT$_{1A}$ activation was assessed quantitatively by measuring reduced intracellular cAMP levels. All cells were grown and maintained as a monolayer in Ham's F12 nutrient mix supplemented with 10% fetal bovine serum (FBS), 200 µg/mL zeocin or 100 µg/mL hygromycin, all obtained from ThermoFisher Scientific and used according to the manufacturer's instructions. Cells were cultured and incubated at 37° C. in a humidified oxygen atmosphere with 5% CO$_2$. To evaluate the activation of 5-HT$_{1A}$ signal transduction, cells were first seeded in tissue culture-treated, white-walled, clear-bottom 96-well plates (Corning, corning.com) at a density of 30,000 cells/well in 100 mL complete growth media. Cells were cultured for 24 h in a humidified incubator at 37° C. and 5% CO$_2$. Cells were then stimulated for 20 min with test compounds, prepared in titration beginning at 1 mM and dissolved in an induction medium (serum-free culture medium containing 4 µM forskolin (Sigma-Aldrich), 500 µM isobutyl-1-methylxanthine (IBMX, Sigma-Aldrich) and 100 µM RO 20-1724 (Sigma-Aldrich). Changes in intracellular cAMP levels were measured using the commercially available cAMP-Glo Assay Kit (Promega, promega.ca) following the manufacturers protocol. The level of luminescence derived from cells stimulated with induction medium alone was used to establish the max level of intracellular cAMP (100%) for each assay run. FIG. 16A shows increasing levels of cAMP in cultured cells incubated with increasing concentrations of forskolin (FSK) independent of 5-HT$_{1A}$ expression. FIG. 16B illustrates reduction in cAMP levels in 5-HT$_{1A}$ receptor expressing cells (+5-HT$_{1A}$) stimulated with 4 µM forskolin as levels of 8-OH-DPAT increase, indicating 5-HT$_{1A}$ receptor binding by 8-OH-DPAT in these cells. Conversely, this trend of decreasing % cAMP levels with increasing 8-OH-DPAT is not observed in cells lacking expression of 5-HT$_{1A}$ receptor. 8-OH-DPAT (7-(dipropylamino)-5,6,7,8-tetrahydronaphthalen-1-ol) is a well-established full agonist of the 5-HT$_{1A}$ receptor (Larsson et al., 1990, Neuropharmacology 29:85-91), and was included as a positive control to ensure functionality of the cellular response system. FIG. 16C illustrates reduction in cAMP levels in 5-HT$_{1A}$ receptor expressing cells (+5-HT$_{1A}$) stimulated with 4 µM forskolin as levels of serotonin increase, indicating 5-HT$_{1A}$ receptor binding by serotonin in these cells. Conversely, this trend of decreasing % cAMP levels with increasing serotonin is not observed in cells lacking expression of 5-HT$_{1A}$ receptor. Serotonin is the innate ligand of the 5-HT$_{1A}$ receptor and was thus included as a positive control. Psilocin, MDMA and 2C-B were included as calibrator compounds, since whereas these compounds are all known to bind 5-HT$_{1A}$ receptor to various degrees (Marcher-Rørsted et al., 2020, ACS Chem. Neurosci. 11: 1238; Simmler et al., 2013, British J. Pharmacol. 168: 458) their ability to elicit a cellular response in this particular functional assay is unknown. The binding mode of mescaline to the 5-HT$_{1A}$ receptor remains understudied but owing to the structural similarity of its phenylethylamine-type backbone to other derivatives within this application, it was included for comparative purposes. FIG. 16D illustrates reduction in cAMP levels in 5-HT$_{1A}$ receptor expressing cells (+5-HT$_{1A}$) stimulated with 4 mM forskolin as levels of psilocin increase, indicating 5-HT$_{1A}$ receptor binding by psilocin in these cells. Conversely, this trend of decreasing % cAMP levels with increasing psilocin is not observed in cells lacking expression of 5-HT$_{1A}$ receptor. FIG. 16E and FIG. 16F illustrate mild or no change in cAMP levels in 5-HT$_{1A}$ receptor expressing cells (+5-HT$_{1A}$) stimulated with 4 µM forskolin as levels of mescaline and MDMA increase, respectively. These results indicate mild or no 5-HT$_{1A}$ receptor engagement by mescaline or MDMA in this cellular system, respectively. FIG. 16G illustrates reduction in cAMP levels in 5-HT$_{1A}$ receptor expressing cells (+5-HT$_{1A}$) stimulated with 4 mM forskolin as levels of 2C-B increase, indicating 5-HT$_{1A}$ receptor engagement by 2C-B in these cells. Conversely, this trend of decreasing % cAMP levels with increasing 2C-B is not observed in cells lacking expression of 5-HT$_{1A}$ receptor. 5-HT$_{1A}$ receptor engagement evaluation for the compound designated B(II) is shown in FIG. 16H. Comparison of data acquired in +5-HT$_{1A}$ cultures with those acquired in −5-HT$_{1A}$ cultures indicates receptor modulation at elevated ligand concentrations (EC$_{50}$=40.1 µM). Table 2 summarizes EC$_{50}$ data for all control, calibrator, and test compounds acquired using this functional 5-HT$_{1A}$ receptor assay.

TABLE 2

Data summary for functional 5-HT$_{1A}$ receptor assay.

| Molecule | 5-HT$_{1A}$, EC$_{50}$ (µM) |
|---|---|
| 5-OH-DPAT | 0.0007118 |
| serotonin | 0.001142 |
| psilocin | 0.9567 |
| mescaline | >1000 |
| 2C-B | 5.945 |
| MDMA | >1000 |
| D(I) | >1000 |
| B(II) | 40.1 |
| F(V) | 10.0 |
| C(V) | 116.3 |
| G(V) | 129.5 |
| C(XIII) | 22.95 |

In Vitro Survey of Pharmacological Interaction Profiles at Receptors and Transporters Linked to Targeted Health Conditions.

To expand pharmacological profiling to include a broader range of targets with known involvement in, or connection to, brain neurological disorders, the compound with formula B(II) was evaluated with respect to binding and/or interaction at 9 different receptors and transporters. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A (5-HTR$_{1A}$), HTR2A (5-HTR$_{2A}$), HTR2B (5-HT$_{2B}$), HTR2C (5-HT$_{2C}$), HTR7 (5-HT$_7$), alpha2A ($\alpha_{2A}$), MT1 (MT$_1$), D3 (D$_3$)) and 3 transporters (SERT, DAT, NET). Assay conditions are summarized in Tables 3 and 4 for GPCR and transporters, respectively. On-site positive controls are routinely applied as part of standard industry practice at Eurofins Cerep (https://www.eurofins.com/contact-us/world-wide-interactive-map/france/eurofins-cerep-france/) to ensure functionality of each assay. To further calibrate each assay specifically for compounds bearing the phenylalkylamine (PAA) structural scaffold, a suite of six, PAA-type calibrator compounds were additionally submitted for assays: MDMA, mescaline, 2C-B, escaline, proscaline, and DOB. Additional tryptamine-type calibrators employed in these assays included serotonin and melatonin. Tryptophan was submitted as a negative control for all assays, as tryptophan is not known to interact with any of the target receptors or transporters. Seven widely marketed pharmaceuticals used in the treatment of mental health disorders with long-established pharmacological profiles were additionally submitted for assay calibration purposes: vortioxetine, trazodone, duloxetine, imipramine, agomelatine, bupropion, and vilazodone. Results for all calibrator compounds, control compounds, and test compounds including the compound with formula B(II) are summarized in Table 5.

TABLE 3

Conditions summary for GPCR (receptor) binding assays.
Cold ligand is included in assays to ensure only specific binding is evaluated.

| Receptor | Hot ligand Name | Hot ligand Type | Concentration nM | K$_d$ nM | Cold ligand* Name | Cold ligand* µM | Incubation min/° C. |
|---|---|---|---|---|---|---|---|
| alpha2A | [$^3$H]RX 821002 | Antagonist | 1 | 0.8 | (−)epinephrine | 100 | 60/20 |
| D$_3$ | [$^3$H]methylspiperone | Antagonist | 0.25 | 0.25 | (+)butaclamol | 10 | 60/RT |
| MT1 (ML1A) | [$^{125}$I]2-iodomelatonin | Agonist | 0.01 | 0.04 | melatonin | 1 | 240/20 |
| 5-HT$_{1A}$ | [$^3$H]8-OH-DPAT | Agonist | 0.5 | 0.5 | 8-OH-DPAT | 10 | 60/RT |
| 5-HT$_{2A}$ | [$^{125}$I](±)DOI | Agonist | 0.1 | 0.3 | (±)DOI | 1 | 60/RT |
| 5-HT$_{2B}$ | [$^3$H]mesulergine | Antagonist | 2 | 2.4 | SB206553 | 10 | 60/20 |
| 5-HT$_{2C}$ | [$^{125}$I](±)DOI | Agonist | 0.1 | 0.9 | (±)DOI | 10 | 60/37 |
| 5-HT$_7$ | [$^3$H]LSD | Agonist | 4 | 2.3 | serotonin | 10 | 120/20 |

TABLE 4

Conditions summary for transporter binding assays.
Cold ligand is included in assays to ensure only specific binding is evaluated.

| Transporter | Hot ligand Name | Hot ligand Type | Concentration nM | K$_d$ nM | Cold ligand* Name | Cold ligand* µM | Incubation min/° C. |
|---|---|---|---|---|---|---|---|
| SERT | [$^3$H]imipramine | Antagonist | 2 | 1.7 | imipramine | 10 | 60/RT |
| NET | [$^3$H]nisoxetine | Antagonist | 1 | 2.9 | desipramine | 1 | 120/4 |
| DAT | [$^3$H]BTCP | Antagonist | 4 | 4.5 | BTCP | 10 | 120/4 | i. Competition Assay to Measure Binding Affinity at Alpha2A Receptor.

Assays were conducted according to methodology described by Langin et al., [Eur. J. Pharmacol. 167:95-104, 1989] using conditions summarized in Table 3. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using 100 µL membrane suspension incubated with radioligand, cold ligand to ensure specific binding by test ligand, and test molecule (10 µM) in 400 µL final volume of Tris-$Mg^{2+}$ buffer. Incubations were quenched with the addition of 4 mL ice cold washing buffer (10 mM Tris-HCl, 0.5 mM $MgCl_2$). Bound and free radioligand were separated by filtration through GF/C Whatman filters under vacuum. The filters were then washed and subjected to scintillation counting. Results were expressed as a percent of control-specific binding ([measured specific binding/control-specific binding]*100). Results for the compound with formula B(II) are shown in Table 5.

ii. Competition Assay to Measure Binding Affinity at D3 Receptor.

Assays were conducted according to methodology described by Mackenzie et al., [Eur. J. Pharmacol. 266:79-85, 1994] using conditions summarized in Table 3. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using 100 µL membrane suspension, radioligand, cold ligand to ensure specific binding by test ligand, and test molecule (10 µM) in a final volume of 400 µL. Bound and free radioligand were separated by filtration through GF/C Whatman filters under vacuum. The filters were then washed and subjected to scintillation counting. Results were expressed as a percent of control-specific binding ([measured specific binding/control-specific binding]*100). Results for the compound with formula B(II) are shown in Table 5.

iii. Competition Assay to Measure Binding Affinity at $MT_1$ Receptor.

Assays were conducted according to methodology described by Witt-Endersby and Dubocovich [Mol. Pharmacol. 50:166-174, 1996] using conditions summarized in Table 3. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using 100 µL membrane suspension, radioligand, cold ligand to ensure specific binding by test ligand, and test molecule (10 µM) in a final volume of 500 µL. Bound and free radioligand were separated by filtration through GF/C Whatman filters under vacuum. The filters were then washed and subjected to scintillation counting. Results were expressed as a percent of control-specific binding ([measured specific binding/control-specific binding]*100). Results for the compound with formula B(II) are shown in Table 5.

iv. Competition Assay to Measure Binding Affinity at $5\text{-HT}_{1A}$ Receptor.

Assays were conducted according to methodology described by Mulheron et al., [J. Biol. Chem. 269: 12954-12962, 1994] using conditions summarized in Table 3. As the purpose of this experiment was to gauge general binding potential of test ligand, rather than obtain detailed binding information yielding $K_i$ values, only a single concentration of test ligand was used (10 µM). Briefly, HEK-293 cells were used to express recombinant receptor, and membrane preparation was conducted at 4° C. Binding experiments were conducted using radioligand, 30 µg protein (membrane suspension), cold ligand to ensure specific binding by test ligand, and test molecule (10 µM) to final volume of 200 µL. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula B(II) are shown in Table 5.

v. Competition Assay to Measure Binding Affinity at $5\text{-HT}_{2A}$ Receptor.

Assays were conducted according to the methodology described by Bryant et al., [Life Sci. 15:1259-1268, 1996] using conditions summarized in Table 3. Briefly, HEK-293 cells were used to express recombinant receptor, and membrane preparation was conducted at 4° C. Binding experiments were conducted using radioligand, 30 µg protein (membrane suspension), cold ligand to ensure specific binding by test ligand, and test molecule (10 µM) to final volume of 300 µL. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula B(II) are shown in Table 5.

vi. Competition Assay to Measure Binding Affinity at $5\text{-HT}_{2B}$ Receptor.

Assays were conducted according to methodology described by Kursar et al., [Mol. Pharmacol. 46: 227-234, 1994] using conditions summarized in Table 3. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using radioligand, 0.2 mL (~100 µg protein) membrane suspension, cold ligand to ensure specific binding by test ligand, and test molecule (10 µM) in 50 mM Tris pH 7.4. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula B(II) are shown in Table 5.

vii. Competition Assay to Measure Binding Affinity at $5\text{-HT}_{2C}$ Receptor.

Assays were conducted according to methodology described by Bryant et al., [Life Sci. 15: 1259-1268, 1996] using conditions summarized in Table 3. As the purpose of this experiment was to gauge general binding potential of test ligand, rather than obtain detailed binding information yielding $K_i$ values, only a single concentration of test ligand was used (10 µM). Briefly, HEK-293 cells were used to express recombinant receptor, and membrane preparation was conducted at 4° C. Binding experiments were conducted using radioligand, 0.2 mL (~100 µg protein) membrane suspension, cold ligand to ensure specific binding by test ligand, and test molecule (10 µM) to final volume of 800 µL with 3 mM CaCl$_2$), 0.1% sodium ascorbate, and 50 mM Tris pH 7.4. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula B(II) are shown in Table 5.

viii. Competition Assay to Measure Binding Affinity at 5-HT$_7$ Receptor.

Assays were conducted according to methodology described by Shen et al., [J. Biol. Chem. 268: 18200-18204, 1993] using conditions summarized in Table 3. As the purpose of this experiment was to gauge general binding potential of test ligand, rather than obtain detailed binding information yielding K$_i$ values, only a single concentration of test ligand was used (10 µM). Briefly, HEK-293 cells were used to express recombinant receptor, and membrane preparation was conducted at 4° C. Binding experiments were conducted using radioligand, 30 µg protein (membrane suspension), cold ligand to ensure specific binding by test ligand, and test molecule (10 µM) to final volume of 200 µL. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula B(II) are shown in Table 5.

ix. Competition Assay to Measure Binding Affinity at Serotonin Transporter (SERT).

Assays were conducted according to methodology described by Tatsumi et al., [Eur J Pharmacol 368: 277-283, 1999] using conditions summarized in Table 4. As the purpose of this experiment was to gauge general binding potential of test ligand, rather than obtain detailed binding information yielding K$_i$ values, only a single concentration of test ligand was used (10 µM). Briefly, CHO cells were used to express recombinant transporter, and membrane preparation was conducted at 4° C. Binding experiments were conducted using radioligand, 30 µg protein (membrane suspension), cold ligand to ensure specific binding by test ligand, and test molecule (10 µM) to final volume of 200 µL. Bound and free radioligand were separated by filtration through Whatman glass fibre filters under vacuum. The filters were then washed and subjected to scintillation counting. Results were expressed as a percent of control-specific binding ([measured specific binding/control-specific binding]*100). Results for the compound with formula B(II) are shown in Table 5.

x. Competition Assay to Measure Binding Affinity at Norepinephrine Transporter (NET).

Assays were conducted according to methodology described by Pacholczyk et al., [Nature 350: 350-354, 1991] using conditions summarized in Table 4. As the purpose of this experiment was to gauge general binding potential of test ligand, rather than obtain detailed binding information yielding K$_i$ values, only a single concentration of test ligand was used (10 µM). Briefly, CHO cells were used to express recombinant transporter, and membrane preparation was conducted at 4° C. Binding experiments were conducted using radioligand, 30 µg protein (membrane suspension), cold ligand to ensure specific binding by test ligand, and test molecule (10 µM) to final volume of 200 µL. Bound and free radioligand were separated by filtration through Whatman glass fibre filters under vacuum. The filters were then washed and subjected to scintillation counting. Results were expressed as a percent of control-specific binding ([measured specific binding/control-specific binding]*100). Results for the compound with formula B(II) are shown in Table 5.

xi. Competition Assay to Measure Binding Affinity at Dopamine Transporter (DAT).

Assays were conducted according to methodology described by Pristupa et al., [Mol. Pharmacol. 45: 125-135, 1994] using conditions summarized in Table 4. As the purpose of this experiment was to gauge general binding potential of test ligand, rather than obtain detailed binding information yielding K$_i$ values, only a single concentration of test ligand was used (10 µM). Briefly, CHO cells were used to express recombinant transporter, and membrane preparation was conducted at 4° C. Binding experiments were conducted using radioligand, 50 µg protein (membrane suspension), cold ligand to ensure specific binding by test ligand, and test molecule (10 µM) to final volume of 200 µL. Bound and free radioligand were separated by filtration through Whatman glass filters under vacuum. The filters were then washed and subjected to scintillation counting. Results were expressed as a percent of control-specific binding ([measured specific binding/control-specific binding]*100). Results for the compound with formula B(II) are shown in Table 5.

TABLE 5

Results for GPCR and transporter competition-based binding assays. Data is shown as percent of control-specific binding.

| Compound | HT1A | HT2A | HT2B | HT2C | HT7 | α-2A | D$_3$ | SERT | DAT | MT1 | NET |
|---|---|---|---|---|---|---|---|---|---|---|---|
| MDMA | 68 | 74 | 85 | 96 | 58 | 27 | 18 | 46 | 28 | 1 | 3 |
| Mescaline | 65 | 79 | 80 | 95 | 38 | 57 | −13 | −6 | −1 | 6 | −9 |
| 2C-B | 96 | 98 | 99 | 98 | 88 | 88 | 43 | 42 | 5 | 86 | 13 |
| Escaline | 44 | 84 | 81 | 95 | 16 | 45 | 0 | 0 | 0 | 0 | 6 |
| Proscaline | 71 | 91 | 85 | 97 | 5 | 40 | 4 | 23 | −2 | 3 | −9 |
| DOB | 75 | 100 | 97 | 98 | 65 | 66 | 25 | 53 | 3 | −3 | 6 |
| Serotonin | 100 | 100 | 96 | 102 | 100 | 18 | 73 | 80 | 8 | 7 | −3 |
| Melatonin | 46 | −1 | 52 | 19 | 8 | −7 | 2 | 7 | 4 | 98 | −2 |
| Tryptophan | 6 | −1 | 0 | 25 | 11 | −4 | −23 | 1 | 1 | −2 | 1 |
| Vortioxetine | 99 | 90 | 97 | 99 | 100 | 62 | 88 | 101 | 90 | 26 | 99 |
| Trazodone | 97 | 100 | 97 | 93 | 99 | 91 | 89 | 93 | 24 | 14 | −1 |
| Duloxetine | 95 | 95 | 95 | 92 | 94 | 54 | 66 | 100 | 94 | 23 | 99 |

TABLE 5-continued

Results for GPCR and transporter competition-based binding assays. Data is shown as percent of control-specific binding.

| Compound | HT1A | HT2A | HT2B | HT2C | HT7 | α-2A | $D_3$ | SERT | DAT | MT1 | NET |
|---|---|---|---|---|---|---|---|---|---|---|---|
| Imipramine | 34 | 97 | 94 | 98 | 93 | 57 | 92 | 98 | 23 | 29 | 99 |
| Agomelatine | 58 | 61 | 93 | 92 | 20 | 2 | 6 | 30 | 1 | 99 | 1 |
| Bupropion | −1 | 12 | −2 | 1 | 4 | 2 | 3 | 25 | 92 | 83 | 12 |
| Vilazodone | 99 | 94 | 96 | 92 | 83 | 65 | 99 | 100 | 98 | 84 | 99 |
| D(I) | 49 | 32 | 58 | 33 | 18 | 34 | 21 | 70 | 39 | 10 | 17 |
| B(II) | 79 | 53 | 87 | 45 | 68 | 75 | 55 | 95 | 69 | 20 | 43 |
| F(III) | 0 | 0 | 13 | 5 | 2 | 5 | 0 | 0 | 0 | 12 | 0 |
| F(IV) | 37 | 0 | 26 | 8 | 0 | 4 | 12 | 0 | 0 | 42 | 0 |
| C(III) | 72 | 37 | 47 | 33 | 15 | 36 | 22 | 19 | 27 | 3 | 3 |
| C(IV) | 92 | 62 | 73 | 65 | 40 | 55 | 61 | 31 | 10 | 8 | 0 |

Figure 6A:
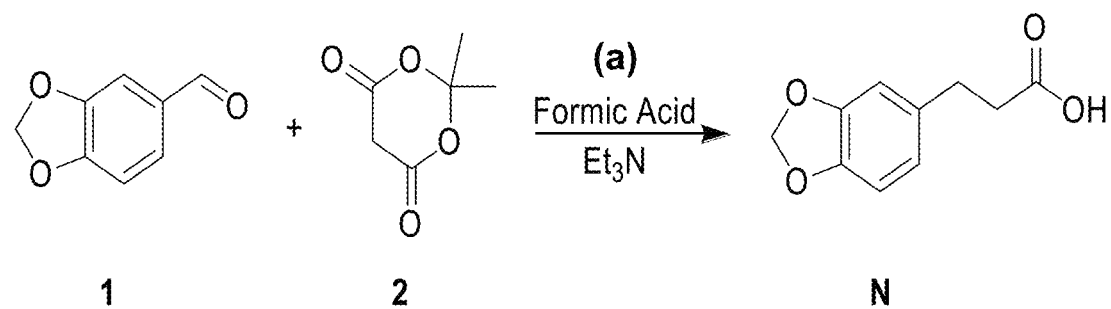
FIGS. 6A and 6B depict further example reactions in another example chemical synthesis pathway for the synthesis of another example compound according to the present disclosure.

Example 3—Preparation of a Third N-Propylamine Fused Heterocyclic Mescaline Derivative Referring to FIG. 6A, added to formic acid (622 μL, 16.5 mmol) was triethylamine (924 μL, 6.59 mmol) in a dropwise manner at 0° C. Following this, piperonal (1) (500 mg, 3.30 mmol) and 2,2-dimethyl-1,3-dioxane-4,6-dione (2) (533 mg, 3.63 mmol) were added and the entire mixture was dissolved in DMF (20 mL). The flask was heated to 105° C. and $CO_2$ slowly evolved from the reaction mixture. After 3 hours, the mixture was cooled back down to room temperature and 40 mL of cold water was added. The pH was adjusted to ~2 with 1 M aq. HCl and the aqueous phase was extracted with EtOAc (4×30 mL). All organic layers were combined and washed with dilute aq. HCl (0.1 M), water, brine and dried ($MgSO_4$). The mixture was filtered, concentrated, and purified by FC on silica gel (12 g, DCM/MeOH, 100:0 to 90:10) to provide the phenyl propionic acid N (542 mg, 85%) as a light-yellow solid. $^1$H NMR (400 MHz, $CDCl_3$) δ 6.73 (d, J=7.8 Hz, 1H), 6.70 (d, J=1.7 Hz, 1H), 6.66 (dd, J=7.9 Hz, 1.8 Hz, 1H), 5.93 (s, 2H), 2.88 (t, 7.6 Hz, 2H), 2.63 (t, 7.7 Hz, 2H) (FIG. 6A, chemical reaction (a) see: further also chemical reaction (a) in FIG. 3B(i))

Figure 6B:
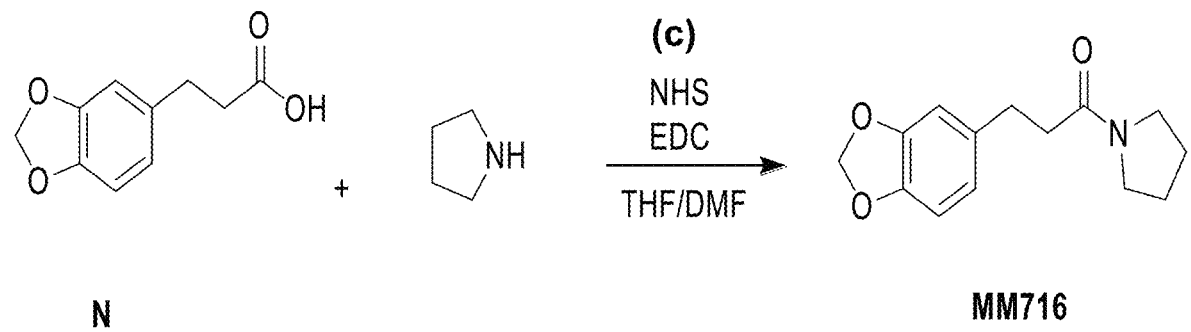

Referring to FIG. 6B, phenyl propionic acid N (200 mg, 1.03 mmol), EDC·HCl (416 mg, 2.06 mmol) and N-hydroxysuccinimide (242 mg, 2.06 mmol) were added to a vial, followed by the addition of anhydrous THF (2.06 mL) and DMF (515 μL). The resulting mixture was stirred for an hour (material slowly dissolved) before the addition of pyrrolidine (173 μL, 2.06 mmol). The reaction was stirred at room temperature overnight. The mixture was poured into a separatory funnel containing 50 mL water and 50 mL EtOAc. The aqueous phase was extracted with ethyl acetate (3×30 mL), all organic layers were combined, washed with 0.1 M HCl, water, brine and dried over $MgSO_4$. After filtration and evaporation of the solvent, the crude residue was purified by FC on silica gel (12 g, DCM/MeOH 100:0 to 90:10) to provide the pure product, MM716 (205 mg, 80%) as a colorless oil. LRMS-HESI: calculated 248.13 m/z for $[M+H]^+$, found 248.16. $^1$H NMR (400 MHz, $CDCl_3$) δ 6.73-6.66 (m, 3H), 5.91 (s, 2H), 3.47-3.44 (m, 2H), 3.32-3.29 (m, 2H), 2.90 (t, J=7.8 Hz, 2H) 2.51 (t, J=7.8 Hz, 2H), 1.89-1.81 (m, 4H) (FIG. 6B, chemical reaction (c), see: further also chemical reaction (c1) in FIG. 3B(i), FIG. 3B(ii)).

It is noted that MM716 corresponds with chemical compound F(III):

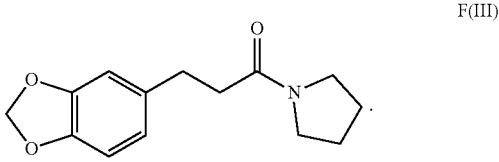 [SMILES: O=C(CCc1ccc2c(c1)OCO2)N1CCCC1]

F(III)

5-HT receptor radioligand competition assays. Activity at $5\text{-HT}_{1A}$ and $5\text{-HT}_{2A}$ receptors were assessed as described for Example 2, except the compound with formula F(III) was evaluated in place of the compound with formula B(II). Table 1 shows radioligand competition assay results for positive controls, negative controls, and compound with formula F(III), in the form of $K_i$ values. In view of results for both positive and negative controls, wherein negative controls yield data insufficient for reliable $K_i$ calculations (i.e., $K_i$>1000 μM) the $K_i$ value obtained for the compound with formula D(I) at the $5\text{-HT}_{1A}$ receptor (>1000 μM, Table 1) indicates little or no ligand-receptor binding. Conversely, the $K_i$ value obtained for the compound with formula F(III) at the $5\text{-HT}_{2A}$ receptor (152 μM, Table 1) indicates ligand-receptor binding.

In Vitro Survey of Pharmacological Interaction Profiles at Receptors and Transporters Linked to Targeted Health Conditions.

The compound with formula F(III) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A ($5\text{-HTR}_{1A}$), HTR2A ($5\text{-HTR}_{2A}$), HTR2B ($5\text{-HT}_{2B}$), HTR2C ($5\text{-HT}_{2C}$), HTR7 ($5\text{-HT}_7$), alpha2A ($α_{2A}$), MT1 ($MT_1$), D3 ($D_3$)) and 3 transporters (SERT, DAT, NET). Assays were conducted using the same materials and procedures outlined in Example 2, except the compound with formula F(III) was used in place of the compound with formula B(II). Overall assay conditions are summarized in Tables 3 and 4 for GPCR and transporters, respectively. Results for all calibrator compounds, control compounds, and test compounds including the compound with formula F(III) are summarized in Table 5.

Figure 7A:
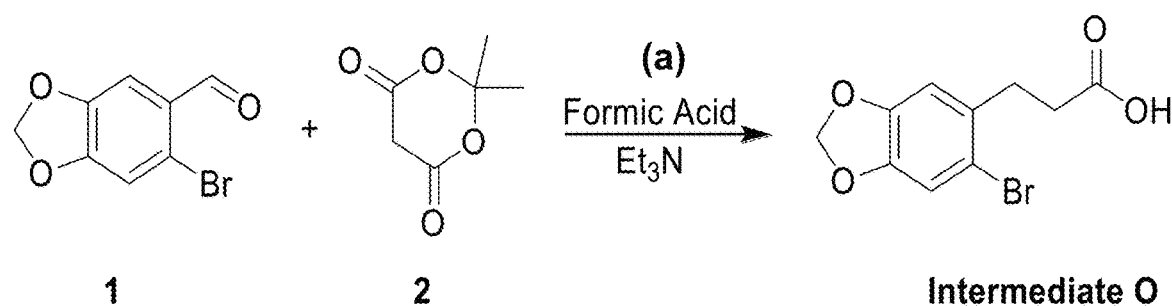
FIGS. 7A and 7B depict further example reactions in another example chemical synthesis pathway for the synthesis of another example compound according to the present disclosure.

Example 4—Preparation of a Fourth N-Propylamine Fused Heterocyclic Mescaline Derivative Referring to FIG. 7A, added to formic acid (618 µL, 16.4 mmol) was triethylamine (917 µL, 6.55 mmol) in a dropwise manner at 0° C. Following this, 6-bromo-1,3-benzodioxole-5-carboxaldehyde (1) (750 mg, 3.27 mmol) and 2,2-dimethyl-1,3-dioxane-4,6-dione (2) (530 mg, 3.60 mmol) were added and the entire mixture was dissolved in DMF (19.8 mL). The flask was heated to 105° C. and $CO_2$ was slowly released from the reaction mixture. After 3 hours, the mixture was cooled back down to room temperature and 40 mL of cold water was added. The pH was adjusted to ~2 with 1 M aq. HCl and the aqueous phase was extracted with EtOAc (4×30 mL). All organic layers were combined and washed with dilute aq. HCl (0.1 M), water, brine and dried ($MgSO_4$). The mixture was filtered, concentrated, and purified by FC on silica gel (12 g, DCM/MeOH, 100:0 to 90:10) to provide the pure compound, O (611 mg, 68%) as a light brown solid. $^1$H NMR (400 MHz, $CDCl_3$) δ 6.99 (s, 1H), 6.76 (s, 1H), 5.95 (s, 2H), 2.98 (t, J=7.7 Hz, 2H), 2.66 (t, J=7.6 Hz, 2H) (FIG. 7A, chemical reaction (a), see: further also chemical reaction (a) in FIG. 3B(i)).

Figure 7B:
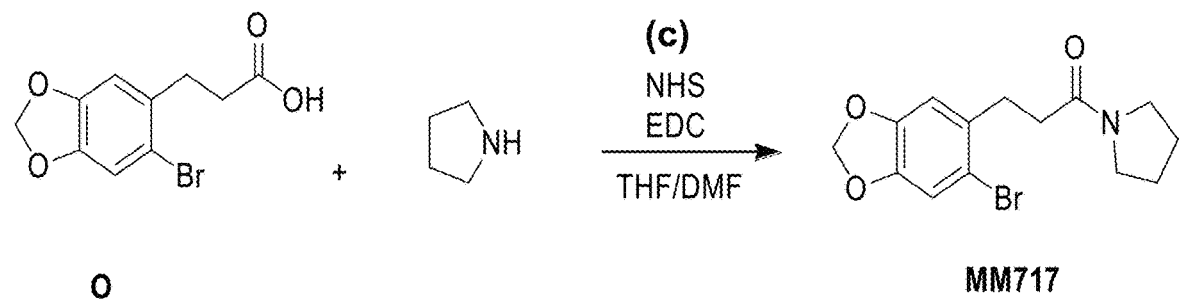

Referring to FIG. 7B, phenyl propionic acid O (200 mg, 732 µmol), EDC·HCl (296 mg, 1.46 mmol) and N-hydroxysuccinimide (172 mg, 1.46 mmol) were added to a vial, followed by the addition of anhydrous THF (1.46 mL) and DMF (366 µL). The resulting mixture was stirred for an hour (material slowly dissolved) before the addition of pyrrolidine (123 µL, 1.46 mmol). The reaction was stirred at room temperature overnight. The mixture was poured into a separatory funnel containing 50 mL water and 50 mL EtOAc. The aqueous phase was extracted with ethyl acetate (3×30 mL), all organic layers were combined, washed with 0.1 M HCl, water, brine and dried over $MgSO_4$. After filtration and evaporation of the solvent, the crude material was subjected to purification by FC on silica gel (12 g, DCM/MeOH 100:0 to 90:10) to provide the pure product, MM717 (180 mg, 75%), as a white solid. LRMS-HESI: calculated 328.04 m/z for [M+H]$^+$, found 327.98. $^1$H NMR (400 MHz, $CDCl_3$) δ 6.97 (s, 1H), 6.81 (s, 1H), 5.93 (s, 2H), 3.46 (br t, J=6.9 Hz, 2H), 3.35 (br t, J=6.7 Hz, 2H), 3.00 (t, J=7.8 Hz, 2H), 2.53 (t, J=7.8 Hz, 2H), 1.93-1.82 (m, 4H) (FIG. 7B, chemical reaction (c), see: further also chemical reaction (c1) in FIG. 3B(i), FIG. 3B(ii)).

It is noted that MM717 corresponds with chemical compound F(IV):

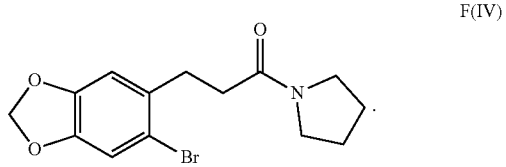 [SMILES: O=C(CCc1cc2c(cc1Br)OCO2)N1CCCC1]

F(IV)

5-HT receptor radioligand competition assays. Activity at the 5-HT$_{1A}$ receptor was assessed as described for Example 2, except the compound with formula F(IV) was evaluated in place of the compound with formula B(II). Table 1 shows radioligand competition assay results for positive controls, negative controls, and compound with formula F(IV), in the form of K$_i$ values. In view of results for both positive and negative controls, wherein negative controls yield data insufficient for reliable K$_i$ calculations (i.e., K$_i$>1000 µM) the K$_i$ value obtained for the compound with formula F(IV) at the 5-HT$_{1A}$ receptor (84.5 µM, Table 1) indicates ligand-receptor binding.

In Vitro Survey of Pharmacological Interaction Profiles at Receptors and Transporters Linked to Targeted Health Conditions.

The compound with formula F(IV) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A (5-HT$_{1A}$), HTR2A (5-HT$_{2A}$), HTR2B (5-HT$_{2B}$), HTR2C (5-HT$_{2C}$), HTR7 (5-HT$_7$), alpha2A ($\alpha_{2A}$), MT1 (MT$_1$), D3 (D$_3$)) and 3 transporters (SERT, DAT, NET). Assays were conducted using the same materials and procedures outlined in Example 2, except the compound with formula F(IV) was used in place of the compound with formula B(II). Overall assay conditions are summarized in Tables 3 and 4 for GPCR and transporters, respectively. Results for all calibrator compounds, control compounds, and test compounds including the compound with formula F(IV) are summarized in Table 5.

Figure 8:
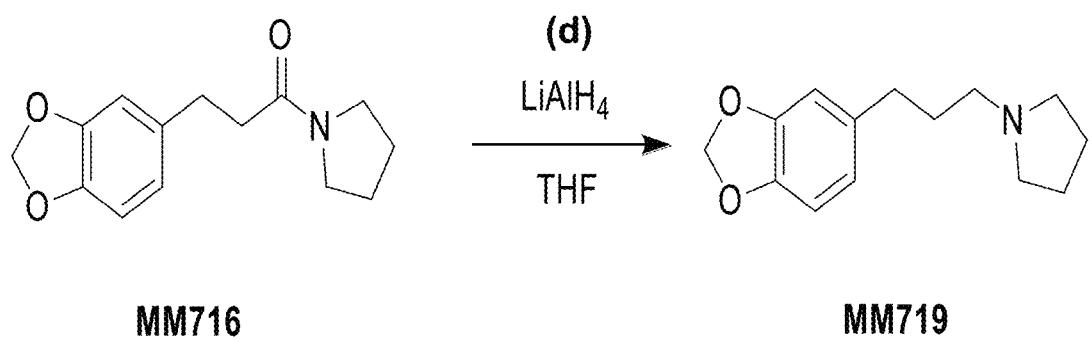
FIG. 8 depicts an example chemical reaction for the synthesis of another example compound according to the present disclosure.

Example 5—Preparation of a Fifth N-Propylamine Fused Heterocyclic Mescaline Derivative Referring to FIG. 8, into a round bottomed flask was added MM716 (150 mg, 607 µmol) (prepared as described in Example 3) followed by dry THF (5.50 mL). The solution was cooled down to 0° C. Lithium aluminum hydride (2M in THF, 910 µL, 1.82 mmol) was carefully added and the mixture was warmed to room temperature and left to react overnight. The mixture was cooled to 0° C. and the excess LiAlH$_4$ was quenched with cold water (5 mL). The resulting solution was poured into a separatory funnel containing 30 mL of water and the aqueous phase was extracted with EtOAc (4×30 mL). All organic layers were combined, washed with brine, dried (MgSO$_4$), filtered and concentrated to leave a colorless oil. The crude product was purified by FC on silica gel (4 g, DCM/MeOH 100:0 to 90:10) to provide the desired product, MM719 (91.0 mg, 64%), as a colorless oil. LRMS-HESI: calculated 234.15 m/z for [M+H]$^+$, found 234.12. $^1$H NMR (400 MHz, $CDCl_3$) δ 6.71 (d, J=7.9 Hz, 1H), 6.68 (d, J=1.7 Hz, 1H), 6.62 (dd, J=7.9 Hz, 1.7 Hz, 1H), 5.91 (s, 2H), 2.59-2.45 (m, 8H) 1.86-1.75 (m, 6H) (FIG. 8, chemical reaction (d), see: further also chemical reaction (d) in FIG. 3B(ii)).

It is noted that MM719 corresponds with chemical compound C(III):

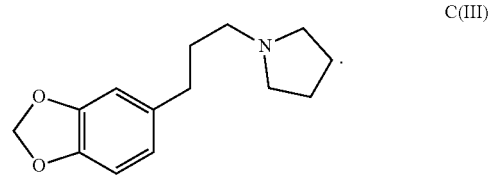 [SMILES: c1cc2c(cc1CCCN1CCCC1)OCO2]

C(III)

5-HT receptor radioligand competition assays. Activity at the 5-HT$_{1A}$ receptor was assessed as described for Example 2, except the compound with formula C(III) was evaluated in place of the compound with formula B(II). Table 1 shows radioligand competition assay results for positive controls, negative controls, and compound with formula C(III), in the form of $K_i$ values. In view of results for both positive and negative controls, wherein negative controls yield data insufficient for reliable $K_i$ calculations (i.e., $K_i$>1000 µM) the $K_i$ value obtained for the compound with formula C(III) at the 5-$HT_{1A}$ receptor (2.33 µM, Table 1) indicates ligand-receptor binding.

In Vitro Survey of Pharmacological Interaction Profiles at Receptors and Transporters Linked to Targeted Health Conditions.

The compound with formula C(III) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A (5-$HTR_{1A}$), HTR2A (5-$HTR_{2A}$), HTR2B (5-$HT_{2B}$), HTR2C (5-$HT_{2C}$), HTR7 (5-$HT_7$), alpha2A ($\alpha_{2A}$), MT1 ($MT_1$), D3 ($D_3$)) and 3 transporters (SERT, DAT, NET). Assays were conducted using the same materials and procedures outlined in Example 2, except the compound with formula C(III) was used in place of the compound with formula B(II). Overall assay conditions are summarized in Tables 3 and 4 for GPCR and transporters, respectively. Results for all calibrator compounds, control compounds, and test compounds including the compound with formula C(III) are summarized in Table 5.

Figure 9:
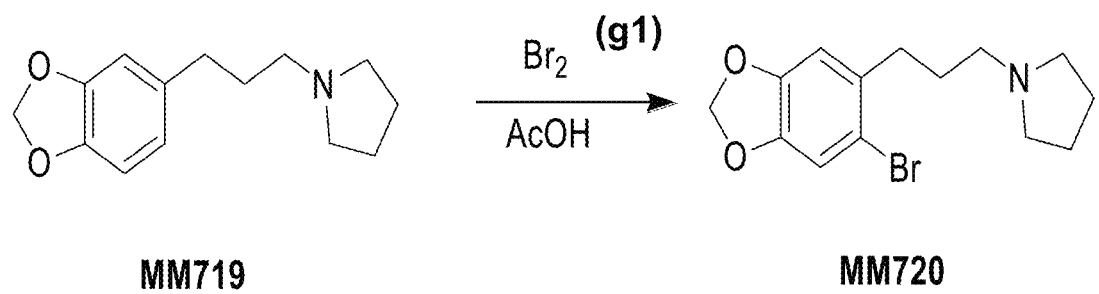
FIG. 9 depicts another example chemical reaction for the synthesis of another example compound according to the present disclosure.

Example 6—Preparation of a Sixth N-Propylamine Fused Heterocyclic Mescaline Derivative Referring to FIG. 9, compound MM719 (70.0 mg, 300 µmol) (prepared as described in Example 5) was dissolved in acetic acid (1.58 mL). Added to this was a solution of bromine (25.0 µL, 486 µmol) in acetic acid (250 µL). The reaction mixture was left to react at room temperature for 3 hours, at which point the starting material was no longer present (TLC, DCM/MeOH 9:1). The mixture was poured into water (15 mL) and the pH was increased to ~10 with 1 M aq. NaOH. The aqueous layer was extracted with DCM (3×25 mL), all organic layers were combined, washed with water, brine, dried with $MgSO_4$, filtered, and concentrated to leave a colourless oil. The crude material was purified by FC on silica gel (4 g, DCM/MeOH 100:0 to 90:10) to provide MM720 (65.1 mg, 69%) as a colorless oil. LRMS-HESI: calculated 312.06 m/z for [M+H]$^+$, found 312.05. $^1$H NMR (400 MHz, $CDCl_3$) δ 6.97 (s, 1H), 6.71 (s, 1H), 5.94 (s, 2H), 2.70-2.66 (m, 2H), 2.57-2.50 (m, 6H), 1.85-1.77 (m, 6H). (FIG. 9, chemical reaction (g1), see: further also chemical reaction (g) in FIG. 3B(ii)).

It is noted that MM720 corresponds with chemical compound C(IV):

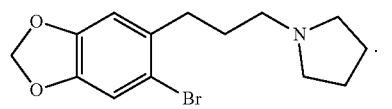

C(IV)

5-HT receptor radioligand competition assays. Activity at the 5-$HT_{1A}$ receptor was assessed as described for Example 2, except the compound with formula C(IV) was evaluated in place of the compound with formula B(II). Table 1 shows radioligand competition assay results for positive controls, negative controls, and compound with formula C(IV), in the form of $K_i$ values. In view of results for both positive and negative controls, wherein negative controls yield data insufficient for reliable $K_i$ calculations (i.e., $K_i$>1000 µM) the $K_i$ value obtained for the compound with formula C(IV) at the 5-$HT_{1A}$ receptor (0.596 µM, Table 1) indicates ligand-receptor binding.

In Vitro Survey of Pharmacological Interaction Profiles at Receptors and Transporters Linked to Targeted Health Conditions.

The compound with formula C(IV) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A (5-$HTR_{1A}$), HTR2A (5-$HTR_{2A}$), HTR2B (5-$HT_{2B}$), HTR2C (5-$HT_{2C}$), HTR7 (5-$HT_7$), alpha2A ($\alpha_{2A}$), MT1 ($MT_1$), D3 ($D_3$)) and 3 transporters (SERT, DAT, NET). Assays were conducted using the same materials and procedures outlined in Example 2, except the compound with formula C(IV) was used in place of the compound with formula B(II). Overall assay conditions are summarized in Tables 3 and 4 for GPCR and transporters, respectively. Results for all calibrator compounds, control compounds, and test compounds including the compound with formula C(IV) are summarized in Table 5.

Figure 10:
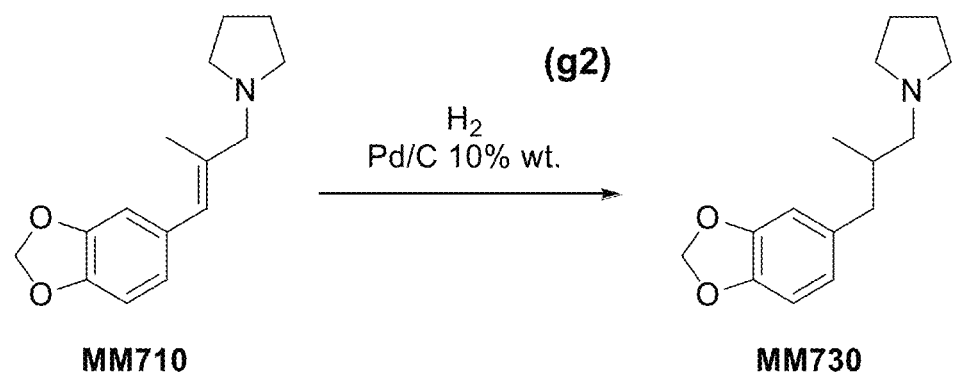
FIG. 10 depicts another example chemical reaction for the synthesis of another example compound according to the present disclosure.

Example 7—Preparation of a Seventh N-Propylamine Fused Heterocyclic Mescaline Derivative Referring to FIG. 10, to a solution of MM710 (47.0 mg, 192 µmol) (prepared as described in Example 2) in ethanol (1.92 mL) under nitrogen atmosphere was added palladium on carbon 10 wt % (20.4 mg, 192 µmol). $H_2$ gas (balloon) was bubbled through the mixture for 15 minutes until a hydrogen atmosphere was established, then left under hydrogen for 36 h. The catalyst was removed via a 0.45 um syringe filter, which was then washed with methanol (3 mL). The filtrate was concentrated under reduced pressure. Purification by FC on silica gel (4 g, 0 to 10% MeOH/DCM) yielded MM730 (racemate) as a white powder (16.8 mg, 34%). LRMS-HESI: calculated 248.16 m/z for [M+H]$^+$, found 248.20. $^1$H NMR (400 MHz, $CDCl_3$) δ 6.75 (d, J=7.9 Hz, 1H), 6.67 (d, J=1.7 Hz, 1H), 6.62 (dd, J=7.8, 1.7 Hz, 1H), 5.95 (s, 2H), 3.47-2.97 (m, 4H), 2.85 (d, J=6.8 Hz, 2H), 2.70 (dd, J=13.8, 7.1 Hz, 1H), 2.54 (dd, J=13.8, 7.3 Hz, 1H), 2.22-2.06 (m, 5H), 1.22 (d, J=6.6 Hz, 3H) (FIG. 10, chemical reaction (g2), see: further also chemical reaction (g) in FIG. 3A(ii)).

It is noted that MM730 corresponds with chemical compound A(II):

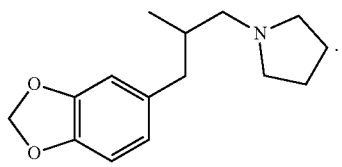

5-HT receptor radioligand competition assays. Activity at the 5-HT$_{1A}$ receptor was assessed as described for Example 2, except the compound with formula A(II) was evaluated in place of the compound with formula B(II). Table 1 shows radioligand competition assay results for positive controls, negative controls, and compound with formula A(II) in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(II) at the 5-HT$_{1A}$ receptor (8.0 μM, Table 1) indicates ligand-receptor binding.

In Vitro Survey of Pharmacological Interaction Profiles at Receptors and Transporters Linked to Targeted Health Conditions.

The compound with formula A(II) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A (5-HTR$_{1A}$), HTR2A (5-HTR$_{2A}$), HTR2B (5-HT$_{2B}$), HTR2C (5-HT$_{2C}$), HTR7 (5-HT$_7$), alpha2A ($\alpha_{2A}$), MT1 (MT$_1$), D3 (D$_3$)) and 3 transporters (SERT, DAT, NET). Assays were conducted using the same materials and procedures outlined in Example 2, except the compound with formula A(II) was used in place of the compound with formula B(II). Overall assay conditions are summarized in Tables 3 and 4 for GPCR and transporters, respectively. Results for all calibrator compounds, control compounds, and test compounds including the compound with formula A(II) are summarized in Table 5.

Figure 11:
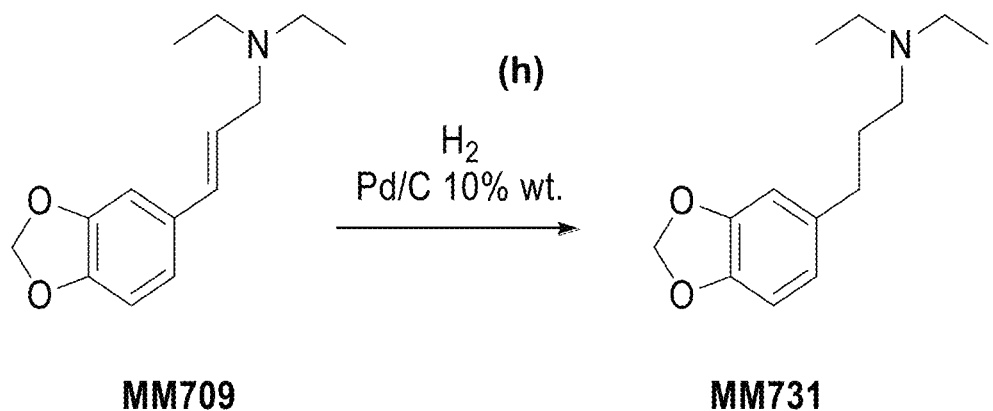
FIG. 11 depicts another example chemical reaction for the synthesis of another example compound according to the present disclosure.

Example 8—Preparation of an Eighth N-Propylamine Fused Heterocyclic Mescaline Derivative Referring to FIG. 11, to a solution of MM709 (45.0 mg, 193 μmol) (prepared as described in Example 1) in ethanol (1.93 mL) under nitrogen atmosphere was added palladium on carbon 10% wt. (20.5 mg, 0.0193 μmol). H$_2$ gas (balloon) was bubbled through the mixture for 15 minutes until a hydrogen atmosphere was established, then left under hydrogen for 36 h with vigorous stirring. The catalyst was removed via a 0.45 um syringe filter, which was then washed with methanol (3 mL). The filtrate was concentrated under reduced pressure. Purification by FC on silica gel (4 g, 0 to 10% MeOH/DCM) yielded MM731 as a white powder (12.6 mg, 28%). LRMS-HESI: calculated 236.16 m/z for [M+H]$^+$, found 236.17. $^1$H NMR (400 MHz, CDCl$_3$) δ 6.74 (d, J=7.9 Hz, 1H), 6.69-6.61 (m, 2H), 5.94 (s, 2H), 3.09 (q, J=7.4 Hz, 4H), 2.98-2.90 (m, 2H), 2.65 (t, J=7.2 Hz, 2H), 2.17-2.06 (m, 2H), 1.36 (t, J=7.3 Hz, 6H) (FIG. 11, chemical reaction (h), see: further also chemical reaction (h) in FIG. 3A(ii)).

It is noted that MM731 corresponds with chemical compound C(I):

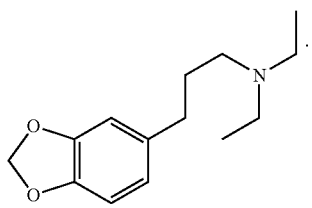

5-HT receptor radioligand competition assays. Activity at the 5-HT$_{1A}$ receptor was assessed as described for Example 2, except the compound with formula C(I) was evaluated in place of the compound with formula B(II). Table 1 shows radioligand competition assay results for positive controls, negative controls, and compound with formula C(I), in the form of K$_i$ values. In view of results for both positive and negative controls, wherein negative controls yield data insufficient for reliable K$_i$ calculations (i.e., K$_i$>1000 μM) the K$_i$ value obtained for the compound with formula C(I) at the 5-HT$_{1A}$ receptor (2.9 μM, Table 1) indicates ligand-receptor binding.

In Vitro Survey of Pharmacological Interaction Profiles at Receptors and Transporters Linked to Targeted Health Conditions.

The compound with formula C(I) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A (5-HTR$_{1A}$), HTR2A (5-HTR$_{2A}$), HTR2B (5-HT$_{2B}$), HTR2C (5-HT$_{2C}$), HTR7 (5-HT$_7$), alpha2A ($\alpha_{2A}$), MT1 (MT$_1$), D3 (D$_3$)) and 3 transporters (SERT, DAT, NET). Assays were conducted using the same materials and procedures outlined in Example 2, except the compound with formula C(I) was used in place of the compound with formula B(II). Overall assay conditions are summarized in Tables 3 and 4 for GPCR and transporters, respectively. Results for all calibrator compounds, control compounds, and test compounds including the compound with formula C(I) are summarized in Table 5.

Figure 12A:
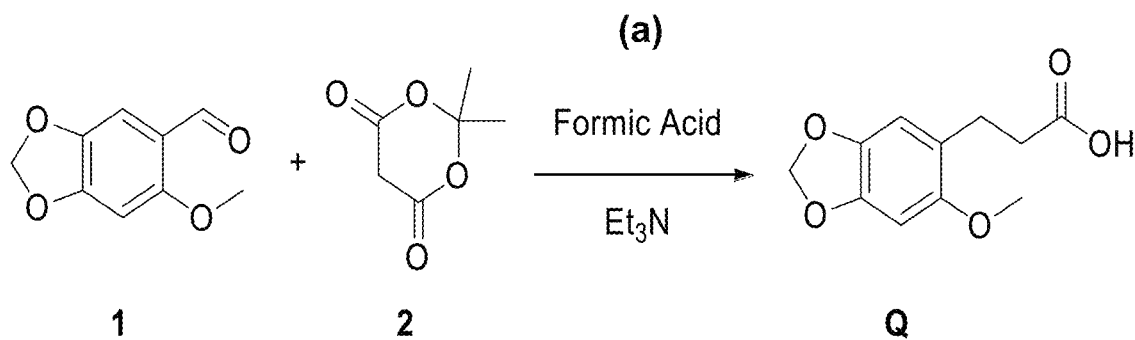
FIGS. 12A and 12B depict further example reactions in another example chemical synthesis pathway for the synthesis of another example compound according to the present disclosure.

Example 9—Preparation of a Ninth N-Propylamine Fused Heterocyclic Mescaline Derivative Referring to FIG. 12A, added to formic acid (628 μL, 16.7 mmol) was triethylamine (933 μL, 6.66 mmol) in a dropwise manner at 0° C. Following this, 6-Methoxy-1,3-benzodioxole-5-carbaldehyde (1) (600 mg, 3.33 mmol) and 2,2-dimethyl-1,3-dioxane-4,6-dione (2) (539 mg, 3.66 mmol) were added and the entire mixture was dissolved in DMF (20.2 mL). The flask was heated to 105° C. and CO$_2$ slowly evolved from the reaction mixture. After 3 hours, the mixture was cooled back down to room temperature and 40 mL of cold water was added. The pH was adjusted to ~2 with 1 M aq. HCl and the aqueous phase was extracted with EtOAc (4×30 mL). All organic layers were combined and washed with dilute aq. HCl (0.1 M), water, brine and dried (MgSO$_4$). The mixture was filtered, concentrated, and purified by FC on silica gel (12 g, DCM/MeOH, 100:0 to 90:10) to provide intermediate Q (490 mg, 66%). $^1$H NMR (400 MHz, CDCl$_3$) δ 6.67 (s, 1H), 6.50 (s, 1H), 5.89 (s, 2H), 3.76 (s, 3H), 2.85 (t, J=7.6 Hz, 2H), 2.60 (t, J=7.7 Hz, 2H) (FIG. 12A, chemical reaction (a), see: further also chemical reactions (a) in FIG. 3B(i)).

Figure 12B:
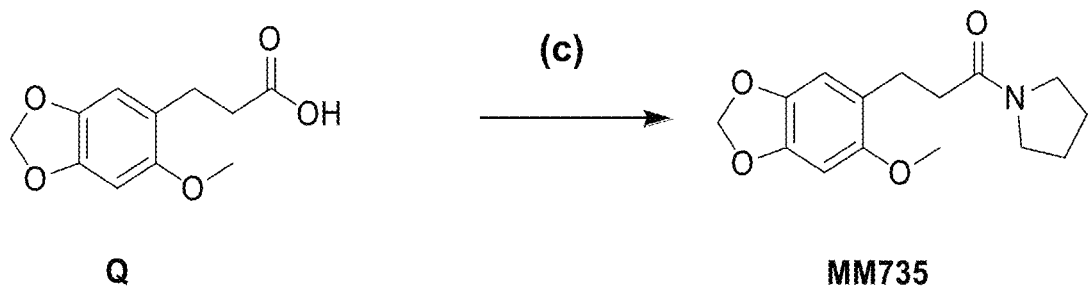

Referring to FIG. 12B, phenyl proprionic acid Q (160 mg, 714 μmol), EDC·HCl (288 mg, 1.43 mmol) and N-hydroxysuccinimide (168 mg, 1.43 mmol) were added to a vial, followed by the addition of anhydrous THF (1.43 mL) and DMF (357 μL). The resulting mixture was stirred for an hour (material slowly dissolved) before the addition of pyrrolidine (120 μL, 1.43 mmol). The reaction was stirred at room temperature overnight. The mixture was poured into a separatory funnel containing 50 mL water and 50 mL EtOAc. The aqueous phase was extracted with ethyl acetate (3×30 mL), all organic layers were combined, washed with 0.1 M HCl, water, brine and dried over MgSO$_4$. After filtration and evaporation of the solvent, the remaining crude material was purified by FC on silica gel (4 g, DCM/MeOH 100:0 to 90:10) to provide the pure product, MM735 (153 mg, 77%), as light orange solid. LRMS-HESI: calculated 278.14 m/z for [M+H]$^+$, found 278.13. $^1$H NMR (400 MHz, CDCl$_3$) δ 6.70 (s, 1H), 6.50 (s, 1H), 5.88 (s, 2H), 3.76 (s, 3H), 3.48-3.34 (br m, 4H), 2.90-2.86 (m, 2H), 2.52-2.48 (m, 2H), 1.86 (br m, 4H) (FIG. 12B, chemical reaction (c), see: further also chemical reaction (c1) in FIG. 3B(i), FIG. 3B(ii))

It is noted that MM735 corresponds with chemical compound F(V):

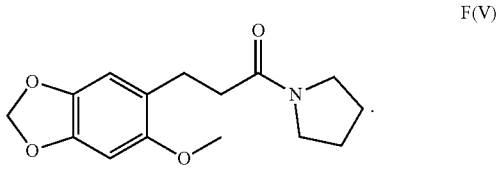 [SMILES: COc1cc2c(cc1CCC(=O)N1CCCC1)OCO2]

F(V)

5-HT receptor radioligand competition assays. Activity at the 5-HT$_{1A}$ receptor was assessed as described for Example 2, except the compound with formula F(V) was evaluated in place of the compound with formula B(II). Table 1 shows radioligand competition assay results for positive controls, negative controls, and compound with formula F(V), in the form of K$_i$ values. In view of results for both positive and negative controls, wherein negative controls yield data insufficient for reliable K$_i$ calculations (i.e., K$_i$>1000 μM) the K$_i$ value obtained for the compound with formula F(V) at the 5-HT$_{1A}$ receptor (363.5 μM, Table 1) indicates ligand-receptor binding.

5-HT$_{1A}$ receptor functional cellular response assay. Functional engagement of the 5-HT$_{1A}$ receptor within an engineered cell system was assessed as described for Example 2, except the compound with formula F(V) was evaluated in place of the compound with formula B(II). Table 2 shows functional assay results for positive controls, calibrators, and compound with formula F(V), in the form of EC$_{50}$ values. In view of results for controls and calibrator compounds, wherein a negative cellular response corresponded to an EC$_{50}$ value >1000 μM, the EC$_{50}$ value for the compound with formula F(V) in this assay (10.0 μM, Table 2) suggested ligand-receptor engagement.

In Vitro Survey of Pharmacological Interaction Profiles at Receptors and Transporters Linked to Targeted Health Conditions.

The compound with formula F(V) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A (5-HTR$_{1A}$), HTR2A (5-HTR$_{2A}$), HTR2B (5-HT$_{2B}$), HTR2C (5-HT$_{2C}$), HTR7 (5-HT$_7$), alpha2A (α$_{2A}$), MT1 (MT$_1$), D3 (D$_3$)) and 3 transporters (SERT, DAT, NET). Assays were conducted using the same materials and procedures outlined in Example 2, except the compound with formula F(V) was used in place of the compound with formula B(II). Overall assay conditions are summarized in Tables 3 and 4 for GPCR and transporters, respectively. Results for all calibrator compounds, control compounds, and test compounds including the compound with formula F(V) are summarized in Table 5.

Figure 13:
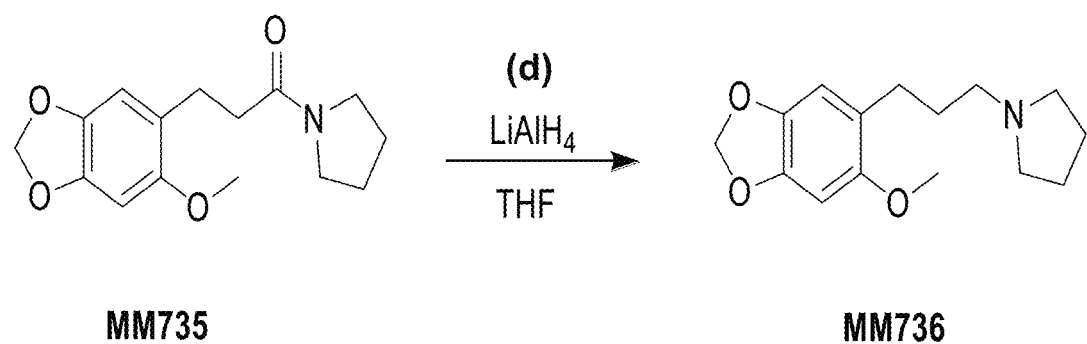
FIG. 13 depicts another example chemical reaction for the synthesis of another example compound according to the present disclosure.

Example 10—Preparation of a Tenth N-Propylamine Fused Heterocyclic Mescaline Derivative Referring to FIG. 13, into a round bottom flask was added MM735 (120 mg, 433 μmol) (prepared as described in Example 9) followed by dry THF (3.92 mL). The reaction mixture was cooled down to 0° C. Lithium aluminum hydride (2M in THF, 649 μL, 1.30 mmol) was carefully added and the mixture was warmed to room temperature and left to react overnight. The mixture was cooled to 0° C. and the excess LiAlH$_4$ was quenched with cold water (4 mL). The resulting solution was poured into a separatory funnel containing 30 mL of water, and the aqueous phase was extracted with EtOAc (4×30 mL). All organic layers were combined, washed with brine, dried (MgSO$_4$), filtered and concentrated to leave a colorless oil. The crude residue was purified by FC on silica gel (4 g, DCM/MeOH 100:0 to 90:10) to provide the desired product, MM736 (70.0 mg, 61%), as a colorless oil. LRMS-HESI: calculated 264.16 m/z for [M+H]$^+$, found 264.15. $^1$H NMR (400 MHz, CDCl$_3$) δ 6.64 (s, 1H), 6.50 (s, 1H), 5.88 (s, 2H), 3.75 (s, 3H), 2.58-2.54 (m, 8H), 1.81 (br s, 6H) (FIG. 13, chemical reaction (d), see: further also chemical reaction (d) in FIG. 3B(ii))

It is noted that MM736 corresponds with chemical compound C(V):

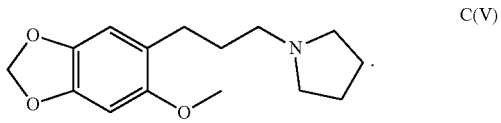 [SMILES: COc1cc2c(cc1CCCN1CCCC1)OCO2]

C(V)

5-HT receptor radioligand competition assays. Activity at the 5-HT$_{1A}$ receptor was assessed as described for Example 2, except the compound with formula C(V) was evaluated in place of the compound with formula B(II). Table 1 shows radioligand competition assay results for positive controls, negative controls, and compound with formula C(V), in the form of $K_i$ values. In view of results for both positive and negative controls, wherein negative controls yield data insufficient for reliable $K_i$ calculations (i.e., $K_i$>1000 μM) the $K_i$ value obtained for the compound with formula C(V) at the 5-$HT_{1A}$ receptor (5.0 μM, Table 1) indicates ligand-receptor binding.

5-$HT_{1A}$ receptor functional cellular response assay. Functional engagement of the 5-$HT_{1A}$ receptor within an engineered cell system was assessed as described for Example 2, except the compound with formula C(V) was evaluated in place of the compound with formula B(II). Table 2 shows functional assay results for positive controls, calibrators, and compound with formula C(V), in the form of $EC_{50}$ values. In view of results for controls and calibrator compounds, wherein a negative cellular response corresponded to an $EC_{50}$ value >1000 μM, the $EC_{50}$ value for the compound with formula C(V) in this assay (116.3 μM, Table 2) suggested ligand-receptor engagement.

In Vitro Survey of Pharmacological Interaction Profiles at Receptors and Transporters Linked to Targeted Health Conditions.

The compound with formula C(V) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 8 G-protein coupled receptors (GPCR) receptors: HTR1A (5-$HTR_{1A}$), HTR2A (5-$HTR_{2A}$), HTR2B (5-$HT_{2B}$), HTR2C (5-$HT_{2C}$), HTR7 (5-$HT_7$), alpha2A ($α_{2A}$), MT1 ($MT_1$), D3 ($D_3$)) and 3 transporters (SERT, DAT, NET). Assays were conducted using the same materials and procedures outlined in Example 2, except the compound with formula C(V) was used in place of the compound with formula B(II). Overall assay conditions are summarized in Tables 3 and 4 for GPCR and transporters, respectively. Results for all calibrator compounds, control compounds, and test compounds including the compound with formula C(V) are summarized in Table 5.

Figure 17:
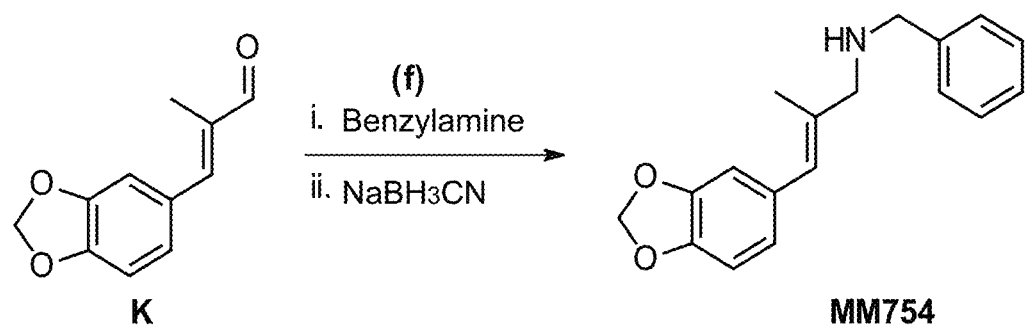
FIG. 17 depicts another example chemical reaction for the synthesis of another example compound according to the present disclosure.

Example 11—Preparation of an Eleventh N-Propylamine Fused Heterocyclic Mescaline Derivative Referring to FIG. 17, to a solution of K (216 mg, 1.14 mmol) (prepared as described in Example 2) in MeOH (7.57 mL) under nitrogen atmosphere was added benzylamine (248 μL, 2.27 mmol). The reaction mixture was heated to 61° C. for 3 hours. After cooling to room temperature, sodium cyanoborohydride (300 mg, 4.54 mmol) was added and the reaction allowed to stir under nitrogen atmosphere at the same temperature for 18 hours. The reaction mixture was diluted with DCM (80 mL), washed with water (50 mL) and brine (2×50 mL). The organic phase was dried over anhydrous magnesium sulphate and concentrated under reduced pressure to yield a crude, slightly yellow oil. Purification by column chromatography on 12 g normal-phase silica using a 0-8, then 70% ethyl acetate-hexanes gradient yielded the product, MM754 (130 mg, 41%), as a colourless oil. LRMS-HESI: calculated 282.15 m/z for [M+H]⁺, found 282.23 m/z. ¹H NMR (400 MHz, CDCl₃) δ 7.39-7.29 (m, 5H), 6.84-6.78 (m, 2H), 6.78-6.71 (m, 1H), 6.39 (q, J=1.6 Hz, 1H), 5.97 (s, 2H), 3.83 (s, 2H), 3.35 (d, J=1.4 Hz, 2H), 1.93 (d, J=1.4 Hz, 3H). (FIG. 17, chemical reaction (f), see: further also chemical reaction (f) in FIG. 3A(i)).

It is noted that MM754 corresponds with chemical compound B(IV):

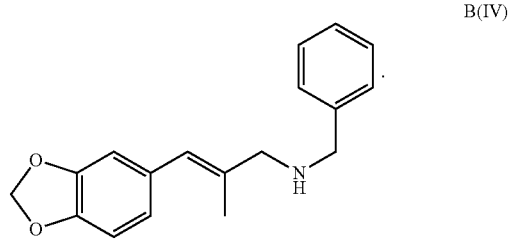 [SMILES: C/C(=C\c1ccc2c(c1)OCO2)CNCc1ccccc1]

B(IV)

Figure 18:
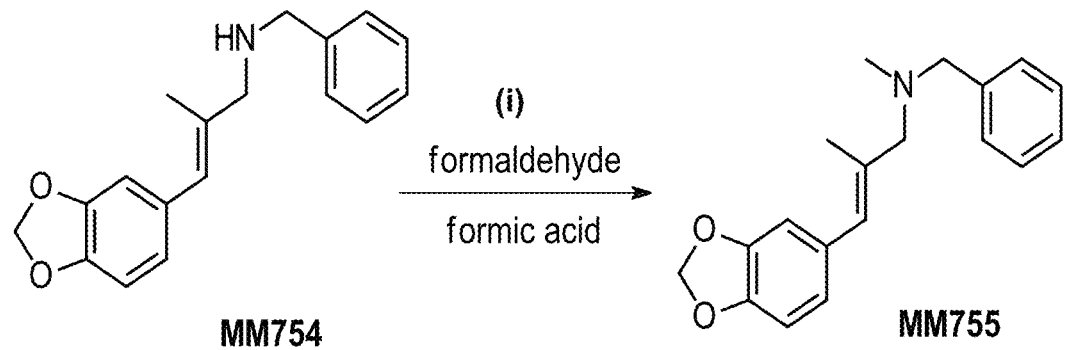
FIG. 18 depicts another example chemical reaction for the synthesis of another example compound according to the present disclosure.

Example 12—Preparation of a Twelfth N-Propylamine Fused Heterocyclic Mescaline Derivative Referring to FIG. 18, in a capped pressure rated vial, MM754 (106 mg, 377 μmol) (prepared as described in Example 11) was dissolved in formic acid (213 μL, 5.65 mmol), and formaldehyde (37% in water, 252 μL, 3.39 mmol) was added. The reaction mixture was heated at 90° C. with a vent needle for 18 h. MS indicated reaction completion. The reaction mixture was diluted with water (20 mL), basified with 15% NaOH until pH ~12, and extracted with DCM (3×20 mL). The combined organic extracts were washed with brine (20 mL), dried over anhydrous magnesium sulphate, and concentrated under reduced pressure to yield the crude product. Purification by column chromatography on 4 g normal-phase silica using a 0 to 10% methanol-dichloromethane eluent gradient yielded MM755 as a colourless oil (48.3 mg, 43%). LRMS-HESI: calculated 296.16 m/z for [M+H]⁺, found 296.22 m/z. ¹H NMR (400 MHz, CDCl₃) δ 7.42-7.33 (m, 4H), 7.31-7.26 (m, 1H), 6.87-6.75 (m, 3H), 6.43-6.39 (m, 1H), 5.98 (s, 2H), 3.54 (s, 2H), 3.05 (d, J=1.2 Hz, 2H), 2.22 (s, 3H), 1.97 (d, J=1.4 Hz, 3H). (FIG. 18, chemical reaction (i), see: further also chemical reaction (i) in FIG. 3A(i)).

It is noted that MM755 corresponds with chemical compound B(III):

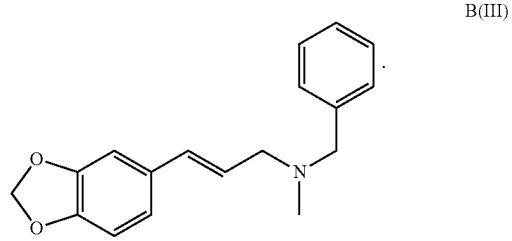 [SMILES: CN(C/C=C/c1ccc2c(c1)OCO2)Cc1ccccc1]

B(III)

Figure 19A:
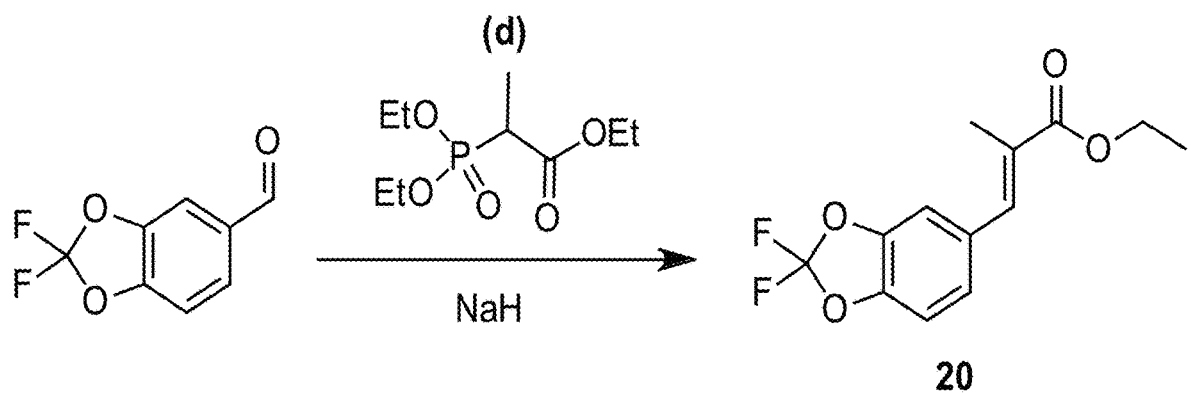
FIGS. 19A, 19B, and 19C depict further example reactions in another example chemical synthesis pathway for the synthesis of another example compound according to the present disclosure.

Example 13—Preparation of a Thirteenth N-Propylamine Fused Heterocyclic Mescaline Derivative Referring to FIG. 19A, to a suspension of sodium hydride (261 mg, 6.51 mmol) in dry THF (3.95 mL) at 0° C. under inert atmosphere was added a solution of triethyl-2-phosphonopropionate (1.44 mL, 6.51 mmol) in dry THF (7.90 mL). Following stirring for 30 minutes, a solution of 2,2-difluoro-5-formylbenzodioxole (703 μL, 5.21 mmol) in dry THF (3.95 mL) was added dropwise over 10 minutes. The reaction mixture was allowed to slowly warm to room temperature and stirring continued for 18 h. Water (5 mL) was added to the stirring mixture, and the organic solvent removed under reduced pressure. The watery residue was extracted with ethyl acetate (3×25 mL) and the combined organic extracts were dried with magnesium sulphate and solvent removed under reduced pressure. Purification by dry-loaded column chromatography on 25 g normal-phase silica using a 0 to 7% ethyl acetate-hexanes eluent gradient provided intermediate 20 as a colourless oil (1.19 g, 85%). LRMS-HESI: calculated 271.08 m/z for [M+H]$^+$, found 271.10 m/z. $^1$H NMR (400 MHz, CDCl$_3$) δ 7.63 (tq, J=1.5, 0.8 Hz, 1H), 7.18-7.07 (m, 3H), 4.30 (q, J=7.1 Hz, 2H), 2.12 (d, J=1.6 Hz, 3H), 1.37 (t, J=7.1 Hz, 3H). (FIG. 19A, chemical reaction (d), see: further also chemical reaction (d) in FIG. 3A(i)).

Figure 19B:
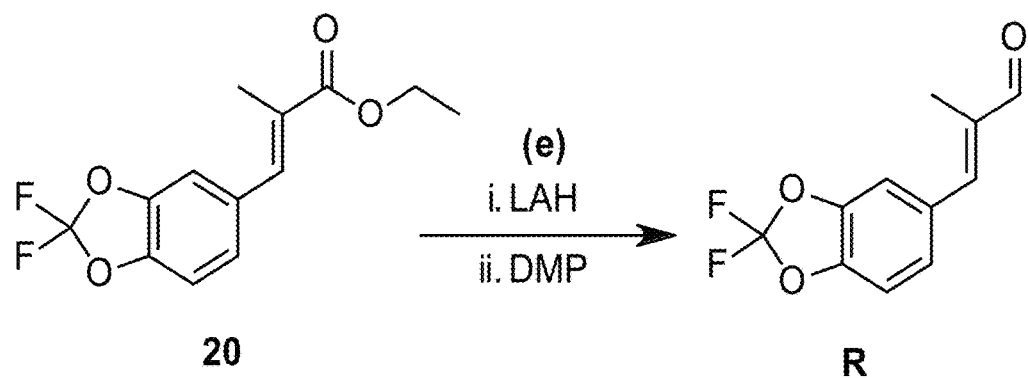

Referring to FIG. 19B, in a flame dried flask at −78° C. under nitrogen atmosphere, lithium aluminum hydride (352 mg, 8.81 mmol) was suspended in anhydrous THF (22.0 mL). To this suspension was added a solution of intermediate 20 (1.19 g, 4.40 mmol) in anhydrous THF (22.0 mL), and the reaction mixture allowed to stir at the same temperature for 5 h. By LCMS, the reaction was incomplete, so more dry ice was added and the insulated bowl further insulated with tin foil for overnight. The reaction mixture was warmed to 0° C. and quenched through successive addition of water (0.4 mL), 15% NaOH (0.4 mL), and water (1.2 mL). The reaction mixture was warmed to room temperature and allowed to stir for 15 minutes. Anhydrous magnesium sulphate was added, and the suspension mixed for a further 15 minutes. The suspension was filtered, and the filter cake washed with THF (50 mL) and diethyl ether (50 mL). The filtrate was concentrated under reduced pressure, yielding a crude colourless oil. Purification by column chromatography on 24 g normal-phase silica using a 0 to 15% ethyl acetate-hexanes gradient a colourless oil (890 mg) after fraction collection. This material was quickly used in the next step. To a solution of this colourless oil (575 mg) in DCM (16.6 mL) was added manganese (IV) oxide (1.17 g, 13.3 mmol) and the reaction mixture was stirred for 18 h. After MS confirmation of product formation, the reaction mixture was filtered through Celite, and the filtrate concentrated under reduced pressure. Purification by column chromatography using a 0-7-15% ethyl acetate-hexanes eluent gradient yielded intermediate R as a white solid (376 mg, 54% over 2 steps). LRMS-HESI: calculated 227.05 m/z for [M+H]$^+$, found 227.03 m/z. $^1$H NMR (400 MHz, CDCl$_3$) δ 9.60 (s, 1H), 7.34-7.26 (m, 2H), 7.23 (q, J=1.5 Hz, 1H), 7.17 (dd, J=8.2, 0.5 Hz, 1H), 2.09 (d, J=1.4 Hz, 3H). (FIG. 19B, chemical reaction (e), see: further also chemical reaction (e) in FIG. 3A(i))

Figure 19C:
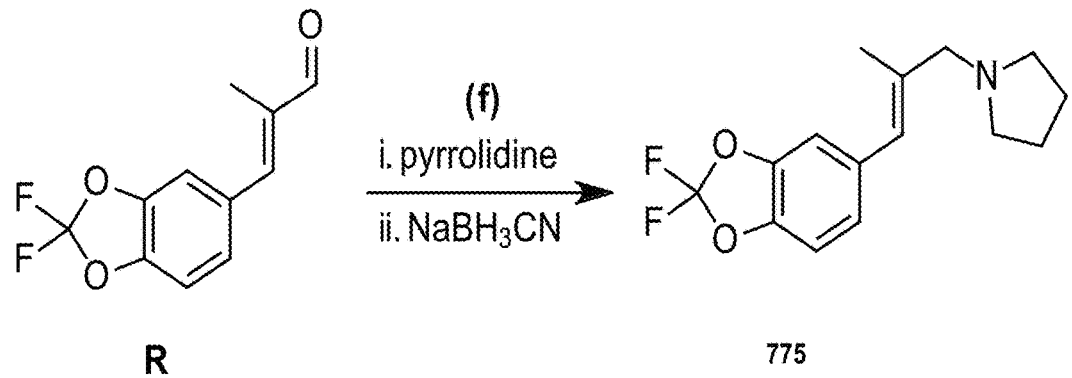

Referring to FIG. 19C to a solution of intermediate R (308 mg, 1.36 mmol) in MeOH (13.6 mL), under nitrogen atmosphere was added pyrrolidine (228 μL, 2.72 mmol). The reaction mixture was heated to 60° C. for 4 h, then cooled to room temperature before addition of sodium cyanoborohydride (360 mg, 5.45 mmol). The reaction mixture was allowed to stir at the same temperature for 18 h, then concentrated under reduced pressure. After diluting with DCM (100 mL), the solution was washed with water (2×25 mL) and brine (25 mL), dried over anhydrous magnesium sulphate, and concentrated under reduced pressure. Purification by column chromatography on 12 g normal-phase silica using a slow 0-4% methanol-dichloromethane eluent gradient yielded MM775 as a yellow oil (42 mg, 11%). LRMS-HESI: calculated 282.13 m/z for [M+H]$^+$, found 282.12 m/z. $^1$H NMR (400 MHz, CDCl$_3$) δ 7.03-6.93 (m, 3H), 6.44-6.39 (m, 1H), 3.15 (d, J=1.3 Hz, 2H), 2.55 (ddt, J=7.5, 6.1, 2.4 Hz, 4H), 1.92 (d, J=1.4 Hz, 3H), 1.86-1.80 (m, 4H). (FIG. 19C, chemical reaction (f), see: further also chemical reaction (f) in FIG. 3A(i)).

It is noted that MM775 corresponds with chemical compound B(V):

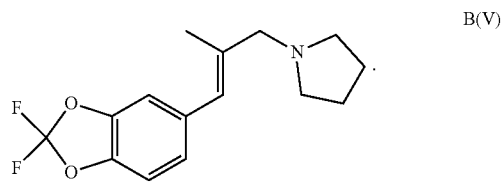 [SMILES: C/C(=C\c1ccc2c(c1)OC(F)(F)O2)CN1CCCC1]

Figure 20:
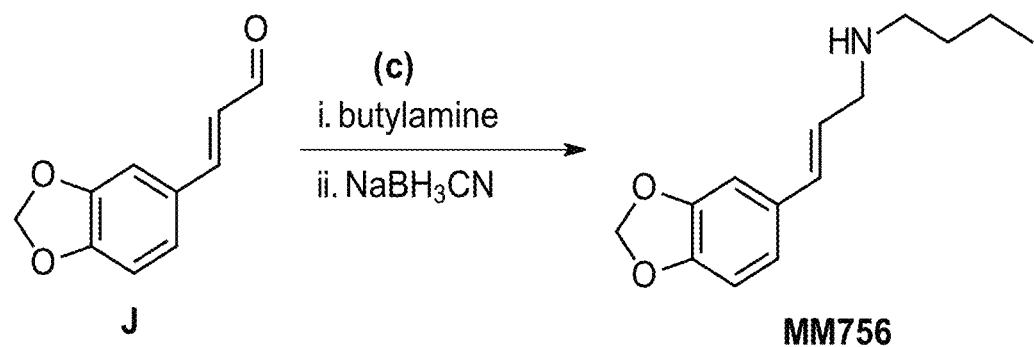
FIG. 20 depicts another example chemical reaction for the synthesis of another example compound according to the present disclosure.

Example 14—Preparation of a Fourteenth N-Propylamine Fused Heterocyclic Mescaline Derivative Referring to FIG. 20, under nitrogen atmosphere, J (242 mg, 1.37 mmol) (prepared as described in Example 1) was dissolved in MeOH (13.7 mL). Acetic acid (197 μL, 3.43 mmol) was added, and the solution allowed to stir for 5 minutes prior to addition of butylamine (363 mg, 2.75 mmol). The reaction was heated to 60° C. for 4 h, then cooled to room temperature and sodium cyanoborohydride (336 mg, 5.49 mmol) was added. The reaction mixture was allowed to stir under nitrogen atmosphere for 4 d. The reaction mixture was diluted with DCM (60 mL) and added to a separatory funnel with water (50 mL). The aqueous phase was adjusted to pH 7-8 with saturated NaHCO$_3$ and extracted with DCM (3×10 mL). The combined organic phases were washed with water (20 mL) and brine (20 mL), then dried over anhydrous magnesium sulphate and concentrated under reduced pressure to yield a crude, yellow gummy solid. Purification by column chromatography on 4 g normal-phase silica using a 0 to 10% methanol-dichloromethane eluent gradient yielded impure product. A second purification by column chromatography on 4 g normal-phase silica using a 5% methanol-dichloromethane eluent system yielded MM756 as an off-white solid (98.7 mg, 31%). LRMS-HESI: calculated 234.14 m/z for [M+H]$^+$, found 234.07 m/z. $^1$H NMR (400 MHz, CDCl$_3$) δ 6.92 (d, J=1.7 Hz, 1H), 6.80 (ddd, J=8.0, 1.7, 0.5 Hz, 1H), 6.73 (d, J=7.9 Hz, 1H), 6.52-6.44 (m, 1H), 6.15 (dt, J=15.8, 6.7 Hz, 1H), 5.92 (s, 2H), 3.46 (dd, J=6.7, 1.4 Hz, 2H), 2.75-2.68 (m, 2H), 1.66-1.54 (m, 2H), 1.36 (dq, J=14.6, 7.4 Hz, 2H), 0.91 (t, J=7.4 Hz, 3H). (FIG. 20, chemical reaction (c), see: further also chemical reaction (c) in FIG. 3A(ii)).

It is noted that MM756 corresponds with chemical compound D(II):

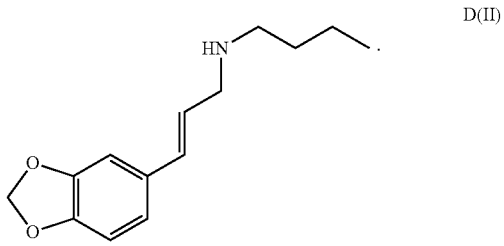 [SMILES: CCCCNC/C=C/c1ccc2c(c1)OCO2]

Figure 21:
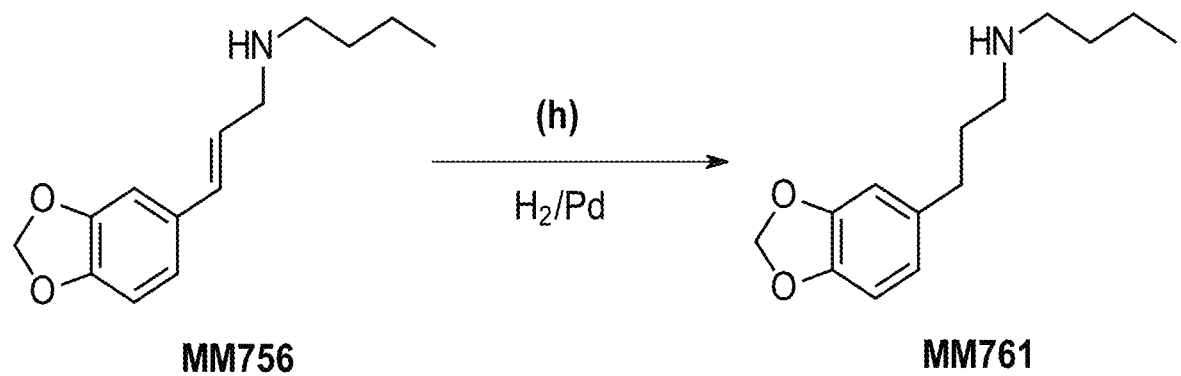
FIG. 21 depicts another example chemical reaction for the synthesis of another example compound according to the present disclosure.

Example 15—Preparation of a Fifteenth N-Propylamine Fused Heterocyclic Mescaline Derivative Referring to FIG. 21, to a solution of MM756 (57.2 mg, 245 μmol) (prepared as described in Example 14) in denatured ethanol (4.90 mL) under nitrogen atmosphere was added palladium on carbon 10 wt % (26.1 mg, 0.0245 μmol). Hydrogen gas was bubbled through the solution for 10 minutes, then established as atmosphere. The reaction mixture was allowed to stir for 50 minutes, at which point LCMS indicated reaction completion. The reaction mixture was filtered through Celite and the filtrate concentrated under reduced pressure to yield MM761 as a light yellow solid (52.4 mg, 91%). LRMS-HESI: calculated 236.16 m/z for [M+H]$^+$, found 236.17 m/z. $^1$H NMR (400 MHz, CDCl$_3$) δ 6.72 (d, J=7.9 Hz, 1H), 6.68 (d, J=1.7 Hz, 1H), 6.65-6.61 (m, 1H), 5.91 (s, 2H), 2.78-2.68 (m, 4H), 2.59 (t, J=7.6 Hz, 2H), 1.95 (p, J=7.6 Hz, 2H), 1.68-1.58 (m, 2H), 1.35 (h, J=7.4 Hz, 2H), 0.91 (t, J=7.4 Hz, 3H). (FIG. 21, chemical reaction (h), see: further also chemical reaction (h) in FIG. 3A(ii)).

It is noted that MM761 corresponds with chemical compound C(II):

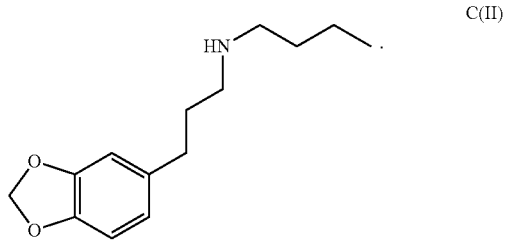 [SMILES: CCCCNCCCc1ccc2c(c1)OCO2]

C(II)

Figure 22A:
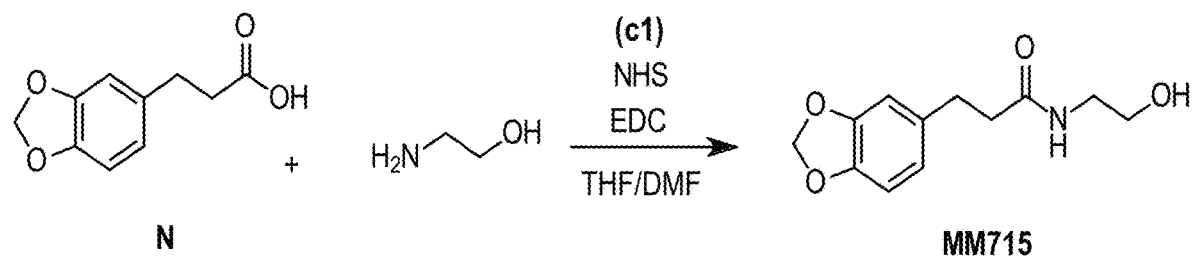
FIGS. 22A and 22B depict further example reactions in another example chemical synthesis pathway for the synthesis of another example compound according to the present disclosure.

Example 16—Preparation of a Sixteenth N-Propylamine Fused Heterocyclic Mescaline Derivative Referring to FIG. 22A, phenyl proprionic acid N (250 mg, 1.29 mmol) (prepared as described in Example 3), N-hydroxysuccinimide (302 mg, 2.57 mmol) and EDC·HCl (520 mg, 2.57 mmol) were added to a vial, followed by the addition of anhydrous THF (2.57 mL) and DMF (644 μL). The resulting mixture was stirred for an hour (material slowly dissolved) before the addition of ethanolamine (157 μL, 2.57 mmol). The reaction was stirred at room temperature overnight. In the morning a major spot was observed by TLC (UV, DCM:MeOH 9:1) and the mixture was poured into a separatory funnel containing 50 mL water and 50 mL EtOAc. The aqueous phase was extracted with ethyl acetate (3×30 mL), all organic layers were combined, washed with 0.1 M HCl, water, brine and dried over MgSO$_4$. After evaporation of the solvent the crude material was subjected to purification on a CombiFlash system (12 g silica, DCM:MeOH 100:0 to 90:10) to provide MM715 (120 mg, 39%) as a colourless solid. LRMS-HESI: calculated 260.09 m/z for [M+Na]$^+$, found 260.08 m/z, calculated 238.11 m/z for [M+H]$^+$, found 238.09. $^1$H NMR (400 MHz, CDCl$_3$) δ 6.72 (d, J=7.9 Hz, 1H), 6.68 (d, J=1.8 Hz, 1H), 6.64 (dd, J=7.9 Hz, 1.8 Hz, 1H), 5.91 (s, 2H), 5.89 (br s, 1H), 3.66 (t, J=5.0 Hz, 2H), 3.39-3.35 (m, 2H), 2.88 (t, J=7.6 Hz, 2H), 2.45 (t, J=7.6 Hz, 2H). (FIG. 22A, chemical reaction (c1), see: further also chemical reaction (c1) in FIG. 3B(ii)).

Figure 22B:
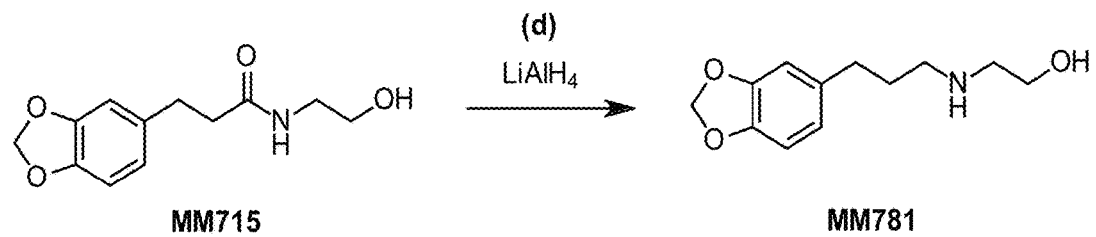

Referring to FIG. 22B, into a round bottomed flask was added MM715 (500 mg, 2.11 mmol), this was dissolved in dry THF (19.2 mL) and cooled to 0° C. Once cool, lithium aluminum hydride (2.0 M in THF, 4.21 mL, 8.43 mmol) was carefully added and the mixture was warmed to room temperature and left to react overnight. Monitoring by TLC (UV-vis, DCM:MeOH 9:1) showed the starting material had disappeared. The reaction was cooled to 0° C. and diluted with diethyl ether (20 mL). Added to this was 320 μL of water and, after vigorous bubbling had subsided, 320 μL 15% aqueous NaOH and finally an additional 960 μL water. After stirring for 10 minutes the mixture was dried with MgSO$_4$, filtered, and concentrated to leave a colourless oil. This material was subjected to FC (12 g silica, DCM:MeOH 100:0 to 85:15) to provide MM781 (281 mg, 60%) as a colourless solid. LRMS-HESI: calculated 224.13 m/z for [M+H]$^+$, found 224.10 m/z. $^1$H NMR (400 MHz, CDCl$_3$ δ 6.72 (d, J=7.8 Hz, 1H), 6.68-6.67 (m, 1H), 6.63-6.61 (m, 1H), 5.92 (s, 2H), 3.64-3.61 (m, 2H), 2.78-2.76 (m, 2H), 2.66-2.62 (m, 2H), 2.61-2.57 (m, 2H), 1.81-1.74 (m, 2H). (FIG. 22B, chemical reaction (d), see: further also chemical reaction (d) in FIG. 3B(ii)).

It is noted that MM781 corresponds with chemical compound C(X):

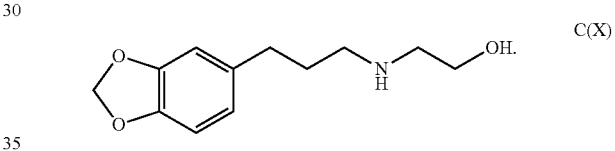

C(X)

Figure 23:
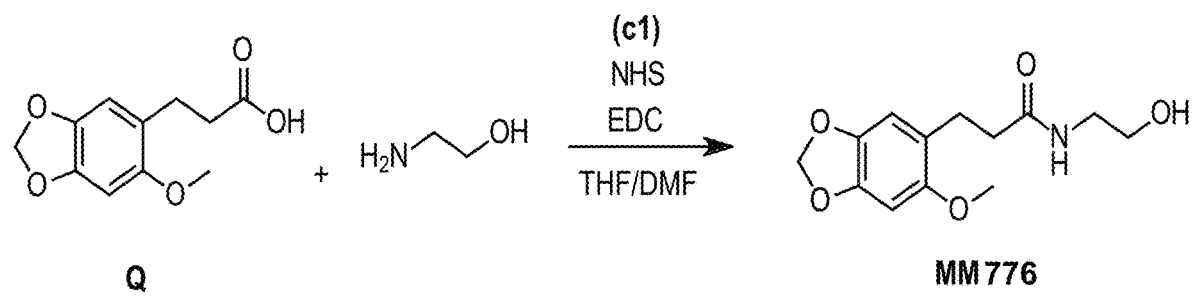
FIG. 23 depicts another example chemical reaction for the synthesis of another example compound according to the present disclosure.

Example 17—Preparation of a Seventeenth N-Propylamine Fused Heterocyclic Mescaline Derivative Referring to FIG. 23, intermediate Q (300 mg, 1.34 mmol) (prepared as described in Example 9), N-hydroxysuccinimide (314 mg, 2.68 mmol) and EDC·HCl (540 mg, 2.68 mmol) were added to a vial, followed by the addition of anhydrous THF (2.68 mL) and DMF (669 μL). The resulting mixture was stirred for an hour (material slowly dissolved) before the addition of ethanolamine (245 μL, 4.01 mmol). The reaction was stirred at room temperature overnight. In the morning a major spot was observed on TLC (UV, DCM:MeOH 9:1) and the mixture was poured into a separatory funnel containing 50 mL water and 50 mL EtOAc. The aqueous phase was extracted with ethyl acetate (3×30 mL), all organic layers were combined, washed with 0.1 M HCl, water, brine and dried over MgSO$_4$. After evaporation of the solvent the crude material was subjected to purification via flash chromatography (12 g silica, DCM:MeOH 100:0 to 90:10) to provide the pure product, MM776 (156 mg, 44%), as a colourless solid. LRMS-HESI: calculated 290.10 m/z for [M+Na]$^+$, found 290.07 m/z, calculated 268.12 m/z for [M+H]$^+$, found 268.13 m/z. $^1$H NMR (400 MHz, CDCl$_3$) δ 6.65 (s, 1H), 6.50 (s, 1H), 5.97 (br s, 1H), 5.88 (s, 2H), 3.76 (s, 3H), 3.67-3.65 (m, 2H), 3.39-3.35 (m, 2H), 2.85 (t, J=7.5 Hz, 2H), 2.73 (br s, 1H), 2.44 (t, J=7.6 Hz, 2H). (FIG. 23, chemical reaction (c1), see: further also chemical reaction (c1) in FIG. 3B(ii)).

It is noted that MM776 corresponds with chemical compound F(VI):

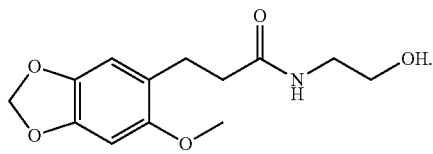

F(VI)

Figure 24:
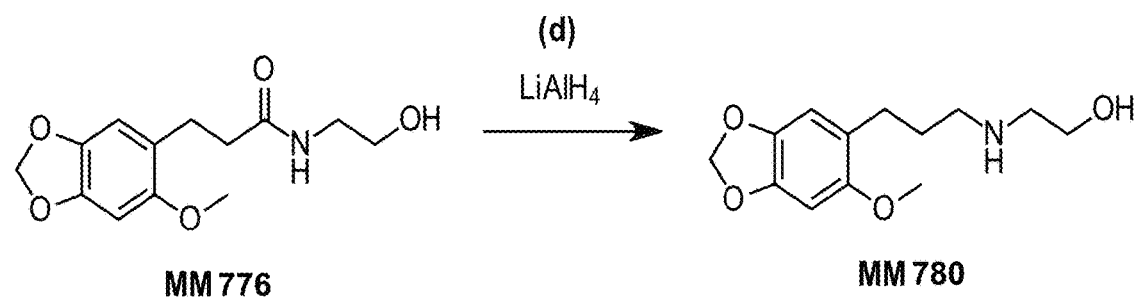
FIG. 24 depicts another example chemical reaction for the synthesis of another example compound according to the present disclosure.

Example 18—Preparation of an Eighteenth N-Propylamine Fused Heterocyclic Mescaline Derivative Referring to FIG. 24, into a round bottomed flask was added MM776 (75.0 mg, 281 µmol) (prepared as described in Example 17) this was dissolved in dry THF (2.55 mL) and cooled to 0° C. Once cool, lithium aluminum hydride (2.0 M in THF, 499 µL, 999 µmol) was carefully added and the mixture was warmed to room temperature and left to react overnight. Monitoring by TLC (UV-vis, DCM:MeOH 9:1) showed the starting material had disappeared. The reaction was cooled to 0° C. and diluted with diethyl ether (4 mL). Added to this was 40 µL of water and, after vigorous bubbling had subsided, 40 µL 15% aqueous NaOH and finally an additional 120 µL water. After stirring for 10 minutes the mixture was dried with $MgSO_4$, filtered, and concentrated to leave MM780 (28.4 mg, 40%) as a white solid. LRMS-HESI: calculated 254.14 m/z for $[M+H]^+$, found 254.14 m/z. $^1$H NMR (400 MHz, $CDCl_3$) δ 6.63 (s, 1H), 6.51 (s, 1H), 5.89 (s, 2H), 3.76 (s, 3H), 3.71-3.69 (m, 2H), 2.85-2.82 (m, 2H), 2.71, (t, J=7.1 Hz, 2H), 2.59 (t, J=7.4 Hz, 2H), 1.81 (p, J=7.3 Hz, 2H). (FIG. 24, chemical reaction (d), see: further also chemical reaction (d) in FIG. 3B(ii)).

It is noted that MM780 corresponds with chemical compound C(XII):

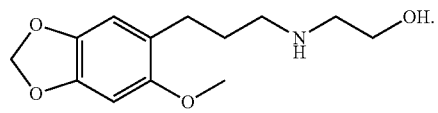

C(XII)

Figure 25A:
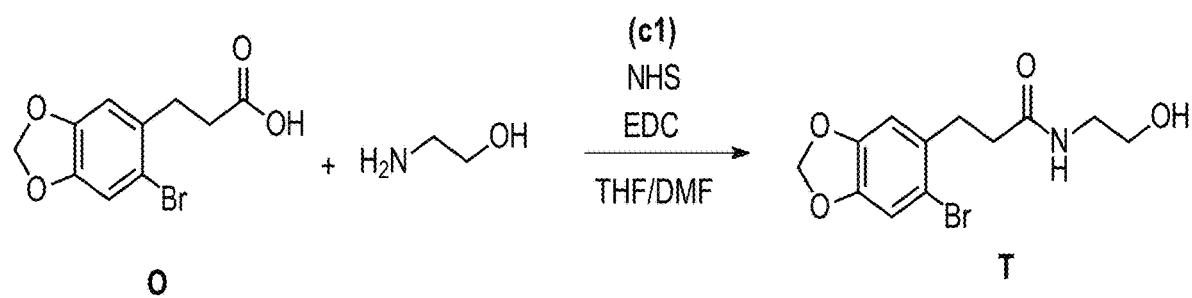
FIGS. 25A and 25B depict further example reactions in another example chemical synthesis pathway for the synthesis of another example compound according to the present disclosure.

Example 19—Preparation of a Nineteenth N-Propylamine Fused Heterocyclic Mescaline Derivative Referring to FIG. 25A, intermediate O (380 mg, 1.39 mmol) (prepared as described in Example 4), N-hydroxysuccinimide (327 mg, 2.78 mmol) and EDC·HCl (562 mg, 2.78 mmol) were added to a vial, followed by the addition of anhydrous THF (2.78 mL) and DMF (696 µL). The resulting mixture was stirred for an hour (material slowly dissolved) before the addition of ethanolamine (255 µL, 4.17 mmol). The reaction was stirred at room temperature overnight. In the morning a major spot was observed on TLC (UV, DCM:MeOH 9:1) and the mixture was poured into a separatory funnel containing 50 mL water and 50 mL EtOAc. The aqueous phase was extracted with ethyl acetate (3×30 mL), all organic layers were combined, washed with 0.1 M HCl, water, brine and dried over $MgSO_4$. After evaporation of the solvent the crude material was subjected to purification via FC (12 g silica, DCM:MeOH 100:0 to 90:10) to provide the pure product, intermediate T (246 mg, 56%), as a colourless solid. LRMS-HESI: calculated 338.00 m/z for $[M+Na]^+$, found 397.97 m/z, calculated 316.02 m/z for $[M+H]^+$, found 316.02 m/z. $^1$H NMR (400 MHz, $CDCl_3$) δ 6.97 (s, 1H), 6.74 (s, 1H), 6.02 (br s, 1H), 5.93 (s, 2H), 3.69-3.67 (m, 2H), 3.41-3.37 (m, 2H), 2.97 (t, J=7.6 Hz, 2H), 2.46 (t, J=7.7 Hz, 2H) (FIG. 25A, chemical reaction (c1), see: further also chemical reaction (c1) in FIG. 3B(ii)).

Figure 25B:
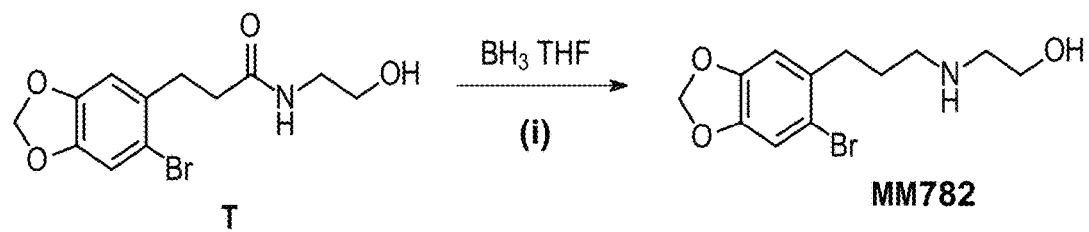

Referring to FIG. 25B, into a round bottomed flask was added intermediate T (90.0 mg, 285 µmol) this was dissolved in dry THF (2.59 mL) and cooled to 0° C. Once cool, borane-THF complex 1 M in THF (1.71 mL, 1.71 mmol) was carefully added and the mixture was heated to reflux for 4 hours. At this point LCMS determined substantial conversion had occurred and the mixture was cooled to 0° C. The excess borane was carefully quenched with saturated sodium bicarbonate solution and the resulting mixture was poured into a separatory funnel containing 5 mL DCM and 5 mL water. The aqueous layer was extracted with DCM (3×5 mL), all organic layers were combined, washed with brine, dried ($MgSO_4$), filtered and concentrated to give the crude material. Purification was carried out by FC (4 g silica, DCM:MeOH 100:0 to 85:15) to provide the pure material, MM782 (28.4 mg, 33%), as a colourless gummy solid. LRMS-HESI: calculated 302.04 m/z for $[M+H]^+$, found 302.01 m/z. $^1$H NMR (400 MHz, $CDCl_3$) δ 6.98 (s, 1H), 6.71 (s, 1H), 5.94 (s, 2H), 3.70-3.67 (m, 2H), 2.85-2.83 (m, 2H), 2.74-2.69 (m. 4H), 1.85-1.78 (m, 2H). (FIG. 25B, chemical reaction (i), see: further also chemical reaction (i) in FIG. 3B(ii)).

It is noted that MM782 corresponds with chemical compound C(XIII):

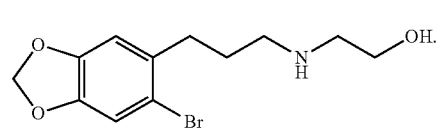

C(XIII)

5-$HT_{1A}$ receptor functional cellular response assay. Functional engagement of the 5-$HT_{1A}$ receptor within an engineered cell system was assessed as described for Example 2, except the compound with formula C(XIII) was evaluated in place of the compound with formula B(II). Table 2 shows functional assay results for positive controls, calibrators, and compound with formula C(XIII) in the form of $EC_{50}$ values. In view of results for controls and calibrator compounds, wherein a negative cellular response corresponded to an $EC_{50}$ value >1000 µM, the $EC_{50}$ value for the compound with formula C(XIII) in this assay (22.95 µM, Table 2) suggested ligand-receptor engagement.

Figure 26:
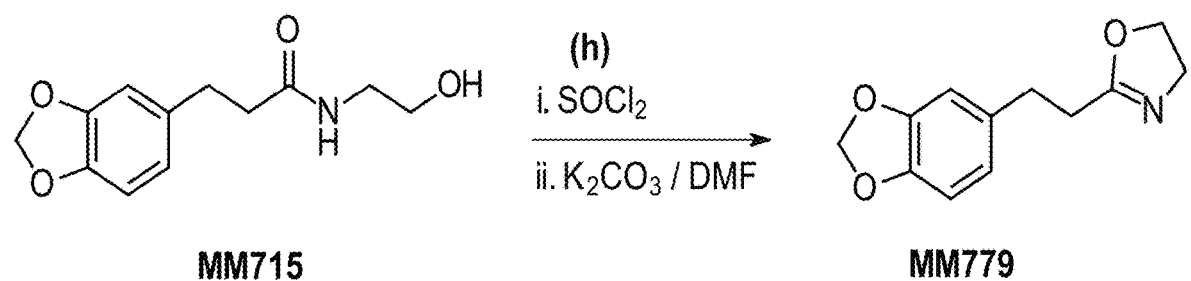
FIG. 26 depicts another example chemical reaction for the synthesis of another example compound according to the present disclosure.

Example 20—Preparation of a Twentieth N-Propylamine Fused Heterocyclic Mescaline Derivative Referring to FIG. 26, MM715 (95.0 mg, 400 µmol) (prepared as described in Example 16) was suspended in CHCl3 (3.09 mL). Added to this was thionyl chloride (88.5 µL, 1.20 mmol) and the mixture was left to stir at room temperature overnight. In the morning the reaction was monitored by TLC (UV, 9:1 DCM:MeOH). It was determined that no starting material remained and a new, less polar, compound had formed. The excess thionyl chloride was quenched with water and the reaction mixture was poured into a separatory funnel containing 15 mL of water. The aqueous layer was extracted with DCM (3×10 mL). All organic layers were combined, washed with water, brine, dried (MgSO₄), filtered and concentrated to provide the intermediate amido ethyl chloride (61.0 mg, 60%), as a yellow powder. LRMS-HESI: calculated 256.07 m/z for [M+H]⁺, found 256.08 m/z. ¹H NMR (400 MHz, CDCl₃) δ 6.74-6.64 (m, 3H), 5.92 (s, 2H), 5.74 (br s, 1H), 3.58-3.56 (m, 4H), 2.89 (t, J=7.5 Hz, 2H), 2.46 (t, J=7.6 Hz, 2H). This was used in the next step without further purification. Added to a vial was the amido ethyl chloride (47.0 mg, 184 µmol) and potassium carbonate (50.8 mg, 368 µmol) followed by DMF (888 µL). The temperature was increased to 75° C. and the mixture left to react overnight. In the morning the reaction was monitored by TLC (DCM:MeOH 9:1) and the mixture was observed to contain no starting material. The mixture was poured into a separatory funnel containing 10 mL of water and 10 mL of DCM. The aqueous layer was extracted with DCM (2×10 mL), all organic layers were combined, washed with water, brine, dried (MgSO₄) and filtered. The resulting tan oil was subjected to FC (4 g silica, DCM:MeOH 100:0 to 90:10) to provide the desired product MM779 (9.6 mg, 24%) as a colourless oil. LRMS-HESI: calculated 220.10 m/z for [M+H]⁺, found 220.07 m/z. ¹H NMR (400 MHz, CDCl₃) δ 6.72 (d, J=7.9 Hz, 1H), 6.70 (dd, J=1.7 Hz, 0.5 Hz, 1H), 6.67-6.64 (m, 1H), 5.92 (s, 2H), 4.25-4.20 (m, 2H), 3.85-3.79 (m, 2H), 2.89-2.85 (m, 2H), 2.55-2.51 (m, 2H). (FIG. 26, chemical reaction (h), see: further also chemical reaction (h) in FIG. 3B(iii)).

It is noted that MM779 corresponds with chemical compound G(I):

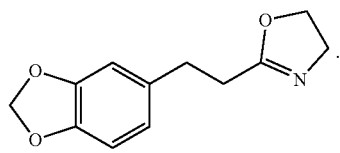

G(I)

Figure 27:
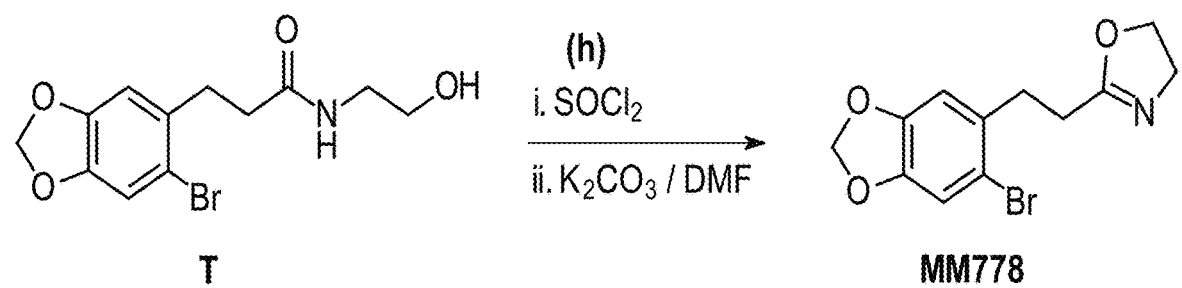
FIG. 27 depicts another example chemical reaction for the synthesis of another example compound according to the present disclosure.

Example 21—Preparation of a Twenty-First N-Propylamine Fused Heterocyclic Mescaline Derivative Referring to FIG. 27, intermediate T (121 mg, 383 µmol) (prepared as described in Example 19) was suspended in CHCl₃ (2.95 mL). Added to this was thionyl chloride (84.6 µL, 1.15 mmol) and the mixture was left to stir at room temperature overnight. In the morning the reaction was monitored by TLC (DCM:MeOH 9:1) and the mixture was observed to contain no starting material. The excess thionyl chloride was quenched with the addition of water and the resulting mixture was poured into a separatory funnel containing 10 mL of water and 10 mL of DCM. The aqueous layer was extracted with DCM (2×10 mL), all organic layers were combined, washed with water, brine, dried (MgSO₄) and filtered. Concentration of this solution provided the intermediate amido ethyl chloride the product (86.3 mg, 67%), isolated as a yellow solid. LRMS-HESI: calculated 333.98 m/z for [M+H]⁺, found 333.96 m/z. ¹H NMR (400 MHz, CDCl₃) δ 6.99 (s, 1H), 6.75 (s, 1H), 5.95 (s, 2H), 5.76 (br s, 1H), 3.58-3.57 (m, 2H), 3.00 (t, J=7.6 Hz, 2H), 2.47 (t, J=7.6 Hz, 2H). This was used in the next step without further purification. Added to a vial the amido ethyl chloride (59.0 mg, 176 µmol) and potassium carbonate (48.7 mg, 353 µmol) followed by DMF (852 µL). The temperature was increased to 75° C. and the mixture was left to react overnight. In the morning the reaction was monitored by TLC (DCM:MeOH 9:1) and the mixture was observed to contain no starting material. The mixture was poured into a separatory funnel containing 10 mL of water and 10 mL of DCM. The aqueous layer was extracted with DCM (2×10 mL), all organic layers were combined, washed with water, brine, dried (MgSO4) and filtered. After concentration the crude material was subjected to FC (4 g silica, DCM:MeOH 100:0 to 95:5) to provide the pure product, MM778 (35.0 mg, 67%), as a light yellow solid. LRMS-HESI: calculated 298.01 m/z for [M+H]⁺, found 298.00 m/z. ¹H NMR (400 MHz, CDCl3) δ 6.98 (s, 1H), 6.74 (s, 1H), 5.94 (s, 2H), 4.24 (t, J=9.5 Hz, 2H), 3.83 (t, J=9.5 Hz, 2H), 2.98 (t, J=7.9 Hz, 2H), 2.53 (t, J=8.0 Hz, 2H). (FIG. 27, chemical reaction (h), see: further also chemical reaction (h) in FIG. 3B(iii))

It is noted that MM778 corresponds with chemical compound G(I):

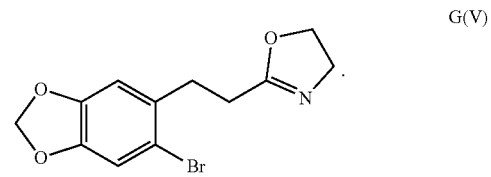 [SMILES: Brc1cc2c(cc1CCC1=NCCO1)OCO2]

G(V)

5-HT₁ₐ receptor functional cellular response assay. Functional engagement of the 5-HT₁ₐ receptor within an engineered cell system was assessed as described for Example 2, except the compound with formula G(V) was evaluated in place of the compound with formula B(II). Table 2 shows functional assay results for positive controls, calibrators, and compound with formula G(V) in the form of EC₅₀ values. In view of results for controls and calibrator compounds, wherein a negative cellular response corresponded to an EC₅₀ value >1000 µM, the EC₅₀ value for the compound with formula G(V) in this assay (129.5 µM, Table 2) suggested ligand-receptor engagement.

The invention claimed is:

1. A compound having chemical formula (I):

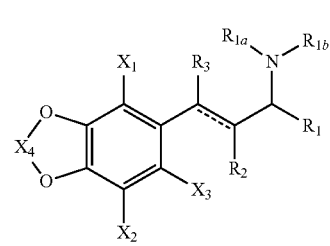

(I)

wherein, in chemical formula (I):
  ⸺ is a double bond;
  X₁, X₂, and X₃ are a hydrogen atom (H);
  X₄ is a methylene (—CH₂—) group or substituted methylene group;
  R₁ is a hydrogen atom (H);
  R₁ₐ and R₁ᵦ are each independently selected from an alkyl group, an alkyl-aryl group, or a hydrogen atom (H), or R₁ₐ and R₁ᵦ are joined together, along with the nitrogen atom to which they are attached, to form a 3-10-membered heterocyclic ring; and $R_2$ is an alkyl group and $R_3$ is a hydrogen atom (H), and wherein optionally the amino group ($-NR_{1a}R_{1b}$) is protonated to form ($-N^+HR_{1a}R_{1b}$), and chemical formula (I) or (II) further include a negatively charged anion balancing the positively charged nitrogen atom.

2. A compound according to claim 1, wherein $X_4$ is a substituted methylene group, optionally, a methylene group substituted with at least one halogen.

3. A compound according to claim 2, wherein the substituted methylene group is substituted with two non-identical or identical halogen substituents, optionally, ($-CF_2-$).

4. A compound according to claim 1, wherein the amino group ($-NR_{1a}R_{1b}$) is protonated to form ($-N^+HR_{1a}R_{1b}$), and chemical formula (I) further includes a negatively charged anion balancing the positively charged nitrogen atom.

5. A compound according to claim 1, wherein $R_2$ is a ($C_1$-$C_6$)-alkyl group, a ($C_1$-$C_3$)-alkyl group, or a methyl group.

6. A compound according to claim 1, wherein $R_2$ is a ($C_1$-$C_6$)-alkyl group, a ($C_1$-$C_3$)-alkyl group, an ethyl group, or a methyl group.

7. A compound according to claim 1, wherein $R_{1a}$ and $R_{1b}$ are joined together, along with the nitrogen atom to which they are attached, to form a 5-6-membered heterocyclic ring.

8. A compound according to claim 1, wherein the chemical compound having formula (I) is selected from the group of compounds having the chemical formula (B): B(I); B(II); B(III); B(IV); and B(V):

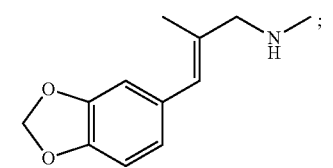

B(I)

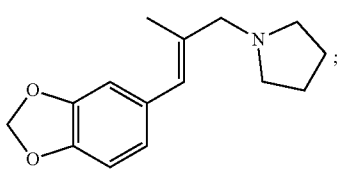

B(II)

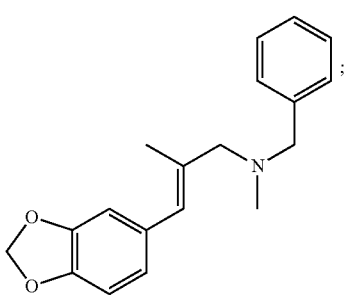

B(III)

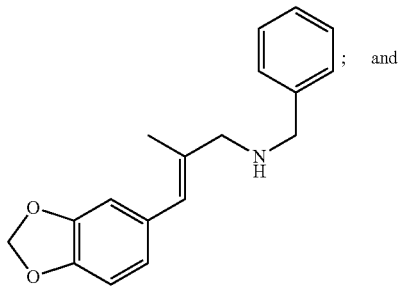

B(IV)

; and

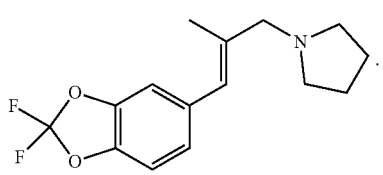

B(V)

9. A pharmaceutical drug formulation comprising an effective amount of the chemical compound according to claim 1, together with a pharmaceutically acceptable excipient, diluent, or carrier.

10. A method for treating a brain neurological disorder, the method comprising administering to a subject in need thereof a pharmaceutical formulation comprising the chemical compound according to claim 1, wherein the pharmaceutical formulation is administered in an effective amount to treat the brain neurological disorder in the subject, wherein the disorder is a dopamine active transporter (DAT) mediated disorder, an α-2AR-receptor mediated disorder, a 5-$HT_{1A}$-receptor mediated disorder, or a 5-$HT_{2A}$-receptor mediated disorder.

11. A pharmaceutical formulation comprising an effective amount of the chemical compound according to claim 8, together with a pharmaceutically acceptable excipient, diluent, or carrier.

12. A method for treating a brain neurological disorder, the method comprising administering to a subject in need thereof a pharmaceutical formulation comprising the chemical compound according to claim 8, wherein the pharmaceutical formulation is administered in an effective amount to treat the brain neurological disorder in the subject, wherein the disorder is a dopamine active transporter (DAT) mediated disorder, an α-2AR-receptor mediated disorder, a 5-$HT_{1A}$-receptor mediated disorder, or a 5-$HT_{2A}$-receptor mediated disorder.

* * * * *